US011235047B2

(12) United States Patent
Malley et al.

(10) Patent No.: US 11,235,047 B2
(45) Date of Patent: Feb. 1, 2022

(54) IMMUNOGENS AND METHODS FOR DISCOVERY AND SCREENING THEREOF

(71) Applicant: Children's Medical Center Corporation, Boston, MA (US)

(72) Inventors: Richard Malley, Beverly, MA (US); Yingjie Lu, West Roxbury, MA (US); Kristin L. Moffitt, Woburn, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/195,099

(22) Filed: Jun. 28, 2016

(65) Prior Publication Data

US 2017/0028050 A1 Feb. 2, 2017

Related U.S. Application Data

(63) Continuation of application No. 13/634,357, filed as application No. PCT/US2011/028052 on Mar. 11, 2011, now abandoned.

(60) Provisional application No. 61/313,450, filed on Mar. 12, 2010, provisional application No. 61/428,305, filed on Dec. 30, 2010, provisional application No. 61/428,296, filed on Dec. 30, 2010.

(51) Int. Cl.
*A61K 39/09* (2006.01)
*C07K 14/315* (2006.01)
*A61K 39/00* (2006.01)

(52) U.S. Cl.
CPC ........ *A61K 39/092* (2013.01); *C07K 14/3156* (2013.01); *A61K 2039/55544* (2013.01); *A61K 2039/55583* (2013.01); *A61K 2039/70* (2013.01); *C07K 2319/00* (2013.01)

(58) Field of Classification Search
None
See application file for complete search history.

(56) References Cited

U.S. PATENT DOCUMENTS

| | | |
|---|---|---|
| 7,217,791 B2 | 5/2007 | Chen et al. |
| 7,585,669 B2 | 9/2009 | Chen et al. |
| 2005/0002948 A1 | 1/2005 | Ryall |
| 2005/0226899 A1 | 10/2005 | Castiglioni et al. |
| 2007/0082005 A1 | 4/2007 | Doucette-Stamm |
| 2007/0184443 A1 | 8/2007 | Covacci |
| 2008/0160045 A1 | 7/2008 | Contorni et al. |
| 2009/0068288 A1 | 3/2009 | Kruger |
| 2010/0330112 A1 | 12/2010 | Long et al. |
| 2011/0020386 A1 | 1/2011 | Gierahn et al. |
| 2011/0159040 A1 | 6/2011 | Malley et al. |
| 2011/0293664 A1 | 12/2011 | Cohane et al. |
| 2012/0135025 A1 | 5/2012 | Flechtner et al. |
| 2012/0189649 A1 | 7/2012 | Gierahn et al. |
| 2012/0251577 A1 | 10/2012 | Malley et al. |

FOREIGN PATENT DOCUMENTS

| | | |
|---|---|---|
| WO | 90/11087 A1 | 10/1990 |
| WO | 1999/003884 A2 | 1/1999 |
| WO | 00/06737 A2 | 2/2000 |
| WO | 2000/06738 A2 | 10/2000 |
| WO | 01/40472 A2 | 6/2001 |
| WO | 02/077021 A2 | 10/2002 |
| WO | 03/044185 A2 | 5/2003 |
| WO | 2006/084467 A1 | 8/2006 |
| WO | 2008/119358 A2 | 10/2008 |
| WO | 2009/016515 A2 | 2/2009 |
| WO | 2009/143413 A1 | 11/2009 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Basset et al., "Antiboby-dependent, CD4(+) T-Cell-Dependent protection against pneumococcal colonization elicited by intranasal immunization with purified pneumococcal proteins", Infection and Immunity, American Society for Macrobiology 75(10):5460-5464 (2007).
Bowie et al., "Deciphering the Message in Protein Sequences: Tolerance to Amino Acid Substitutions", Science 247:1306-1310 (1990).
Greenspan et al., "Defining epitopes: It's not as easy as it seems", Nature Biology 17:936-937 (1999).
Laine et al., "Age-specific immunoglobulin G (IgG) and IgA to pneumococcal protein antigens in a population in coastal Kenya", Infection and Immunity 72(6):3331-3335 (2004).
Ling et al., "Glycolytic enzymes associated with the cell surface of *Streptococcus pneumoniae* are antigenic in humans and elicit protective immune responses in the mouse", Clin Exp Immunol. 138:290-298 (2004).
Lu et al., "A Bivalent Vaccine to Protect against *Streptococcus pneumonaie* and *Salmonella typhi*", Vaccine 30(23):3405-3412 (2012).
Lu et al., "Interleukin-17A Mediates Acquired Immunity to Pneumococcal Colonization", PLoS Pathogens 4(9):1-11 (2008).
Lu et al., "Protection against Pneumococcal Colonization and Fatal Pneumonia by a Trivalent Conjugate of a Fusion Protein with the Cell Wall Polysaccharide", Infection and Immunity 77(5):2076-2083 (2009).

(Continued)

*Primary Examiner* — Robert A Zeman
(74) *Attorney, Agent, or Firm* — Nixon Peabody LLP

(57) ABSTRACT

The present application is generally directed to methods for identifying immunogens from organisms and pathogens, and in particular for identifying immunogens which when administered as vaccines elicit a cellular and/or humoral immune response. The present application is also directed to pneumococcal T-cell immunogens, and vaccine compositions comprising one or a combination of pneumococcal immunogens and methods for treating or preventing pneumococcal infections using the vaccines thereof. The present invention also encompasses use of the pneumococcal immunogens for diagnostic purposes to identify a subject with a pneumococcal infection.

9 Claims, 4 Drawing Sheets
Specification includes a Sequence Listing.

(56) References Cited

OTHER PUBLICATIONS

Malley., "Antibody and cell-mediated immunity to *Streptococcus pneumoniae*: implications for vaccine development", Journal of Molecular Medicine 88(2):135-142 (2010).

Malley et al., "CD4+ T Cells Mediate Antibody-Independent Acquired Immunity to Pneumococcal Colonization", PNAS 102(13):4848-4853 (2005).

Malley et al., "Intranasal immunization with killed unencapsulated whole cells prevents colonization and invasive disease by capsulated Pneumococci", Infections and Immunity 69(8):4870-4873 (2001).

Malley et al., "Multiserotype Protection of Mice Against Pneumococcal Colonization of the Nasopharynx and Middle Ear by Killed Nonencapsulated Cells Given Intranasally with a Nontoxic Adjuvant", Infection and Immunity 72(7):4290-4292 (2004).

Moffitt et al., "Identification of Protective Pneumococcal Th17 Antigens from the Soluble Fraction of a Killed Whole Cell Vaccine", PLoS One 7(8):e43445 (2012).

Moffitt et al., "T17-Based vaccine design for prevention of colonization", Cell Host and Microbe 158-165 (2010).

Portnoi et al., "The vaccine potential of *Streptococcus pneumoniae* surface lectin- and non-lectin proteins", Vaccine 24(11):1868-1873 (2006).

Trzcinski et al., "Antibodies to Conserved Pneumococcal Antigens Correlate with, but Are Not Required for, Protection Against Pneumococcal Colonization Induced by Prior Exposure in a Mouse Model", Infection and Immunity 73(10):7043-7046 (2005).

Vickerman et al., "Genome-wide transcriptional changes in *Streptococcus gordonii* in response to competence signaling pepetide", Journal of Bacteriology 189:7799-7807 (2007).

Wizemann et al., "Use of a Whole Genome Appraoch to Identify Vaccine Molecules Affording Protection against *Streptococcus pneumoniae* Infection" Infection and Immunity 69(3) 1593-1598 (2001).

Ahmad et al., "Sequential release of antigens from chloroform-treated *Staphylococcus epidermidis*: application towards a possible vaccine", Journal of Applications in Bacteriology 69(5):676-685 (1990).

Beghetto et al., "Discovery of novel *Streptococcus pneumoniae* antigens by screening a whole-genome lambda-display library", FEMS Microbiology Letters 262(1):14-21 (2006).

Extended European Search Report in correspondign European Search Report No. 11754142.5 dated Oct. 29, 2013.

Zhang et al., "Multiple antigen-presenting system (MAPS) to induce comprehensive B- and T-cell immunity" PNAS 110(33) 13564-13569 (2013).

Nordlund et al., "Tetravalent single-chain avidin: from subunits to protein domains via circularly permuted avidins" Biochem J 392(Pt 3) 485-491 (2005).

Wizeman et al., "Use of a while Genome Appraoch to Identify Vaccine Molecules Affording Protection against *Streptococcus pneumoniae* Infection" Infection and Immunity 69(3) 1593-1598 (2001).

"Baiosaiensu no toukeigaku (Statistics for Bioscience)—Tadashiku katsuyou surutame no jissen riron (Practical Theories for Proper Application)", Nankodo Co., Ltd., 1999, pp. 90, 360.

International Search Report for PCT/US11/28052 (Novel Immunogens and Methods for Discovery and Screening Thereof, filed Mar. 11, 2011) issued by ISA/KR, 6 pages (dated Dec. 27, 2011).

Wizemann et al., "Use of a whole Genome Approach to Identify Vaccine Molecules Affording Protection against *Streptococcus pneumoniae* Infection" Infection and Immunity 69(3):1593-1598 (2001).

Written Opinion for PCT/US11/28052 (Novel Immunogens and Methods for Discovery and Screening Thereof, filed Mar. 11, 2011) issued by ISA/KR, 6 pages (dated Dec. 27, 2011).

\* cited by examiner

Splenocyte stimulation

SEQUENCE LISTING

```
<160> NUMBER OF SEQ ID NOS: 51

<210> SEQ ID NO 1
<211> LENGTH: 398
<212> TYPE: PRT
<213> ORGANISM: Streptococcus pyogenes

<400> SEQUENCE: 1

Met Ala Lys Leu Thr Val Lys Asp Val Asp Leu Lys Gly Lys Lys Val
1               5                   10                  15

Leu Val Arg Val Asp Phe Asn Val Pro Leu Lys Asp Gly Val Ile Thr
            20                  25                  30

Asn Asp Asn Arg Ile Thr Ala Ala Leu Pro Thr Ile Lys Tyr Ile Ile
        35                  40                  45

Glu Gln Gly Gly Arg Ala Ile Leu Phe Ser His Leu Gly Arg Val Lys
    50                  55                  60

Glu Glu Ala Asp Lys Glu Gly Lys Ser Leu Ala Pro Val Ala Ala Asp
65                  70                  75                  80

Leu Ala Ala Lys Leu Gly Gln Asp Val Val Phe Pro Gly Val Thr Arg
                85                  90                  95

Gly Ser Lys Leu Glu Glu Ala Ile Asn Ala Leu Glu Asp Gly Gln Val
            100                 105                 110

Leu Leu Val Glu Asn Thr Arg Phe Glu Asp Val Asp Gly Lys Lys Glu
        115                 120                 125

Ser Lys Asn Asp Glu Glu Leu Gly Lys Tyr Trp Ala Ser Leu Gly Asp
    130                 135                 140

Gly Ile Phe Val Asn Asp Ala Phe Gly Thr Ala His Arg Ala His Ala
145                 150                 155                 160

Ser Asn Val Gly Ile Ser Ala Asn Val Glu Lys Ala Val Ala Gly Phe
                165                 170                 175

Leu Leu Glu Asn Glu Ile Ala Tyr Ile Gln Glu Ala Val Glu Thr Pro
            180                 185                 190

Glu Arg Pro Phe Val Ala Ile Leu Gly Gly Ser Lys Val Ser Asp Lys
        195                 200                 205

Ile Gly Val Ile Glu Asn Leu Leu Glu Lys Ala Asp Lys Val Leu Ile
    210                 215                 220

Gly Gly Gly Met Thr Tyr Thr Phe Tyr Lys Ala Gln Gly Ile Glu Ile
225                 230                 235                 240

Gly Asn Ser Leu Val Glu Glu Asp Lys Leu Asp Val Ala Lys Asp Leu
                245                 250                 255

Leu Glu Lys Ser Asn Gly Lys Leu Ile Leu Pro Val Asp Ser Lys Glu
            260                 265                 270

Ala Asn Ala Phe Ala Gly Tyr Thr Glu Val Arg Asp Thr Glu Gly Glu
        275                 280                 285

Ala Val Ser Glu Gly Phe Leu Gly Leu Asp Ile Gly Pro Lys Ser Ile
    290                 295                 300

Ala Glu Phe Asp Gln Ala Leu Thr Gly Ala Lys Thr Val Val Trp Asn
305                 310                 315                 320

Gly Pro Met Gly Val Phe Glu Asn Pro Asp Phe Gln Ala Gly Thr Ile
```

```
                    325                 330                 335
Gly Val Met Asp Ala Ile Val Lys Gln Pro Gly Val Lys Ser Ile Ile
            340                 345                 350
Gly Gly Gly Asp Ser Ala Ala Ala Ile Asn Leu Gly Arg Ala Asp
            355                 360                 365
Lys Phe Ser Trp Ile Ser Thr Gly Gly Ala Ser Met Glu Leu Leu
    370                 375                 380
Glu Gly Lys Val Leu Pro Gly Leu Ala Ala Leu Thr Glu Lys
385                 390                 395

<210> SEQ ID NO 2
<211> LENGTH: 399
<212> TYPE: PRT
<213> ORGANISM: Streptococcus thermophilus

<400> SEQUENCE: 2

Met Ala Lys Leu Thr Val Lys Asp Val Glu Leu Lys Gly Lys Lys Val
1               5                   10                  15
Leu Val Arg Val Asp Phe Asn Val Pro Val Lys Asp Gly Val Ile Thr
            20                  25                  30
Asn Asp Asn Arg Ile Thr Ala Ala Leu Pro Thr Ile Lys Tyr Ile Leu
        35                  40                  45
Glu Gln Gly Gly Arg Ala Ile Leu Phe Ser His Leu Gly Arg Val Lys
    50                  55                  60
Glu Glu Ala Asp Lys Glu Gly Lys Ser Leu Ala Pro Val Ala Ala Asp
65                  70                  75                  80
Leu Ala Ala Lys Leu Gly Gln Asp Val Lys Phe Ile Pro Gly Val Thr
                85                  90                  95
Arg Gly Ala Glu Leu Glu Ala Ala Val Asn Ser Leu Glu Asp Gly Gln
            100                 105                 110
Val Leu Leu Val Glu Asn Thr Arg Phe Glu Asp Val Asp Gly Lys Lys
        115                 120                 125
Glu Ser Lys Asn Asp Pro Glu Leu Gly Lys Tyr Trp Ala Ser Leu Gly
    130                 135                 140
Asp Gly Ile Phe Val Asn Asp Ala Phe Gly Thr Ala His Arg Ala His
145                 150                 155                 160
Ala Ser Asn Val Gly Ile Ser Ala Asn Val Glu Lys Ala Val Ala Gly
                165                 170                 175
Phe Leu Leu Glu Asn Glu Ile Ala Tyr Ile Gln Glu Ala Val Glu Asn
            180                 185                 190
Pro Glu Arg Pro Phe Val Ala Ile Leu Gly Gly Ser Lys Val Ser Asp
        195                 200                 205
Lys Ile Gly Val Ile Glu Asn Leu Leu Glu Lys Ala Asp Lys Val Leu
    210                 215                 220
Ile Gly Gly Gly Met Thr Tyr Thr Phe Phe Lys Ala Gln Gly Ile Glu
225                 230                 235                 240
Ile Gly Asn Ser Leu Val Glu Asp Lys Leu Asp Val Ala Lys Ala
                245                 250                 255
Leu Leu Glu Lys Ser Asn Gly Lys Leu Ile Leu Pro Val Asp Ser Lys
            260                 265                 270
Glu Ala Asn Ala Phe Ala Asp Tyr Thr Glu Val Lys Tyr Thr Glu Gly
        275                 280                 285
Glu Ala Val Asp Pro Gly Phe Leu Gly Leu Asp Ile Gly Pro Lys Ser
    290                 295                 300
```

Ile Ala Lys Phe Asp Glu Ala Leu Thr Gly Ala Lys Thr Val Val Trp
305                 310                 315                 320

Asn Gly Pro Met Gly Val Phe Glu Asn Pro Asp Phe Gln Ala Gly Thr
            325                 330                 335

Ile Gly Val Met Asp Ala Ile Val Lys Gln Pro Gly Val Lys Ser Ile
        340                 345                 350

Ile Gly Gly Gly Asp Ser Ala Ala Ala Ile Asn Leu Gly Tyr Ala
    355                 360                 365

Asp Lys Phe Ser Trp Ile Ser Thr Gly Gly Ala Ser Met Glu Leu
370                 375                 380

Leu Glu Gly Lys Glu Leu Pro Gly Leu Ala Ala Leu Thr Glu Lys
385                 390                 395

<210> SEQ ID NO 3
<211> LENGTH: 434
<212> TYPE: PRT
<213> ORGANISM: Streptococcus pneumoniae

<400> SEQUENCE: 3

Met Ser Ile Ile Thr Asp Val Tyr Ala Arg Glu Val Leu Asp Ser Arg
1               5                   10                  15

Gly Asn Pro Thr Leu Glu Val Glu Val Tyr Thr Glu Ser Gly Ala Phe
            20                  25                  30

Gly Arg Gly Met Val Pro Ser Gly Ala Ser Thr Gly Glu His Glu Ala
        35                  40                  45

Val Glu Leu Arg Asp Gly Asp Lys Ser Arg Tyr Gly Gly Leu Gly Thr
    50                  55                  60

Gln Lys Ala Val Asp Asn Val Asn Asn Ile Ile Ala Glu Ala Ile Ile
65                  70                  75                  80

Gly Tyr Asp Val Arg Asp Gln Gln Ala Ile Asp Arg Ala Met Ile Ala
                85                  90                  95

Leu Asp Gly Thr Pro Asn Lys Gly Lys Leu Gly Ala Asn Ala Ile Leu
            100                 105                 110

Gly Val Ser Ile Ala Val Ala Arg Ala Ala Ala Asp Tyr Leu Glu Ile
        115                 120                 125

Pro Leu Tyr Ser Tyr Leu Gly Gly Phe Asn Thr Lys Val Leu Pro Thr
    130                 135                 140

Pro Met Met Asn Ile Ile Asn Gly Gly Ser His Ser Asp Ala Pro Ile
145                 150                 155                 160

Ala Phe Gln Glu Phe Met Ile Leu Pro Val Gly Ala Pro Thr Phe Lys
                165                 170                 175

Glu Ala Leu Arg Tyr Gly Ala Glu Ile Phe His Ala Leu Lys Lys Ile
            180                 185                 190

Leu Lys Ser Arg Gly Leu Glu Thr Ala Val Gly Asp Glu Gly Gly Phe
        195                 200                 205

Ala Pro Arg Phe Glu Gly Thr Glu Asp Gly Val Glu Thr Ile Leu Ala
    210                 215                 220

Ala Ile Glu Ala Ala Gly Tyr Val Pro Gly Lys Asp Val Phe Leu Gly
225                 230                 235                 240

Phe Asp Cys Ala Ser Ser Glu Phe Tyr Asp Lys Glu Arg Lys Val Tyr
                245                 250                 255

Asp Tyr Thr Lys Phe Glu Gly Glu Gly Ala Ala Val Arg Thr Ser Ala
            260                 265                 270

Glu Gln Ile Asp Tyr Leu Glu Gly Leu Val Asn Lys Tyr Pro Ile Ile
        275                 280                 285

```
Thr Ile Glu Asp Gly Met Asp Glu Asn Asp Trp Asp Gly Trp Lys Ala
            290                 295                 300

Leu Thr Glu Arg Leu Gly Lys Lys Val Gln Leu Val Gly Asp Asp Phe
305                 310                 315                 320

Phe Val Thr Asn Thr Asp Tyr Leu Ala Arg Gly Ile Gln Glu Gly Ala
                325                 330                 335

Ala Asn Ser Ile Leu Ile Lys Val Asn Gln Ile Gly Thr Leu Thr Glu
                340                 345                 350

Thr Phe Glu Ala Ile Glu Met Ala Lys Glu Ala Gly Tyr Thr Ala Val
                355                 360                 365

Val Ser His Arg Ser Gly Glu Thr Glu Asp Ser Thr Ile Ala Asp Ile
            370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Gln
                405                 410                 415

Leu Gly Glu Val Ala Glu Tyr Arg Gly Leu Lys Ser Phe Tyr Asn Leu
                420                 425                 430

Lys Lys

<210> SEQ ID NO 4
<211> LENGTH: 432
<212> TYPE: PRT
<213> ORGANISM: Streptococcus mutans

<400> SEQUENCE: 4

Met Ser Ile Ile Thr Asp Val Tyr Ala Arg Glu Val Leu Asp Ser Arg
1               5                   10                  15

Gly Asn Pro Thr Leu Glu Val Glu Val Tyr Thr Glu Ser Gly Ala Phe
                20                  25                  30

Gly Arg Gly Met Val Pro Ser Gly Ala Ser Thr Gly Glu His Glu Ala
            35                  40                  45

Val Glu Leu Arg Asp Gly Asp Lys Ser Arg Tyr Gly Gly Leu Gly Thr
50                  55                  60

Gln Lys Ala Val Asp Asn Val Asn Asn Ile Ile Ala Glu Ala Leu Ile
65                  70                  75                  80

Gly Tyr Asp Val Arg Asp Gln Gln Ala Ile Asp Lys Ala Met Ile Ala
                85                  90                  95

Leu Asp Gly Thr Pro Asn Lys Gly Lys Leu Gly Ala Asn Ala Ile Leu
                100                 105                 110

Gly Val Ser Ile Ala Val Ala Arg Ala Ala Ala Asp Phe Leu Glu Ile
            115                 120                 125

Pro Leu Tyr Ser Tyr Leu Gly Gly Phe Asn Thr Lys Val Leu Pro Thr
130                 135                 140

Pro Met Met Asn Ile Ile Asn Gly Gly Ser His Ser Asp Ala Pro Ile
145                 150                 155                 160

Ala Phe Gln Glu Phe Met Ile Val Pro Ala Gly Ala Pro Thr Phe Lys
                165                 170                 175

Glu Ala Leu Arg Trp Gly Ala Glu Ile Phe His Ala Leu Lys Lys Ile
                180                 185                 190

Leu Lys Glu Arg Gly Leu Glu Thr Ala Val Gly Asp Glu Gly Gly Phe
            195                 200                 205

Ala Pro Lys Phe Asp Gly Thr Glu Asp Ala Val Glu Thr Ile Ile Lys
210                 215                 220
```

Ala Ile Glu Thr Ala Gly Tyr Lys Pro Gly Glu Val Phe Leu Gly
225                 230                 235                 240

Phe Asp Cys Ala Ser Ser Glu Phe Tyr Asp Asn Gly Val Tyr Asp Tyr
                245                 250                 255

Thr Lys Phe Glu Gly Glu Lys Gly Ala Lys Arg Ser Ala Ala Glu Gln
            260                 265                 270

Ile Asp Tyr Ile Glu Glu Leu Val Asn Lys Tyr Pro Ile Ile Thr Ile
        275                 280                 285

Glu Asp Ala Met Asp Glu Asn Asp Trp Asp Gly Trp Lys Ala Leu Thr
290                 295                 300

Ala Arg Leu Gly Asp Arg Val Gln Leu Val Gly Asp Asp Phe Phe Val
305                 310                 315                 320

Thr Asn Thr Asp Tyr Leu Ala Arg Gly Ile Lys Glu Gly Ala Ala Asn
                325                 330                 335

Ser Ile Leu Ile Lys Val Asn Gln Ile Gly Thr Leu Thr Glu Thr Phe
            340                 345                 350

Glu Ala Ile Glu Met Ala Lys Glu Ala Gly Tyr Thr Ala Val Val Ser
        355                 360                 365

His Arg Ser Gly Glu Thr Glu Asp Ser Thr Ile Ala Asp Ile Ser Val
370                 375                 380

Ala Thr Asn Ala Gly Gln Ile Lys Thr Gly Ser Leu Ser Arg Thr Asp
385                 390                 395                 400

Arg Ile Ala Lys Tyr Asn Gln Leu Leu Arg Ile Glu Asp Gln Leu Gly
                405                 410                 415

Glu Val Ala Glu Tyr Arg Gly Leu Lys Ser Phe Tyr Asn Leu Lys Lys
            420                 425                 430

<210> SEQ ID NO 5
<211> LENGTH: 398
<212> TYPE: PRT
<213> ORGANISM: Streptococcus pyogenes

<400> SEQUENCE: 5

Met Ala Lys Glu Lys Tyr Asp Arg Ser Lys Pro His Val Asn Ile Gly
1               5                   10                  15

Thr Ile Gly His Val Asp His Gly Lys Thr Thr Leu Thr Ala Ala Ile
            20                  25                  30

Thr Thr Val Leu Ala Arg Arg Leu Pro Ser Ser Val Asn Gln Pro Lys
        35                  40                  45

Asp Tyr Ala Ser Ile Asp Ala Ala Pro Glu Glu Arg Glu Arg Gly Ile
50                  55                  60

Thr Ile Asn Thr Ala His Val Glu Tyr Glu Thr Ala Thr Arg His Tyr
65                  70                  75                  80

Ala His Ile Asp Ala Pro Gly His Ala Asp Tyr Val Lys Asn Met Ile
                85                  90                  95

Thr Gly Ala Ala Gln Met Asp Gly Ala Ile Leu Val Val Ala Ser Thr
            100                 105                 110

Asp Gly Pro Met Pro Gln Thr Arg Glu His Ile Leu Leu Ser Arg Gln
        115                 120                 125

Val Gly Val Lys His Leu Ile Val Phe Met Asn Lys Val Asp Leu Val
        130                 135                 140

Asp Asp Glu Glu Leu Leu Glu Leu Val Glu Met Glu Ile Arg Asp Leu
145                 150                 155                 160

Leu Ser Glu Tyr Asp Phe Pro Gly Asp Asp Leu Pro Val Ile Gln Gly

```
                165                 170                 175
Ser Ala Leu Lys Ala Leu Glu Gly Asp Thr Lys Phe Glu Asp Ile Ile
                    180                 185                 190

Met Glu Leu Met Asp Thr Val Asp Ser Tyr Ile Pro Glu Pro Glu Arg
            195                 200                 205

Asp Thr Asp Lys Pro Leu Leu Leu Pro Val Glu Asp Val Phe Ser Ile
        210                 215                 220

Thr Gly Arg Gly Thr Val Ala Ser Gly Arg Ile Asp Arg Gly Thr Val
225                 230                 235                 240

Arg Val Asn Asp Glu Ile Glu Ile Val Gly Ile Lys Glu Thr Lys
                245                 250                 255

Lys Ala Val Val Thr Gly Val Glu Met Phe Arg Lys Gln Leu Asp Glu
                260                 265                 270

Gly Leu Ala Gly Asp Asn Val Gly Ile Leu Leu Arg Gly Val Gln Arg
                275                 280                 285

Asp Glu Ile Glu Arg Gly Gln Val Ile Ala Lys Pro Gly Ser Ile Asn
        290                 295                 300

Pro His Thr Lys Phe Lys Gly Glu Val Tyr Ile Leu Ser Lys Asp Glu
305                 310                 315                 320

Gly Gly Arg His Thr Pro Phe Phe Asn Asn Tyr Arg Pro Gln Phe Tyr
                325                 330                 335

Phe Arg Thr Thr Asp Val Thr Gly Ser Ile Glu Leu Pro Ala Gly Thr
                340                 345                 350

Glu Met Val Met Pro Gly Asp Asn Val Thr Ile Asn Val Glu Leu Ile
            355                 360                 365

His Pro Ile Ala Val Glu Gln Gly Thr Thr Phe Ser Ile Arg Glu Gly
        370                 375                 380

Gly Arg Thr Val Gly Ser Gly Ile Val Ser Glu Ile Glu Ala
385                 390                 395

<210> SEQ ID NO 6
<211> LENGTH: 398
<212> TYPE: PRT
<213> ORGANISM: Streptococcus pneumoniae

<400> SEQUENCE: 6

Met Ala Lys Glu Lys Tyr Asp Arg Ser Lys Pro His Val Asn Ile Gly
1               5                   10                  15

Thr Ile Gly His Val Asp His Gly Lys Thr Thr Leu Thr Ala Ala Ile
                20                  25                  30

Thr Thr Val Leu Ala Arg Arg Leu Pro Ser Ser Val Asn Gln Pro Lys
            35                  40                  45

Asp Tyr Ala Ser Ile Asp Ala Ala Pro Glu Glu Arg Glu Arg Gly Ile
    50                  55                  60

Thr Ile Asn Thr Ala His Val Glu Tyr Glu Thr Glu Lys Arg His Tyr
65                  70                  75                  80

Ala His Ile Asp Ala Pro Gly His Ala Asp Tyr Val Lys Asn Met Ile
                85                  90                  95

Thr Gly Ala Ala Gln Met Asp Gly Ala Ile Leu Val Val Ala Ser Thr
            100                 105                 110

Asp Gly Pro Met Pro Gln Thr Arg Glu His Ile Leu Leu Ser Arg Gln
        115                 120                 125

Val Gly Val Lys His Leu Ile Val Phe Met Asn Lys Val Asp Leu Val
    130                 135                 140
```

```
Asp Asp Glu Glu Leu Leu Glu Leu Val Glu Met Glu Ile Arg Asp Leu
145                 150                 155                 160

Leu Ser Glu Tyr Asp Phe Pro Gly Asp Leu Pro Val Ile Gln Gly
            165                 170                 175

Ser Ala Leu Lys Ala Leu Glu Gly Asp Ser Lys Tyr Glu Asp Ile Val
            180                 185                 190

Met Glu Leu Met Asn Thr Val Asp Glu Tyr Ile Pro Glu Pro Glu Arg
            195                 200                 205

Asp Thr Asp Lys Pro Leu Leu Leu Pro Val Glu Asp Val Phe Ser Ile
210                 215                 220

Thr Gly Arg Gly Thr Val Ala Ser Gly Arg Ile Asp Arg Gly Ile Val
225                 230                 235                 240

Lys Val Asn Asp Glu Ile Glu Ile Val Gly Ile Lys Glu Glu Thr Gln
            245                 250                 255

Lys Ala Val Val Thr Gly Val Glu Met Phe Arg Lys Gln Leu Asp Glu
            260                 265                 270

Gly Leu Ala Gly Asp Asn Val Gly Val Leu Leu Arg Gly Val Gln Arg
            275                 280                 285

Asp Glu Ile Glu Arg Gly Gln Val Ile Ala Lys Pro Gly Ser Ile Asn
290                 295                 300

Pro His Thr Lys Phe Lys Gly Glu Val Tyr Ile Leu Thr Lys Glu Glu
305                 310                 315                 320

Gly Gly Arg His Thr Pro Phe Phe Asn Asn Tyr Arg Pro Gln Phe Tyr
            325                 330                 335

Phe Arg Thr Thr Asp Val Thr Gly Ser Ile Glu Leu Pro Ala Gly Thr
            340                 345                 350

Glu Met Val Met Pro Gly Asp Asn Val Thr Ile Asp Val Glu Leu Ile
            355                 360                 365

His Pro Ile Ala Val Glu Gln Gly Thr Thr Phe Ser Ile Arg Glu Gly
            370                 375                 380

Gly Arg Thr Val Gly Ser Gly Met Val Thr Glu Ile Glu Ala
385                 390                 395

<210> SEQ ID NO 7
<211> LENGTH: 398
<212> TYPE: PRT
<213> ORGANISM: Streptococcus mutans

<400> SEQUENCE: 7

Met Ala Lys Glu Lys Tyr Asp Arg Ser Lys Pro His Val Asn Ile Gly
1               5                   10                  15

Thr Ile Gly His Val Asp His Gly Lys Thr Thr Leu Thr Ala Ala Ile
            20                  25                  30

Thr Thr Val Leu Ala Arg Arg Leu Pro Ser Ala Val Asn Gln Pro Lys
            35                  40                  45

Asp Tyr Ser Ser Ile Asp Ala Ala Pro Glu Glu Arg Glu Arg Gly Ile
            50                  55                  60

Thr Ile Asn Thr Ala His Val Glu Tyr Glu Thr Glu Lys Arg His Tyr
65                  70                  75                  80

Ala His Ile Asp Ala Pro Gly His Ala Asp Tyr Val Lys Asn Met Ile
            85                  90                  95

Thr Gly Ala Ala Gln Met Asp Gly Ala Ile Leu Val Val Ala Ser Thr
            100                 105                 110

Asp Gly Pro Met Pro Gln Thr Arg Glu His Ile Leu Leu Ser Arg Gln
            115                 120                 125
```

```
Val Gly Val Lys Tyr Leu Ile Val Phe Met Asn Lys Val Asp Leu Val
            130                 135                 140
Asp Asp Glu Glu Leu Leu Glu Leu Val Glu Met Glu Ile Arg Asp Leu
145                 150                 155                 160
Leu Ser Glu Tyr Asp Phe Pro Gly Asp Ile Pro Val Ile Gln Gly
                165                 170                 175
Ser Ala Leu Lys Ala Leu Glu Gly Asp Thr Ala Gln Glu Asp Ile Ile
                180                 185                 190
Met Glu Leu Met His Thr Val Asp Asp Tyr Ile Pro Asp Pro Glu Arg
                195                 200                 205
Asp Thr Asp Lys Pro Leu Leu Leu Pro Val Glu Asp Val Phe Ser Ile
210                 215                 220
Thr Gly Arg Gly Thr Val Ala Ser Gly Arg Ile Asp Arg Gly Thr Val
225                 230                 235                 240
Lys Val Asn Asp Glu Val Glu Ile Val Gly Ile Arg Asp Asp Ile Gln
                245                 250                 255
Lys Ala Val Val Thr Gly Val Glu Met Phe Arg Lys Gln Leu Asp Glu
                260                 265                 270
Gly Ile Ala Gly Asp Asn Val Gly Val Leu Leu Arg Gly Ile Gln Arg
                275                 280                 285
Asp Glu Ile Glu Arg Gly Gln Val Leu Ala Lys Pro Gly Ser Ile His
                290                 295                 300
Pro His Thr Lys Phe Lys Gly Glu Val Tyr Ile Leu Thr Lys Glu Glu
305                 310                 315                 320
Gly Gly Arg His Thr Pro Phe Phe Asn Asn Tyr Arg Pro Gln Phe Tyr
                325                 330                 335
Phe Arg Thr Thr Asp Val Thr Gly Ser Ile Glu Leu Pro Ala Gly Thr
                340                 345                 350
Glu Met Val Met Pro Gly Asp Asn Val Thr Ile Asp Val Glu Leu Ile
                355                 360                 365
His Pro Ile Ala Val Glu Gln Gly Thr Thr Phe Ser Ile Arg Glu Gly
                370                 375                 380
Gly Arg Thr Val Gly Ser Gly Ile Val Ser Glu Ile Glu Ala
385                 390                 395

<210> SEQ ID NO 8
<211> LENGTH: 400
<212> TYPE: PRT
<213> ORGANISM: Streptococcus pneumoniae

<400> SEQUENCE: 8

Met Asn Glu Phe Glu Asp Leu Leu Asn Ser Val Ser Gln Val Glu Thr
1               5                   10                  15
Gly Asp Val Val Ser Ala Glu Val Leu Thr Val Asp Ala Thr Gln Ala
                20                  25                  30
Asn Val Ala Ile Ser Gly Thr Gly Val Glu Gly Val Leu Thr Leu Arg
                35                  40                  45
Glu Leu Thr Asn Asp Arg Asp Ala Asp Ile Asn Asp Phe Val Lys Val
                50                  55                  60
Gly Glu Val Leu Asp Val Val Leu Arg Gln Val Gly Lys Asp
65                  70                  75                  80
Thr Asp Thr Val Thr Tyr Leu Val Ser Lys Lys Arg Leu Glu Ala Arg
                85                  90                  95
Lys Ala Trp Asp Lys Leu Val Gly Arg Glu Glu Glu Val Val Thr Val
```

```
            100                 105                 110
Lys Gly Thr Arg Ala Val Lys Gly Gly Leu Ser Val Glu Phe Glu Gly
            115                 120                 125

Val Arg Gly Phe Ile Pro Ala Ser Met Leu Asp Thr Arg Phe Val Arg
        130                 135                 140

Asn Ala Glu Arg Phe Val Gly Gln Glu Phe Asp Thr Lys Ile Lys Glu
145                 150                 155                 160

Val Asn Ala Lys Glu Asn Arg Phe Ile Leu Ser Arg Arg Glu Val Val
            165                 170                 175

Glu Ala Ala Thr Ala Ala Arg Ala Glu Val Phe Gly Lys Leu Ala
        180                 185                 190

Val Gly Asp Val Val Thr Gly Lys Val Ala Arg Ile Thr Ser Phe Gly
            195                 200                 205

Ala Phe Ile Asp Leu Gly Gly Val Asp Gly Leu Val His Leu Thr Glu
        210                 215                 220

Leu Ser His Glu Arg Asn Val Ser Pro Lys Ser Val Thr Val Gly
225                 230                 235                 240

Glu Glu Ile Glu Val Lys Ile Leu Asp Leu Asn Glu Glu Gly Arg
            245                 250                 255

Val Ser Leu Ser Leu Lys Ala Thr Val Pro Gly Pro Trp Asp Gly Val
        260                 265                 270

Glu Gln Lys Leu Ala Lys Gly Asp Val Val Glu Gly Thr Val Lys Arg
            275                 280                 285

Leu Thr Asp Phe Gly Ala Phe Val Glu Val Leu Pro Gly Ile Asp Gly
        290                 295                 300

Leu Val His Val Ser Gln Ile Ser His Lys Arg Ile Glu Asn Pro Lys
305                 310                 315                 320

Glu Ala Leu Lys Val Gly Gln Glu Val Gln Val Lys Val Leu Glu Val
            325                 330                 335

Asn Ala Asp Ala Glu Arg Val Ser Leu Ser Ile Lys Ala Leu Glu Glu
        340                 345                 350

Arg Pro Ala Gln Glu Glu Gly Gln Lys Glu Lys Arg Ala Ala Arg
            355                 360                 365

Pro Arg Arg Pro Arg Arg Gln Glu Lys Arg Asp Phe Glu Leu Pro Glu
        370                 375                 380

Thr Gln Thr Gly Phe Ser Met Ala Asp Leu Phe Gly Asp Ile Glu Leu
385                 390                 395                 400

<210> SEQ ID NO 9
<211> LENGTH: 401
<212> TYPE: PRT
<213> ORGANISM: Streptococcus gordonii

<400> SEQUENCE: 9

Met Asn Glu Phe Glu Asp Leu Leu Asn Ser Val Ser Gln Val Glu Pro
1               5                   10                  15

Gly Asp Val Val Thr Ala Glu Val Leu Thr Val Asp Ala Asn Gln Ala
            20                  25                  30

Asn Val Ala Ile Ser Gly Thr Gly Val Glu Gly Val Leu Thr Leu Arg
        35                  40                  45

Glu Leu Thr Asn Asp Arg Asp Ala Asp Ile Asn Asp Leu Val Lys Thr
    50                  55                  60

Gly Glu Thr Leu Glu Leu Leu Val Leu Arg Gln Val Val Gly Lys Asp
65                  70                  75                  80
```

```
Thr Asp Thr Val Thr Tyr Leu Val Ser Lys Lys Arg Leu Glu Ala Arg
                85                  90                  95

Lys Ala Trp Asp Lys Leu Val Gly Arg Glu Glu Val Val Thr Val
            100                 105                 110

Lys Gly Thr Arg Ala Val Lys Gly Gly Leu Ser Val Glu Phe Glu Gly
            115                 120                 125

Leu Arg Gly Phe Ile Pro Ala Ser Met Leu Asp Thr Arg Phe Val Arg
130                 135                 140

Asn Thr Glu Arg Phe Val Gly Gln Glu Phe Asp Ala Lys Ile Lys Glu
145                 150                 155                 160

Val Asp Pro Lys Glu Asn Arg Phe Ile Leu Ser Arg Arg Glu Val Val
                165                 170                 175

Glu Ala Glu Ala Ala Thr Ala Arg Ala Glu Val Phe Gly Lys Leu Asn
            180                 185                 190

Val Gly Asp Val Val Thr Gly Lys Val Ala Arg Ile Thr Ser Phe Gly
            195                 200                 205

Ala Phe Ile Asp Leu Gly Gly Val Asp Gly Leu Val His Leu Thr Glu
210                 215                 220

Leu Ser His Glu Arg Asn Val Ser Pro Lys Ser Val Val Thr Val Gly
225                 230                 235                 240

Glu Glu Ile Glu Val Lys Val Leu Asp Leu Asn Glu Glu Gly Arg
                245                 250                 255

Val Ser Leu Ser Leu Lys Ala Thr Thr Pro Gly Pro Trp Asp Gly Val
                260                 265                 270

Glu Gln Lys Leu Ala Ala Gly Asp Val Ile Glu Gly Thr Val Lys Arg
            275                 280                 285

Leu Thr Asp Phe Gly Ala Phe Val Glu Val Leu Pro Gly Ile Asp Gly
290                 295                 300

Leu Val His Ile Ser Gln Ile Ser His Lys Arg Val Glu Asn Pro Lys
305                 310                 315                 320

Asp Val Leu Ser Val Gly Gln Glu Val Thr Val Lys Val Leu Glu Val
                325                 330                 335

Asn Pro Ala Asn Glu Arg Val Ser Leu Ser Ile Lys Ala Leu Glu Glu
            340                 345                 350

Arg Pro Ala Gln Glu Glu Gly Gln Lys Glu Lys Arg Gln Ser
            355                 360                 365

Arg Pro Arg Arg Pro Lys Arg Gln Glu Lys Arg Asp Phe Glu Leu Pro
            370                 375                 380

Glu Thr Gln Thr Gly Phe Ser Met Ala Asp Leu Phe Gly Asp Ile Glu
385                 390                 395                 400

Leu

<210> SEQ ID NO 10
<211> LENGTH: 449
<212> TYPE: PRT
<213> ORGANISM: Streptococcus pneumoniae

<400> SEQUENCE: 10

Met Ser His Ile Lys Phe Asp Tyr Ser Lys Val Leu Asp Lys Phe Val
1               5                   10                  15

Ala Pro His Glu Val Glu Tyr Met Gln Ser Gln Val Thr Ala Ala Asp
                20                  25                  30

Glu Leu Ile Arg Lys Gly Thr Gly Ala Gly Ser Asp Phe Leu Gly Trp
            35                  40                  45
```

-continued

```
Leu Asp Leu Pro Glu Lys Tyr Asp Arg Glu Phe Asp Arg Ile Leu
 50                 55                  60

Lys Ala Ala Glu Gln Ile Lys Ser Asp Ser Asp Val Leu Val Ile
 65                 70                  75                  80

Gly Ile Gly Gly Ser Tyr Leu Gly Ala Lys Ala Ile Asp Phe Leu
                 85                  90                  95

Asn His His Phe Ala Asn Leu Gln Thr Lys Glu Glu Arg Lys Ala Pro
             100                 105                 110

Gln Ile Leu Tyr Ala Gly Asn Ser Ile Ser Ser Thr Tyr Leu Ala Asp
             115                 120                 125

Leu Val Glu Tyr Val Ala Asp Lys Asp Phe Ser Val Asn Val Ile Ser
 130                 135                 140

Lys Ser Gly Thr Thr Thr Glu Pro Ala Ile Ala Phe Arg Val Phe Lys
 145                 150                 155                 160

Glu Leu Leu Val Lys Lys Tyr Gly Gln Glu Glu Ala Asn Lys Arg Ile
                 165                 170                 175

Tyr Ala Thr Thr Asp Arg Gln Lys Gly Ala Val Lys Val Glu Ala Asp
             180                 185                 190

Ala Asn Gly Trp Gly Thr Phe Val Pro Asp Asp Ile Gly Gly Arg
             195                 200                 205

Phe Ser Val Leu Thr Ala Val Gly Leu Leu Pro Ile Ala Ala Ser Gly
 210                 215                 220

Ala Asp Ile Lys Ala Leu Met Glu Gly Ala Asn Ala Ala Arg Lys Asp
 225                 230                 235                 240

Tyr Thr Ser Asp Lys Ile Ser Glu Asn Glu Ala Tyr Gln Tyr Ala Ala
                 245                 250                 255

Val Arg Asn Ile Leu Tyr Arg Lys Gly Tyr Ala Thr Glu Ile Leu Val
             260                 265                 270

Asn Tyr Glu Pro Ser Leu Gln Tyr Phe Ser Glu Trp Trp Lys Gln Leu
             275                 280                 285

Ala Gly Glu Ser Glu Gly Lys Asp Gln Lys Gly Ile Tyr Pro Thr Ser
 290                 295                 300

Ala Asn Phe Ser Thr Asp Leu His Ser Leu Gly Gln Phe Ile Gln Glu
305                 310                 315                 320

Gly Thr Arg Ile Met Phe Glu Thr Val Val Arg Val Asp Lys Pro Arg
                 325                 330                 335

Lys Asn Val Leu Ile Pro Thr Leu Glu Glu Asp Leu Asp Gly Leu Gly
             340                 345                 350

Tyr Leu Gln Gly Lys Asp Val Asp Phe Val Asn Lys Lys Ala Thr Asp
             355                 360                 365

Gly Val Leu Leu Ala His Thr Asp Gly Asp Val Pro Asn Met Tyr Val
 370                 375                 380

Thr Leu Pro Glu Gln Asp Ala Phe Thr Leu Gly Tyr Thr Ile Tyr Phe
385                 390                 395                 400

Phe Glu Leu Ala Ile Ala Leu Ser Gly Tyr Leu Asn Ala Ile Asn Pro
                 405                 410                 415

Phe Asp Gln Pro Gly Val Glu Ala Tyr Lys Arg Asn Met Phe Ala Leu
             420                 425                 430

Leu Gly Lys Pro Gly Phe Glu Glu Leu Ser Lys Glu Leu Asn Ala Arg
             435                 440                 445

Leu

<210> SEQ ID NO 11
```

<211> LENGTH: 449
<212> TYPE: PRT
<213> ORGANISM: Streptococcus gordonii

<400> SEQUENCE: 11

Met Pro His Ile Lys Phe Asp Tyr Ser Lys Val Leu Asp Lys Phe Val
1               5                   10                  15

Ala Pro His Glu Val Glu Tyr Met Gln Ser Gln Val Thr Ala Ala Asp
            20                  25                  30

Glu Leu Ile Arg Lys Gly Thr Gly Ala Gly Ser Asp Phe Leu Gly Trp
        35                  40                  45

Leu Asp Leu Pro Glu Asn Tyr Asp Arg Glu Phe Asp Arg Ile Leu
    50                  55                  60

Lys Ala Ala Glu Gln Ile Lys Ser Asp Ser Asp Val Leu Val Val Ile
65                  70                  75                  80

Gly Ile Gly Gly Ser Tyr Leu Gly Ala Lys Ala Ala Ile Asp Phe Leu
                85                  90                  95

Asn His His Phe Ala Asn Leu Gln Thr Lys Glu Glu Arg Lys Ala Pro
            100                 105                 110

Gln Ile Leu Tyr Ala Gly Asn Ser Ile Ser Ser Thr Tyr Leu Ala Asp
        115                 120                 125

Leu Val Glu Tyr Val Ala Asp Lys Asp Phe Ser Val Asn Val Ile Ser
    130                 135                 140

Lys Ser Gly Thr Thr Thr Glu Pro Ala Ile Ala Phe Arg Val Phe Lys
145                 150                 155                 160

Glu Leu Leu Val Lys Lys Tyr Gly Gln Glu Glu Ala Asn Lys Arg Ile
                165                 170                 175

Tyr Ala Thr Thr Asp Arg Gln Lys Gly Ala Val Lys Val Glu Ala Asp
            180                 185                 190

Ala Asn Gly Trp Glu Thr Phe Val Val Pro Asp Asp Ile Gly Gly Arg
        195                 200                 205

Phe Ser Val Leu Thr Ala Val Gly Leu Leu Pro Ile Ala Ala Ser Gly
    210                 215                 220

Ala Asp Ile Lys Ala Leu Met Glu Gly Ala Asn Ala Ala Arg Lys Asp
225                 230                 235                 240

Tyr Thr Ser Asp Lys Leu Ser Glu Asn Glu Ala Tyr Gln Tyr Ala Ala
                245                 250                 255

Val Arg Asn Ile Leu Tyr Arg Lys Gly Tyr Ala Thr Glu Ile Leu Val
            260                 265                 270

Asn Tyr Glu Pro Ser Leu Gln Tyr Phe Ser Glu Trp Trp Lys Gln Leu
        275                 280                 285

Ala Gly Glu Ser Glu Gly Lys Asp Gln Lys Gly Ile Tyr Pro Thr Ser
    290                 295                 300

Ala Asn Phe Ser Thr Asp Leu His Ser Leu Gly Gln Phe Ile Gln Glu
305                 310                 315                 320

Gly Thr Arg Ile Met Phe Glu Thr Val Val Arg Val Asp Lys Pro Arg
                325                 330                 335

Lys Asn Val Ile Ile Pro Thr Leu Glu Glu Asp Leu Asp Gly Leu Gly
            340                 345                 350

Tyr Leu Gln Gly Lys Asp Val Asp Phe Val Asn Lys Lys Ala Thr Asp
        355                 360                 365

Gly Val Leu Leu Ala His Thr Asp Gly Asp Val Pro Asn Met Tyr Val
    370                 375                 380

Thr Leu Pro Glu Gln Asp Ala Phe Thr Leu Gly Tyr Thr Ile Tyr Phe

```
                385                 390                 395                 400
Phe Glu Leu Ala Ile Ala Leu Ser Gly Tyr Leu Asn Ala Ile Asn Pro
                    405                 410                 415

Phe Asp Gln Pro Gly Val Glu Ala Tyr Lys Arg Asn Met Phe Ala Leu
                420                 425                 430

Leu Gly Lys Pro Gly Phe Glu Leu Ser Lys Glu Leu Asn Ala Arg
                435                 440                 445

Leu

<210> SEQ ID NO 12
<211> LENGTH: 449
<212> TYPE: PRT
<213> ORGANISM: Streptococcus pyogenes

<400> SEQUENCE: 12

Met Ser His Ile Thr Phe Asp Tyr Ser Lys Val Leu Glu Ser Phe Ala
1               5                   10                  15

Gly Gln His Glu Ile Asp Phe Leu Gln Gly Gln Val Thr Glu Ala Asp
                20                  25                  30

Lys Leu Leu Arg Glu Gly Thr Gly Pro Gly Ser Asp Phe Leu Gly Trp
            35                  40                  45

Leu Asp Leu Pro Glu Asn Tyr Asp Lys Asp Glu Phe Ala Arg Ile Leu
50                  55                  60

Thr Ala Ala Glu Lys Ile Lys Ser Asp Ser Glu Val Leu Val Val Ile
65                  70                  75                  80

Gly Ile Gly Gly Ser Tyr Leu Gly Ala Lys Ala Ala Ile Asp Phe Leu
                85                  90                  95

Asn His His Phe Ala Asn Leu Gln Thr Ala Lys Glu Arg Lys Ala Pro
                100                 105                 110

Gln Ile Leu Tyr Ala Gly Asn Ser Ile Ser Ser Thr Tyr Leu Ala Asp
            115                 120                 125

Leu Val Glu Tyr Val Gln Asp Lys Glu Phe Ser Val Asn Val Ile Ser
        130                 135                 140

Lys Ser Gly Thr Thr Thr Glu Pro Ala Ile Ala Phe Arg Val Phe Lys
145                 150                 155                 160

Glu Leu Leu Val Lys Lys Tyr Gly Gln Glu Glu Ala Asn Lys Arg Ile
                165                 170                 175

Tyr Ala Thr Thr Asp Lys Val Lys Gly Ala Val Lys Val Glu Ala Asp
                180                 185                 190

Ala Asn Asn Trp Glu Thr Phe Val Val Pro Asp Asn Val Gly Gly Arg
            195                 200                 205

Phe Ser Val Leu Thr Ala Val Gly Leu Leu Pro Ile Ala Ala Ser Gly
        210                 215                 220

Ala Asp Ile Thr Ala Leu Met Glu Gly Ala Asn Ala Ala Arg Lys Asp
225                 230                 235                 240

Leu Ser Ser Asp Lys Ile Ser Glu Asn Ile Ala Tyr Gln Tyr Ala Ala
                245                 250                 255

Val Arg Asn Val Leu Tyr Arg Lys Gly Tyr Ile Thr Glu Ile Leu Ala
                260                 265                 270

Asn Tyr Glu Pro Ser Leu Gln Tyr Phe Gly Glu Trp Trp Lys Gln Leu
            275                 280                 285

Ala Gly Glu Ser Glu Gly Lys Asp Gln Lys Gly Ile Tyr Pro Thr Ser
        290                 295                 300

Ala Asn Phe Ser Thr Asp Leu His Ser Leu Gly Gln Phe Ile Gln Glu
```

```
                305                 310                 315                 320
Gly Tyr Arg Asn Leu Phe Glu Thr Val Ile Arg Val Asp Lys Pro Arg
                    325                 330                 335

Lys Asn Val Ile Ile Pro Glu Leu Ala Glu Asp Leu Asp Gly Leu Gly
                    340                 345                 350

Tyr Leu Gln Gly Lys Asp Val Asp Phe Val Asn Lys Lys Ala Thr Asp
                    355                 360                 365

Gly Val Leu Leu Ala His Thr Asp Gly Gly Val Pro Asn Met Phe Val
370                 375                 380

Thr Leu Pro Ala Gln Asp Glu Phe Thr Leu Gly Tyr Thr Ile Tyr Phe
385                 390                 395                 400

Phe Glu Leu Ala Ile Ala Val Ser Gly Tyr Met Asn Ala Val Asn Pro
                    405                 410                 415

Phe Asp Gln Pro Gly Val Glu Ala Tyr Lys Arg Asn Met Phe Ala Leu
                    420                 425                 430

Leu Gly Lys Pro Gly Phe Glu Glu Leu Ser Ala Glu Leu Asn Ala Arg
                    435                 440                 445

Leu

<210> SEQ ID NO 13
<211> LENGTH: 419
<212> TYPE: PRT
<213> ORGANISM: Streptococcus pneumoniae

<400> SEQUENCE: 13

Met Thr Phe Ser Phe Asp Thr Ala Ala Gln Gly Ala Val Ile Lys
1               5                   10                  15

Val Ile Gly Val Gly Gly Gly Gly Asn Ala Ile Asn Arg Met Val
            20                  25                  30

Asp Glu Gly Val Thr Gly Val Glu Phe Ile Ala Ala Asn Thr Asp Val
            35                  40                  45

Gln Ala Leu Ser Ser Thr Lys Ala Glu Thr Val Ile Gln Leu Gly Pro
    50                  55                  60

Lys Leu Thr Arg Gly Leu Gly Ala Gly Gly Gln Pro Glu Val Gly Arg
65                  70                  75                  80

Lys Ala Ala Glu Glu Ser Glu Glu Thr Leu Thr Glu Ala Ile Ser Gly
                85                  90                  95

Ala Asp Met Val Phe Ile Thr Ala Gly Met Gly Gly Gly Ser Gly Thr
            100                 105                 110

Gly Ala Ala Pro Val Ile Ala Arg Ile Ala Lys Asp Leu Gly Ala Leu
            115                 120                 125

Thr Val Gly Val Val Thr Arg Pro Phe Gly Phe Glu Gly Ser Lys Arg
            130                 135                 140

Gly Gln Phe Ala Val Glu Gly Ile Asn Gln Leu Arg Glu His Val Asp
145                 150                 155                 160

Thr Leu Leu Ile Ile Ser Asn Asn Asn Leu Leu Glu Ile Val Asp Lys
                165                 170                 175

Lys Thr Pro Leu Leu Glu Ala Leu Ser Glu Ala Asp Asn Val Leu Arg
            180                 185                 190

Gln Gly Val Gln Gly Ile Thr Asp Leu Ile Thr Asn Pro Gly Leu Ile
            195                 200                 205

Asn Leu Asp Phe Ala Asp Val Lys Thr Val Met Ala Asn Lys Gly Asn
            210                 215                 220

Ala Leu Met Gly Ile Gly Ile Gly Ser Gly Glu Glu Arg Val Val Glu
```

```
            225                 230                 235                 240
Ala Ala Arg Lys Ala Ile Tyr Ser Pro Leu Leu Glu Thr Thr Ile Asp
                245                 250                 255

Gly Ala Glu Asp Val Ile Val Asn Val Thr Gly Gly Leu Asp Leu Thr
                260                 265                 270

Leu Ile Glu Ala Glu Ala Ser Gln Ile Val Asn Gln Ala Ala Gly
            275                 280                 285

Gln Gly Val Asn Ile Trp Leu Gly Thr Ser Ile Asp Glu Ser Met Arg
        290                 295                 300

Asp Glu Ile Arg Val Thr Val Ala Thr Gly Val Arg Gln Asp Arg
305                 310                 315                 320

Val Glu Lys Val Val Ala Pro Gln Ala Arg Ser Ala Thr Asn Tyr Arg
                325                 330                 335

Glu Thr Val Lys Pro Ala His Ser His Gly Phe Asp Arg His Phe Asp
                340                 345                 350

Met Ala Glu Thr Val Glu Leu Pro Lys Gln Asn Pro Arg Arg Leu Glu
            355                 360                 365

Pro Thr Gln Ala Ser Ala Phe Gly Asp Trp Asp Leu Arg Arg Glu Ser
        370                 375                 380

Ile Val Arg Thr Thr Asp Ser Val Val Ser Pro Val Glu Arg Phe Glu
385                 390                 395                 400

Ala Pro Ile Ser Gln Asp Glu Asp Glu Leu Asp Thr Pro Pro Phe Phe
                405                 410                 415

Lys Asn Arg

<210> SEQ ID NO 14
<211> LENGTH: 419
<212> TYPE: PRT
<213> ORGANISM: Streptococcus gordonii

<400> SEQUENCE: 14

Met Thr Phe Ser Phe Asp Thr Ala Ala Ala Gln Gly Ala Ile Ile Lys
1               5                   10                  15

Val Ile Gly Val Gly Gly Gly Gly Asn Ala Ile Asn Arg Met Ile
            20                  25                  30

Asp Glu Gly Val Ala Gly Val Glu Phe Ile Ala Ala Asn Thr Asp Val
                35                  40                  45

Gln Ala Leu Ser Ser Thr Lys Ala Glu Thr Val Ile Gln Leu Gly Pro
        50                  55                  60

Lys Leu Thr Arg Gly Leu Gly Ala Gly Gly Gln Pro Glu Val Gly Arg
65                  70                  75                  80

Lys Ala Ala Glu Glu Ser Glu Glu Val Leu Thr Glu Ala Leu Ser Gly
                85                  90                  95

Ala Asp Met Val Phe Ile Thr Ala Gly Met Gly Gly Gly Ser Gly Thr
            100                 105                 110

Gly Ala Ala Pro Val Ile Ala Arg Ile Ala Lys Gly Leu Gly Ala Leu
        115                 120                 125

Thr Val Ala Val Val Thr Arg Pro Phe Gly Phe Glu Gly Ser Lys Arg
130                 135                 140

Gly Asn Phe Ala Ile Glu Gly Ile Asn Glu Leu Arg Glu His Val Asp
145                 150                 155                 160

Thr Leu Leu Ile Ile Ser Asn Asn Asn Leu Leu Glu Ile Val Asp Lys
                165                 170                 175

Lys Thr Pro Leu Leu Glu Ala Leu Ser Glu Ala Asp Asn Val Leu Arg
```

```
            180                 185                 190
Gln Gly Val Gln Gly Ile Thr Asp Leu Ile Thr Ser Pro Gly Leu Ile
                195                 200                 205

Asn Leu Asp Phe Ala Asp Val Lys Thr Val Met Ala Asp Lys Gly Asn
            210                 215                 220

Ala Leu Met Gly Ile Gly Ile Gly Ser Gly Glu Arg Val Ile Glu
225                 230                 235                 240

Ala Ala Arg Lys Ala Ile Tyr Ser Pro Leu Leu Glu Thr Thr Ile Asp
                245                 250                 255

Gly Ala Glu Asp Val Ile Val Asn Val Thr Gly Gly Leu Asp Met Thr
            260                 265                 270

Leu Ile Glu Ala Glu Glu Ala Ser Glu Ile Val Asn Gln Ala Ala Gly
                275                 280                 285

His Gly Val Asn Ile Trp Leu Gly Thr Ser Ile Asp Glu Ser Met Arg
            290                 295                 300

Asp Glu Ile Arg Val Thr Val Ala Thr Gly Val Arg Gln Asp Arg
305                 310                 315                 320

Val Glu Lys Val Ser Gly Ile Arg Ser Pro Lys Arg Ser His Asn Glu
                325                 330                 335

Pro Val Arg Glu Thr Arg Ser His His Ser Tyr Asp Arg Asn Phe Asp
            340                 345                 350

Leu Thr Glu Thr Val Glu Ile Pro Lys Thr Thr Arg Gln Gln Pro Glu
            355                 360                 365

Lys Lys Gln Thr Ser Ala Phe Gly Glu Trp Asp Leu Arg Arg Asp Asn
            370                 375                 380

Ile Val Arg Glu Thr Gln Gly Gly Ser Lys Ser Ala Val Glu Arg Tyr
385                 390                 395                 400

Thr Asp Ser Ser Ser Asp Asp Asp Glu Leu Glu Thr Pro Pro Phe Phe
                405                 410                 415

Arg Asn Arg

<210> SEQ ID NO 15
<211> LENGTH: 468
<212> TYPE: PRT
<213> ORGANISM: Streptococcus pyogenes

<400> SEQUENCE: 15

Met Ser Ser Gly Lys Ile Ala Gln Val Val Gly Pro Val Val Asp Val
1               5                   10                  15

Met Phe Ala Ser Gly Asp Lys Leu Pro Glu Ile Asn Asn Ala Leu Ile
                20                  25                  30

Val Tyr Lys Asp Ser Asp Lys Lys Gln Lys Ile Val Leu Glu Val Ala
            35                  40                  45

Leu Glu Leu Gly Asp Gly Met Val Arg Thr Ile Ala Met Glu Ser Thr
        50                  55                  60

Asp Gly Leu Thr Arg Gly Leu Glu Val Leu Asp Thr Gly Arg Ala Ile
65              70                  75                  80

Ser Val Pro Val Gly Lys Glu Thr Leu Gly Arg Val Phe Asn Val Leu
                85                  90                  95

Gly Glu Thr Ile Asp Leu Glu Gly Pro Phe Ala Glu Asp Val Asp Arg
            100                 105                 110

Gln Pro Ile His Lys Lys Ala Pro Ser Phe Asp Glu Leu Ser Thr Ser
            115                 120                 125

Ser Glu Ile Leu Glu Thr Gly Ile Lys Val Ile Asp Leu Leu Ala Pro
```

```
            130                 135                 140
Tyr Leu Lys Gly Gly Lys Val Gly Leu Phe Gly Gly Ala Gly Val Gly
145                 150                 155                 160

Lys Thr Val Leu Ile Gln Glu Leu Ile His Asn Ile Ala Gln Glu His
                165                 170                 175

Gly Gly Ile Ser Val Phe Thr Gly Val Gly Glu Arg Thr Arg Glu Gly
            180                 185                 190

Asn Asp Leu Tyr Trp Glu Met Lys Glu Ser Gly Val Ile Glu Lys Thr
            195                 200                 205

Ala Met Val Phe Gly Gln Met Asn Glu Pro Pro Gly Ala Arg Met Arg
210                 215                 220

Val Ala Leu Thr Gly Leu Thr Ile Ala Glu Tyr Phe Arg Asp Val Glu
225                 230                 235                 240

Gly Gln Asp Val Leu Leu Phe Ile Asp Asn Ile Phe Arg Phe Thr Gln
                245                 250                 255

Ala Gly Ser Glu Val Ser Ala Leu Leu Gly Arg Met Pro Ser Ala Val
            260                 265                 270

Gly Tyr Gln Pro Thr Leu Ala Thr Glu Met Gly Gln Leu Gln Glu Arg
            275                 280                 285

Ile Thr Ser Thr Gln Lys Gly Ser Val Thr Ser Ile Gln Ala Ile Tyr
            290                 295                 300

Val Pro Ala Asp Asp Tyr Thr Asp Pro Ala Pro Ala Thr Ala Phe Ala
305                 310                 315                 320

His Leu Asp Ser Thr Thr Asn Leu Glu Arg Lys Leu Thr Gln Met Gly
                325                 330                 335

Ile Tyr Pro Ala Val Asp Pro Leu Ala Ser Ser Arg Ala Leu Ser
            340                 345                 350

Pro Glu Ile Val Gly Glu His Tyr Ala Val Ala Thr Glu Val Gln
            355                 360                 365

Arg Val Leu Gln Arg Tyr Arg Glu Leu Gln Asp Ile Ile Ala Ile Leu
370                 375                 380

Gly Met Asp Glu Leu Ser Asp Glu Glu Lys Thr Leu Val Gly Arg Ala
385                 390                 395                 400

Arg Arg Ile Gln Phe Phe Leu Ser Gln Asn Phe Asn Val Ala Glu Gln
                405                 410                 415

Phe Thr Gly Leu Pro Gly Ser Tyr Val Pro Val Ala Glu Thr Val Arg
            420                 425                 430

Gly Phe Lys Glu Ile Leu Glu Gly Lys Tyr Asp Asp Leu Pro Glu Asp
            435                 440                 445

Ala Phe Arg Ser Val Gly Pro Ile Glu Asp Val Ile Lys Lys Ala Glu
450                 455                 460

Lys Met Gly Phe
465

<210> SEQ ID NO 16
<211> LENGTH: 468
<212> TYPE: PRT
<213> ORGANISM: Streptococcus gordonii

<400> SEQUENCE: 16

Met Ser Ser Gly Lys Ile Thr Gln Val Ile Gly Pro Val Val Asp Val
1               5                   10                  15

Ala Phe Ala Gly Asp Arg Leu Pro Glu Ile Asn Asn Ala Leu Val
            20                  25                  30
```

```
Val Tyr Lys Asn Asp Glu Lys Lys Ser Lys Ile Val Leu Glu Val Ala
         35                  40                  45
Leu Glu Leu Gly Asp Gly Val Val Arg Thr Ile Ala Met Glu Ser Thr
 50                  55                  60
Asp Gly Leu Thr Arg Gly Leu Glu Val Leu Asp Thr Gly Arg Pro Ile
 65                  70                  75                  80
Ser Val Pro Val Gly Lys Glu Thr Leu Gly Arg Val Phe Asn Val Leu
                 85                  90                  95
Gly Asp Thr Ile Asp Leu Asp Ala Pro Phe Gly Asp Ala Glu Arg
             100                 105                 110
Gln Pro Ile His Lys Lys Ala Pro Thr Phe Asp Glu Leu Ser Thr Ser
             115                 120                 125
Ser Glu Ile Leu Glu Thr Gly Ile Lys Val Ile Asp Leu Leu Ala Pro
 130                 135                 140
Tyr Leu Lys Gly Gly Lys Val Gly Leu Phe Gly Ala Gly Val Gly
 145                 150                 155                 160
Lys Thr Val Leu Ile Gln Glu Leu Ile His Asn Ile Ala Gln Glu His
                 165                 170                 175
Gly Gly Ile Ser Val Phe Thr Gly Val Gly Glu Arg Thr Arg Glu Gly
             180                 185                 190
Asn Asp Leu Tyr Trp Glu Met Lys Glu Ser Gly Val Ile Glu Lys Thr
             195                 200                 205
Ala Met Val Phe Gly Gln Met Asn Glu Pro Pro Gly Ala Arg Met Arg
 210                 215                 220
Val Ala Leu Thr Gly Leu Thr Ile Ala Glu Tyr Phe Arg Asp Val Glu
 225                 230                 235                 240
Gly Gln Asp Val Leu Leu Phe Ile Asp Asn Ile Phe Arg Phe Thr Gln
                 245                 250                 255
Ala Gly Ser Glu Val Ser Ala Leu Leu Gly Arg Met Pro Ser Ala Val
             260                 265                 270
Gly Tyr Gln Pro Thr Leu Ala Thr Glu Met Gly Gln Leu Gln Glu Arg
             275                 280                 285
Ile Thr Ser Thr Lys Lys Gly Ser Val Thr Ser Ile Gln Ala Ile Tyr
 290                 295                 300
Val Pro Ala Asp Asp Tyr Thr Asp Pro Ala Pro Ala Thr Ala Phe Ala
 305                 310                 315                 320
His Leu Asp Ser Thr Thr Asn Leu Glu Arg Lys Leu Val Gln Leu Gly
                 325                 330                 335
Ile Tyr Pro Ala Val Asp Pro Leu Ala Ser Ser Arg Ala Leu Ala
             340                 345                 350
Pro Glu Ile Val Gly Glu Glu His Tyr Ala Val Ala Glu Val Lys
             355                 360                 365
Arg Val Leu Gln Arg Tyr His Glu Leu Gln Asp Ile Ala Ile Leu
 370                 375                 380
Gly Met Asp Glu Leu Ser Asp Glu Glu Lys Thr Leu Val Ala Arg Ala
 385                 390                 395                 400
Arg Arg Ile Gln Phe Phe Leu Ser Gln Asn Phe Asn Val Ala Glu Gln
                 405                 410                 415
Phe Thr Gly Gln Pro Gly Ser Tyr Val Pro Val Ala Glu Thr Val Arg
             420                 425                 430
Gly Phe Lys Glu Ile Leu Glu Gly Lys His Asp Lys Leu Pro Glu Asp
             435                 440                 445
Ala Phe Arg Gly Val Gly Ser Ile Glu Asp Val Leu Ala Lys Ala Glu
```

450                 455                 460

Lys Met Gly Phe
465

<210> SEQ ID NO 17
<211> LENGTH: 474
<212> TYPE: PRT
<213> ORGANISM: Streptococcus gordonii

<400> SEQUENCE: 17

Met Thr Lys Ala Asn Phe Gly Val Val Gly Met Ala Val Met Gly Arg
1               5                   10                  15

Asn Leu Ala Leu Asn Ile Glu Ser Arg Gly Tyr Thr Val Ala Ile Tyr
            20                  25                  30

Asn Arg Ser Ala Asn Lys Thr Glu Asp Val Ile Ala Cys His Pro Glu
        35                  40                  45

Lys Asn Phe Val Pro Ser Tyr Asp Val Glu Ser Phe Val Asn Ser Ile
    50                  55                  60

Glu Lys Pro Arg Arg Ile Met Leu Met Val Gln Ala Gly Pro Gly Thr
65                  70                  75                  80

Asp Ala Thr Ile Gln Ala Leu Leu Pro His Leu Asp Lys Gly Asp Ile
                85                  90                  95

Leu Ile Asp Gly Gly Asn Thr Phe Tyr Lys Asp Thr Ile Arg Arg Asn
            100                 105                 110

Glu Glu Leu Ala Asn Ser Gly Ile Asn Phe Ile Gly Thr Gly Val Ser
        115                 120                 125

Gly Gly Glu Lys Gly Ala Leu Glu Gly Pro Ser Ile Met Pro Gly Gly
    130                 135                 140

Gln Lys Glu Ala Tyr Glu Leu Val Ala Asp Val Leu Glu Glu Ile Ser
145                 150                 155                 160

Ala Lys Ala Pro Glu Asp Gly Lys Pro Cys Val Thr Tyr Ile Gly Pro
                165                 170                 175

Asp Gly Ala Gly His Tyr Val Lys Met Val His Asn Gly Ile Glu Tyr
            180                 185                 190

Gly Asp Met Gln Leu Ile Ala Glu Ser Tyr Asp Leu Met Gln His Leu
        195                 200                 205

Leu Gly Leu Ser Ala Glu Asp Met Ala Glu Ile Phe Thr Glu Trp Asn
    210                 215                 220

Lys Gly Glu Leu Asp Ser Tyr Leu Ile Glu Ile Thr Ala Asp Ile Leu
225                 230                 235                 240

Ser Arg Lys Asp Asp Glu Gly Gln Asp Gly Pro Ile Val Asp Tyr Ile
                245                 250                 255

Leu Asp Ala Ala Gly Asn Lys Gly Thr Gly Lys Trp Thr Ser Gln Ser
            260                 265                 270

Ala Leu Asp Leu Gly Val Pro Leu Ser Leu Ile Thr Glu Ser Val Phe
        275                 280                 285

Ala Arg Tyr Ile Ser Ala Tyr Lys Glu Glu Arg His Ala Ser Lys
    290                 295                 300

Val Leu Pro Lys Pro Ala Thr Phe Lys Phe Glu Gly Asp Lys Ala Glu
305                 310                 315                 320

Leu Ile Glu Lys Ile Arg Gln Ala Leu Tyr Phe Ser Lys Ile Ile Ser
                325                 330                 335

Tyr Ala Gln Gly Phe Ala Gln Leu Arg Val Ala Ser Lys Glu Asn Asn
            340                 345                 350

```
Trp Asn Leu Pro Phe Ala Asp Ile Ala Ser Ile Trp Arg Asp Gly Cys
            355                 360                 365

Ile Ile Arg Ser Arg Phe Leu Gln Lys Ile Thr Asp Ala Tyr Asn Arg
370                 375                 380

Asp Ala Asp Leu Ala Asn Leu Leu Leu Asp Glu Tyr Phe Leu Asp Val
385                 390                 395                 400

Thr Ala Lys Tyr Gln Gln Ser Val Arg Asp Ile Val Ala Leu Ala Val
                405                 410                 415

Gln Ala Gly Val Pro Val Pro Thr Phe Ser Ala Ala Ile Thr Tyr Phe
            420                 425                 430

Asp Ser Tyr Arg Ser Ala Asp Leu Pro Ala Asn Leu Ile Gln Ala Gln
                435                 440                 445

Arg Asp Tyr Phe Gly Ala His Thr Tyr Gln Arg Lys Asp Lys Glu Gly
450                 455                 460

Thr Phe His Tyr Ser Trp Tyr Asp Glu Lys
465                 470

<210> SEQ ID NO 18
<211> LENGTH: 444
<212> TYPE: PRT
<213> ORGANISM: Streptococcus pneumoniae

<400> SEQUENCE: 18

Met Asn Ala Ile Gln Glu Ser Phe Thr Asp Lys Leu Phe Ala Asn Tyr
1               5                   10                  15

Glu Ala Asn Val Lys Tyr Gln Ala Ile Glu Asn Ala Ala Ser His Asn
                20                  25                  30

Gly Ile Phe Ala Ala Leu Glu Arg Arg Gln Ser His Val Asp Asn Thr
            35                  40                  45

Pro Val Phe Ser Leu Asp Leu Thr Lys Asp Lys Val Thr Asn Gln Lys
        50                  55                  60

Ala Ser Gly Arg Cys Trp Met Phe Ala Ala Leu Asn Thr Phe Arg His
65                  70                  75                  80

Lys Leu Ile Ser Gln Tyr Lys Leu Glu Asn Phe Glu Leu Ser Gln Ala
                85                  90                  95

His Thr Phe Phe Trp Asp Lys Tyr Glu Lys Ser Asn Trp Phe Leu Glu
            100                 105                 110

Gln Val Ile Ala Thr Ser Asp Gln Glu Leu Thr Ser Arg Lys Val Ser
        115                 120                 125

Phe Leu Leu Gln Thr Pro Gln Gln Asp Gly Gly Gln Trp Asp Met Val
    130                 135                 140

Val Ser Leu Phe Glu Lys Tyr Gly Val Val Pro Lys Ser Val Tyr Pro
145                 150                 155                 160

Glu Ser Val Ser Ser Ser Ser Arg Glu Leu Asn Ala Ile Leu Asn
                165                 170                 175

Lys Leu Leu Arg Gln Asp Ala Gln Ile Leu Arg Asp Leu Leu Val Ser
            180                 185                 190

Gly Ala Asp Gln Ala Thr Val Gln Ala Lys Lys Glu Asp Leu Leu Gln
        195                 200                 205

Glu Ile Phe Asn Phe Leu Ala Met Ser Leu Gly Leu Pro Pro Arg Lys
    210                 215                 220

Phe Asp Phe Ala Tyr Arg Asp Lys Asp Asn Asn Tyr Lys Ser Glu Lys
225                 230                 235                 240

Gly Ile Thr Pro Gln Glu Phe Tyr Lys Lys Tyr Val Asn Leu Pro Leu
                245                 250                 255
```

```
Glu Asp Tyr Val Ser Val Ile Asn Ala Pro Thr Ala Asp Lys Pro Tyr
            260                 265                 270

Gly Lys Ser Tyr Thr Val Glu Met Leu Gly Asn Val Gly Ser Arg
            275                 280                 285

Ala Val Arg Tyr Ile Asn Val Pro Met Glu Arg Leu Lys Glu Leu Ala
290                 295                 300

Ile Ala Gln Met Gln Ala Gly Glu Thr Val Trp Phe Gly Ser Asp Val
305                 310                 315                 320

Gly Gln Leu Ser Asn Arg Lys Ala Gly Ile Leu Ala Thr Asp Val Tyr
                325                 330                 335

Asp Phe Glu Ser Ser Met Asp Ile Lys Leu Thr Gln Asp Lys Ala Gly
            340                 345                 350

Arg Leu Asp Tyr Ser Glu Ser Leu Met Thr His Ala Met Val Leu Thr
            355                 360                 365

Gly Val Asp Leu Asp Glu Asn Gly Lys Ser Thr Lys Trp Lys Val Glu
            370                 375                 380

Asn Ser Trp Gly Asp Lys Val Gly Thr Asp Gly Tyr Phe Val Ala Ser
385                 390                 395                 400

Asp Ala Trp Met Asp Glu Tyr Thr Tyr Gln Ile Val Val Arg Lys Glu
                405                 410                 415

Leu Leu Thr Ala Glu Glu Gln Ala Ala Tyr Gly Ala Glu Pro Ile Val
            420                 425                 430

Leu Ala Pro Trp Asp Pro Met Gly Ala Leu Ala Glu
            435                 440

<210> SEQ ID NO 19
<211> LENGTH: 172
<212> TYPE: PRT
<213> ORGANISM: Streptococcus pneumoniae

<400> SEQUENCE: 19

Met Val Glu Leu Lys Lys Glu Ala Val Lys Asp Val Thr Ser Leu Thr
1               5                   10                  15

Lys Ala Ala Pro Val Ala Leu Ala Lys Thr Lys Glu Val Leu Asn Gln
            20                  25                  30

Ala Val Ala Asp Leu Tyr Val Ala His Val Ala Leu His Gln Val His
        35                  40                  45

Trp Tyr Met His Gly Arg Gly Phe Leu Val Trp His Pro Lys Met Asp
    50                  55                  60

Glu Tyr Met Glu Ala Leu Asp Gly Gln Leu Asp Glu Ile Ser Glu Arg
65                  70                  75                  80

Leu Ile Thr Leu Gly Gly Ser Pro Phe Ser Thr Leu Thr Glu Phe Leu
                85                  90                  95

Gln Asn Ser Glu Ile Glu Glu Glu Ala Gly Glu Tyr Arg Asn Val Glu
            100                 105                 110

Glu Ser Leu Glu Arg Val Leu Val Ile Tyr Arg Tyr Leu Ser Glu Leu
        115                 120                 125

Phe Gln Lys Gly Leu Asp Val Thr Asp Glu Gly Asp Asp Val Thr
    130                 135                 140

Asn Gly Ile Phe Ala Gly Ala Lys Thr Glu Thr Asp Lys Thr Ile Trp
145                 150                 155                 160

Met Leu Ala Ala Glu Leu Gly Gln Ala Pro Gly Leu
                165                 170
```

<210> SEQ ID NO 20
<211> LENGTH: 147
<212> TYPE: PRT
<213> ORGANISM: Streptococcus pneumoniae

<400> SEQUENCE: 20

Met Ala Leu Ala Lys Ile Val Phe Ala Ser Met Thr Gly Asn Thr Glu
1               5                   10                  15

Glu Ile Ala Asp Ile Val Ala Asp Lys Leu Arg Asp Leu Gly Leu Asp
                20                  25                  30

Val Asp Val Asp Glu Cys Thr Thr Val Asp Ala Ser Asp Phe Leu Glu
            35                  40                  45

Ala Asp Ile Ala Ile Val Ala Thr Tyr Thr Tyr Gly Asp Gly Glu Leu
        50                  55                  60

Pro Asp Glu Met Met Asp Phe Tyr Glu Asp Leu Ala Asp Leu Asn Leu
65                  70                  75                  80

Asn Gly Lys Ile Tyr Gly Val Val Gly Ser Gly Asp Thr Phe Tyr Asp
                85                  90                  95

Glu Phe Cys Lys Ala Val Asp Asp Phe Asp Arg Val Phe Val Ser Thr
                100                 105                 110

Gly Ala Glu Lys Gly Ser Glu Cys Val Lys Val Asp Leu Ser Ala Glu
            115                 120                 125

Glu Glu Asp Ile Glu Arg Leu Glu Gln Phe Ala Glu Glu Leu Ala Ala
        130                 135                 140

Lys Val Gly
145

<210> SEQ ID NO 21
<211> LENGTH: 178
<212> TYPE: PRT
<213> ORGANISM: Streptococcus pneumoniae

<400> SEQUENCE: 21

Met Ser Arg Ile Gly Asn Lys Val Ile Val Leu Pro Ala Gly Val Glu
1               5                   10                  15

Leu Ala Asn Asn Asp Asn Val Val Thr Val Lys Gly Ser Lys Gly Glu
                20                  25                  30

Leu Thr Arg Glu Phe Ser Lys Asp Ile Glu Ile Arg Val Glu Gly Thr
            35                  40                  45

Glu Ile Thr Leu His Arg Pro Asn Asp Ser Lys Glu Met Lys Thr Ile
        50                  55                  60

His Gly Thr Thr Arg Ala Leu Leu Asn Asn Met Val Val Gly Val Ser
65                  70                  75                  80

Glu Gly Phe Lys Lys Glu Leu Glu Met Arg Gly Val Gly Tyr Arg Ala
                85                  90                  95

Gln Leu Gln Gly Ser Lys Leu Val Leu Ala Val Gly Lys Ser His Pro
                100                 105                 110

Asp Glu Val Glu Ala Pro Glu Gly Ile Thr Phe Glu Leu Pro Asn Pro
            115                 120                 125

Thr Thr Ile Val Val Ser Gly Ile Ser Lys Glu Val Val Gly Gln Thr
        130                 135                 140

Ala Ala Tyr Val Arg Ser Leu Arg Ser Pro Glu Pro Tyr Lys Gly Lys
145                 150                 155                 160

Gly Ile Arg Tyr Val Gly Glu Phe Val Arg Arg Lys Glu Gly Lys Thr
                165                 170                 175

Gly Lys

<210> SEQ ID NO 22
<211> LENGTH: 180
<212> TYPE: PRT
<213> ORGANISM: Streptococcus pneumoniae

<400> SEQUENCE: 22

Met Ala Asn Arg Leu Lys Glu Lys Tyr Leu Asn Glu Val Val Pro Ala
1               5                   10                  15

Leu Thr Glu Gln Phe Asn Tyr Ser Ser Val Met Ala Val Pro Lys Val
            20                  25                  30

Asp Lys Ile Val Leu Asn Met Gly Val Gly Glu Ala Val Ser Asn Ala
        35                  40                  45

Lys Ser Leu Glu Lys Ala Ala Glu Glu Leu Ala Leu Ile Ser Gly Gln
    50                  55                  60

Lys Pro Leu Ile Thr Lys Ala Lys Lys Ser Ile Ala Gly Phe Arg Leu
65                  70                  75                  80

Arg Glu Gly Val Ala Ile Gly Ala Lys Val Thr Leu Arg Gly Glu Arg
                85                  90                  95

Met Tyr Glu Phe Leu Asp Lys Leu Val Ser Val Ser Leu Pro Arg Val
            100                 105                 110

Arg Asp Phe His Gly Val Pro Thr Lys Ser Phe Asp Gly Arg Gly Asn
        115                 120                 125

Tyr Thr Leu Gly Val Lys Glu Gln Leu Ile Phe Pro Glu Ile Asn Phe
    130                 135                 140

Asp Asp Val Asp Lys Thr Arg Gly Leu Asp Ile Val Ile Val Thr Thr
145                 150                 155                 160

Ala Asn Thr Asp Glu Glu Ser Arg Ala Leu Leu Thr Gly Leu Gly Met
                165                 170                 175

Pro Phe Ala Lys
            180

<210> SEQ ID NO 23
<211> LENGTH: 178
<212> TYPE: PRT
<213> ORGANISM: Streptococcus gordonii

<400> SEQUENCE: 23

Met Asp Ser Phe Asp Lys Gly Trp Phe Val Leu Gln Thr Tyr Ser Gly
1               5                   10                  15

Tyr Glu Asn Lys Val Lys Glu Asn Leu Leu Gln Arg Ala Gln Thr Tyr
            20                  25                  30

Asn Met Leu Glu Asn Ile Leu Arg Val Glu Ile Pro Thr Gln Thr Val
        35                  40                  45

Gln Val Glu Lys Asn Gly Lys Thr Lys Glu Ile Glu Glu Asn Arg Phe
    50                  55                  60

Pro Gly Tyr Val Leu Val Glu Met Val Met Thr Asp Glu Ala Trp Phe
65                  70                  75                  80

Val Val Arg Asn Thr Pro Asn Val Thr Gly Phe Val Gly Ser His Gly
                85                  90                  95

Asn Arg Ser Lys Pro Thr Pro Leu Leu Glu Glu Ile Arg Asn Ile
            100                 105                 110

Leu Ile Ser Met Gly Gln Thr Val Gln Glu Phe Asp Ile His Val Lys
        115                 120                 125

Val Gly Asp Thr Val Arg Ile Ile Asp Gly Ala Phe Thr Asp Tyr Thr
    130                 135                 140

Gly Lys Ile Thr Glu Ile Asp Asn Asn Lys Val Lys Met Val Ile Ser
145                 150                 155                 160

Met Phe Gly Asn Asp Thr Ile Ala Glu Val Asn Leu Asn Gln Ile Ala
                165                 170                 175

Glu Leu

<210> SEQ ID NO 24
<211> LENGTH: 183
<212> TYPE: PRT
<213> ORGANISM: Streptococcus pneumoniae

<400> SEQUENCE: 24

Met Lys Gly Asn Ile Met Asp Ser Phe Asp Lys Gly Trp Phe Val Leu
1               5                   10                  15

Gln Thr Tyr Ser Gly Tyr Glu Asn Lys Val Lys Glu Asn Leu Leu Gln
                20                  25                  30

Arg Ala Gln Thr Tyr Asn Met Leu Asp Asn Ile Leu Arg Val Glu Ile
                35                  40                  45

Pro Thr Gln Thr Val Gln Val Glu Lys Asn Gly Lys Arg Lys Glu Val
50                  55                  60

Glu Glu Asn Arg Phe Pro Gly Tyr Val Leu Val Glu Met Val Met Thr
65                  70                  75                  80

Asp Glu Ala Trp Phe Val Val Arg Asn Thr Pro Asn Val Thr Gly Phe
                85                  90                  95

Val Gly Ser His Gly Asn Arg Ser Lys Pro Thr Pro Leu Leu Glu Gln
                100                 105                 110

Glu Ile Arg Asp Ile Leu Val Ser Met Gly Gln Thr Val Gln Glu Phe
            115                 120                 125

Asp Phe Asp Val Glu Ile Gly Gln Thr Val Arg Ile Ile Asp Gly Ala
130                 135                 140

Phe Ala Asp Tyr Thr Gly Lys Ile Thr Glu Ile Asp Asn Asn Lys Val
145                 150                 155                 160

Lys Met Ile Ile Ser Met Phe Gly Asn Asp Thr Val Ala Glu Val Asn
                165                 170                 175

Leu Asn Gln Ile Ala Glu Leu
            180

<210> SEQ ID NO 25
<211> LENGTH: 163
<212> TYPE: PRT
<213> ORGANISM: Streptococcus pyogenes

<400> SEQUENCE: 25

Met Ile Asn Asn Val Val Leu Val Gly Arg Met Thr Lys Asp Ala Glu
1               5                   10                  15

Leu Arg Tyr Thr Pro Ser Gln Val Ala Val Ala Thr Phe Thr Leu Ala
                20                  25                  30

Val Asn Arg Thr Phe Lys Ser Gln Asn Gly Glu Arg Glu Ala Asp Phe
                35                  40                  45

Ile Asn Cys Val Ile Trp Arg Gln Pro Ala Glu Asn Leu Ala Asn Trp
50                  55                  60

Ala Lys Lys Gly Ala Leu Ile Gly Val Thr Gly Arg Ile Gln Thr Arg
65                  70                  75                  80

Asn Tyr Glu Asn Gln Gln Gly Gln Arg Val Tyr Val Thr Glu Val Val
                85                  90                  95

Ala Asp Asn Phe Gln Met Leu Glu Ser Arg Ala Thr Arg Glu Gly Gly
            100                 105                 110

Ser Thr Gly Ser Phe Asn Gly Gly Phe Asn Asn Asn Thr Ser Ser Ser
        115                 120                 125

Asn Ser Tyr Ser Ala Pro Ala Gln Gln Thr Pro Asn Phe Gly Arg Asp
    130                 135                 140

Asp Ser Pro Phe Gly Asn Ser Asn Pro Met Asp Ile Ser Asp Asp Asp
145                 150                 155                 160

Leu Pro Phe

<210> SEQ ID NO 26
<211> LENGTH: 191
<212> TYPE: PRT
<213> ORGANISM: Streptococcus pneumoniae

<400> SEQUENCE: 26

Met Thr Lys Ala Leu Ile Ser Ile Asp Tyr Thr Glu Asp Phe Val Ala
1               5                   10                  15

Asp Ser Gly Lys Leu Thr Ala Gly Ala Pro Ala Gln Ala Ile Ser Asp
            20                  25                  30

Ala Ile Ser Lys Val Thr Arg Leu Ala Phe Glu Arg Gly Asp Tyr Ile
        35                  40                  45

Phe Phe Thr Ile Asp Ala His Glu Glu Asn Asp Cys Phe His Pro Glu
    50                  55                  60

Ser Lys Leu Phe Pro Pro His Asn Leu Ile Gly Thr Ser Gly Arg Asn
65                  70                  75                  80

Leu Tyr Gly Asp Leu Gly Ile Phe Tyr Gln Glu His Gly Ser Asp Ser
                85                  90                  95

Arg Val Phe Trp Met Asp Lys Arg His Tyr Ser Ala Phe Ser Gly Thr
            100                 105                 110

Asp Leu Asp Ile Arg Leu Arg Glu Arg Arg Val Ser Thr Val Ile Leu
        115                 120                 125

Thr Gly Val Leu Thr Asp Ile Cys Val Leu His Thr Ala Ile Asp Ser
    130                 135                 140

Tyr Asn Leu Gly Tyr Asp Ile Glu Ile Val Lys Pro Ala Val Ala Ser
145                 150                 155                 160

Ile Trp Pro Glu Asn His Gln Phe Ala Leu Gly His Phe Lys Asn Thr
                165                 170                 175

Leu Gly Ala Lys Leu Val Asp Glu Asn Leu Asn Glu Leu Ser Glu
            180                 185                 190

<210> SEQ ID NO 27
<211> LENGTH: 293
<212> TYPE: PRT
<213> ORGANISM: Streptococcus pneumoniae

<400> SEQUENCE: 27

Met Ala Ile Val Ser Ala Glu Lys Phe Val Gln Ala Arg Asp Asn
1               5                   10                  15

Gly Tyr Ala Val Gly Gly Phe Asn Thr Asn Asn Leu Glu Trp Thr Gln
            20                  25                  30

Ala Ile Leu Arg Ala Ala Glu Lys Lys Ala Pro Val Leu Ile Gln
        35                  40                  45

Thr Ser Met Gly Ala Ala Lys Tyr Met Gly Gly Tyr Lys Val Ala Arg
    50                  55                  60

Asn Leu Ile Ala Asn Leu Val Glu Ser Met Gly Ile Thr Val Pro Val

```
65                  70                  75                  80
Ala Ile His Leu Asp His Gly His Tyr Glu Asp Ala Leu Glu Cys Ile
                85                  90                  95
Glu Val Gly Tyr Thr Ser Ile Met Phe Asp Gly Ser His Leu Pro Val
            100                 105                 110
Glu Glu Asn Leu Lys Leu Ala Lys Glu Val Val Glu Lys Ala His Ala
            115                 120                 125
Lys Gly Ile Ser Val Glu Ala Glu Val Gly Thr Ile Gly Gly Glu Glu
        130                 135                 140
Asp Gly Ile Ile Gly Lys Gly Glu Leu Ala Pro Ile Glu Asp Ala Lys
145                 150                 155                 160
Ala Met Val Glu Thr Gly Ile Asp Phe Leu Ala Gly Ile Gly Asn
                165                 170                 175
Ile His Gly Pro Tyr Pro Val Asn Trp Glu Gly Leu Asp Leu Asp His
            180                 185                 190
Leu Gln Lys Leu Thr Glu Ala Leu Pro Gly Phe Pro Ile Val Leu His
            195                 200                 205
Gly Gly Ser Gly Ile Pro Asp Glu Gln Ile Gln Ala Ala Ile Lys Leu
        210                 215                 220
Gly Val Ala Lys Val Asn Val Asn Thr Glu Cys Gln Ile Ala Phe Ala
225                 230                 235                 240
Asn Ala Thr Arg Lys Phe Ala Arg Asp Tyr Glu Ala Asn Glu Ala Glu
                245                 250                 255
Tyr Asp Lys Lys Lys Leu Phe Asp Pro Arg Lys Phe Leu Ala Asp Gly
            260                 265                 270
Val Lys Ala Ile Gln Ala Ser Val Glu Glu Arg Ile Asp Val Phe Gly
            275                 280                 285
Ser Glu Gly Lys Ala
        290

<210> SEQ ID NO 28
<211> LENGTH: 311
<212> TYPE: PRT
<213> ORGANISM: Streptococcus pneumoniae

<400> SEQUENCE: 28

Met Ser Lys Ile Leu Val Phe Gly His Gln Asn Pro Asp Ser Asp Ala
1               5                   10                  15
Ile Gly Ser Ser Val Ala Phe Ala Tyr Leu Ala Lys Glu Ala Tyr Gly
            20                  25                  30
Leu Asp Thr Glu Ala Val Ala Leu Gly Thr Pro Asn Glu Glu Thr Ala
        35                  40                  45
Phe Val Leu Asn Tyr Phe Gly Val Glu Ala Pro Arg Val Ile Thr Ser
    50                  55                  60
Ala Lys Ala Glu Gly Ala Glu Gln Val Ile Leu Thr Asp His Asn Glu
65                  70                  75                  80
Phe Gln Gln Ser Val Ser Asp Ile Ala Glu Val Glu Val Tyr Gly Val
                85                  90                  95
Val Asp His His Arg Val Ala Asn Phe Glu Thr Ala Ser Pro Leu Tyr
            100                 105                 110
Met Arg Leu Glu Pro Val Gly Ser Ala Ser Ser Ile Val Tyr Arg Met
        115                 120                 125
Phe Lys Glu His Gly Val Ala Val Pro Lys Glu Ile Ala Gly Leu Met
    130                 135                 140
```

-continued

```
Leu Ser Gly Leu Ile Ser Asp Thr Leu Leu Lys Ser Pro Thr Thr
145                 150                 155                 160

His Pro Thr Asp Lys Ile Ile Ala Pro Glu Leu Ala Glu Leu Ala Gly
                165                 170                 175

Val Asn Leu Glu Glu Tyr Gly Leu Ala Met Leu Lys Ala Gly Thr Asn
            180                 185                 190

Leu Ala Ser Lys Ser Ala Glu Leu Ile Asp Ile Asp Ala Lys Thr
            195                 200                 205

Phe Glu Leu Asn Gly Asn Asn Val Arg Val Ala Gln Val Asn Thr Val
210                 215                 220

Asp Ile Ala Glu Val Leu Glu Arg Gln Ala Glu Ile Glu Ala Ala Met
225                 230                 235                 240

Gln Ala Ala Asn Glu Ser Asn Gly Tyr Ser Asp Phe Val Leu Met Ile
                245                 250                 255

Thr Asp Ile Val Asn Ser Asn Ser Glu Ile Leu Ala Leu Gly Ala Asn
                260                 265                 270

Met Asp Lys Val Glu Ala Ala Phe Asn Phe Lys Leu Glu Asn Asn His
            275                 280                 285

Ala Phe Leu Ala Gly Ala Val Ser Arg Lys Lys Gln Val Val Pro Gln
290                 295                 300

Leu Thr Glu Ser Phe Asn Ala
305                 310

<210> SEQ ID NO 29
<211> LENGTH: 311
<212> TYPE: PRT
<213> ORGANISM: Streptococcus pyogenes

<400> SEQUENCE: 29

Met Ser Lys Ile Leu Val Phe Gly His Gln Asn Pro Asp Thr Asp Ala
1               5                   10                  15

Ile Ala Ser Ser Tyr Ala Phe Asp Tyr Leu Ser Gln Lys Ala Phe Gly
            20                  25                  30

Leu Asp Thr Glu Val Val Ala Leu Gly Thr Pro Asn Glu Glu Thr Ala
        35                  40                  45

Phe Ala Leu Asp Tyr Phe Gly Val Glu Ala Pro Arg Val Val Glu Ser
50                  55                  60

Ala Lys Ala Gln Gly Ser Glu Gln Val Ile Leu Thr Asp His Asn Glu
65                  70                  75                  80

Phe Gln Gln Ser Ile Ala Asp Ile Arg Glu Val Glu Val Tyr Gly Val
                85                  90                  95

Val Asp His His Arg Val Ala Asn Phe Glu Thr Ala Asn Pro Leu Tyr
            100                 105                 110

Met Arg Val Glu Pro Val Gly Ser Ala Ser Ser Ile Val Tyr Arg Met
            115                 120                 125

Phe Lys Glu Asn Gly Ile Glu Val Pro Lys Ala Ile Ala Gly Met Leu
130                 135                 140

Leu Ser Gly Leu Ile Ser Asp Thr Leu Leu Lys Ser Pro Thr Thr
145                 150                 155                 160

His Val Ser Asp His Leu Val Ala Glu Glu Leu Ala Glu Leu Ala Glu
                165                 170                 175

Val Asn Leu Glu Asp Tyr Gly Met Ala Leu Leu Lys Ala Gly Thr Asn
            180                 185                 190

Leu Ala Ser Lys Ser Glu Val Glu Leu Ile Gly Ile Asp Ala Lys Thr
            195                 200                 205
```

```
Phe Glu Leu Asn Gly Asn Ala Val Arg Val Ala Gln Val Asn Thr Val
    210                 215                 220
Asp Ile Ala Glu Val Leu Glu Arg Gln Glu Ala Ile Glu Ala Ala Ile
225                 230                 235                 240
Lys Asp Ala Met Ala Ala Glu Gly Tyr Ser Asp Phe Val Leu Met Ile
                245                 250                 255
Thr Asp Ile Val Asn Ser Asn Ser Glu Ile Leu Ala Ile Gly Ala Asn
                260                 265                 270
Met Asp Lys Val Glu Ala Ala Phe Asn Phe Thr Leu Asp Asn Asn His
            275                 280                 285
Ala Phe Leu Ala Gly Ala Val Ser Arg Lys Lys Gln Val Val Pro Gln
        290                 295                 300
Leu Thr Glu Ser Phe Gly Ala
305                 310
```

<210> SEQ ID NO 30
<211> LENGTH: 336
<212> TYPE: PRT
<213> ORGANISM: Streptococcus gordonii

<400> SEQUENCE: 30

```
Met Val Val Lys Val Gly Ile Asn Gly Phe Gly Arg Ile Gly Arg Leu
1               5                   10                  15
Ala Phe Arg Arg Ile Gln Asn Val Glu Gly Val Glu Val Thr Arg Ile
                20                  25                  30
Asn Asp Leu Thr Asp Pro Val Met Leu Ala His Leu Leu Lys Tyr Asp
            35                  40                  45
Thr Thr Gln Gly Arg Phe Asp Gly Thr Val Glu Val Lys Glu Gly Gly
        50                  55                  60
Phe Glu Val Asn Gly Lys Phe Val Lys Val Ser Ala Glu Arg Asp Pro
65                  70                  75                  80
Glu Gln Ile Asp Trp Ala Asn Asp Gly Val Glu Ile Val Leu Glu Ala
                85                  90                  95
Thr Gly Phe Phe Ala Thr Lys Ala Ala Ala Glu Lys His Leu His Ala
                100                 105                 110
Gly Gly Ala Lys Lys Val Val Ile Thr Ala Pro Gly Gly Ser Asp Val
            115                 120                 125
Lys Thr Val Val Phe Asn Thr Asn His Asp Ile Leu Asp Gly Thr Glu
        130                 135                 140
Thr Val Ile Ser Gly Ala Ser Cys Thr Thr Asn Cys Leu Ala Pro Met
145                 150                 155                 160
Ala Lys Ala Leu Gln Asp Asn Phe Gly Val Val Glu Gly Leu Met Thr
                165                 170                 175
Thr Ile His Ala Tyr Thr Gly Asp Gln Met Ile Leu Asp Gly Pro His
                180                 185                 190
Arg Lys Gly Asp Leu Arg Arg Ala Arg Ala Gly Ala Ala Asn Ile Val
            195                 200                 205
Pro Asn Ser Thr Gly Ala Ala Lys Ala Ile Gly Leu Val Ile Pro Glu
        210                 215                 220
Leu Asn Gly Lys Leu Asp Gly Ala Ala Gln Arg Val Pro Thr Pro Thr
225                 230                 235                 240
Gly Ser Val Thr Glu Leu Val Val Val Leu Glu Lys Asn Val Thr Val
                245                 250                 255
Asp Glu Val Asn Ala Ala Met Lys Ala Val Ala Asn Glu Ser Tyr Gly
```

```
                    260                 265                 270
Tyr Thr Glu Asp Pro Ile Val Ser Ser Asp Val Val Gly Met Ser Tyr
        275                 280                 285

Gly Ser Leu Phe Asp Ala Thr Gln Thr Lys Val Leu Asp Val Asp Gly
        290                 295                 300

Lys Gln Leu Val Lys Val Ser Trp Tyr Asp Asn Glu Met Ser Tyr
305                 310                 315                 320

Thr Ala Gln Leu Val Arg Thr Leu Glu Tyr Phe Ala Lys Ile Ala Lys
            325                 330                 335

<210> SEQ ID NO 31
<211> LENGTH: 336
<212> TYPE: PRT
<213> ORGANISM: Streptococcus pyogenes

<400> SEQUENCE: 31

Met Val Val Lys Val Gly Ile Asn Gly Phe Gly Arg Ile Gly Arg Leu
1               5                   10                  15

Ala Phe Arg Arg Ile Gln Asn Ile Glu Gly Val Glu Val Thr Arg Ile
            20                  25                  30

Asn Asp Leu Thr Asp Pro Asn Met Leu Ala His Leu Leu Lys Tyr Asp
        35                  40                  45

Thr Thr Gln Gly Arg Phe Asp Gly Thr Val Glu Val Lys Glu Gly Gly
    50                  55                  60

Phe Glu Val Asn Gly Asn Phe Ile Lys Val Ser Ala Glu Arg Asp Pro
65                  70                  75                  80

Glu Asn Ile Asp Trp Ala Thr Asp Gly Val Glu Ile Val Leu Glu Ala
                85                  90                  95

Thr Gly Phe Phe Ala Lys Lys Glu Ala Ala Glu Lys His Leu His Ala
            100                 105                 110

Asn Gly Ala Lys Lys Val Val Ile Thr Ala Pro Gly Gly Asn Asp Val
        115                 120                 125

Lys Thr Val Val Phe Asn Thr Asn His Asp Ile Leu Asp Gly Thr Glu
    130                 135                 140

Thr Val Ile Ser Gly Ala Ser Cys Thr Thr Asn Cys Leu Ala Pro Met
145                 150                 155                 160

Ala Lys Ala Leu His Asp Ala Phe Gly Ile Gln Lys Gly Leu Met Thr
                165                 170                 175

Thr Ile His Ala Tyr Thr Gly Asp Gln Met Ile Leu Asp Gly Pro His
            180                 185                 190

Arg Gly Gly Asp Leu Arg Arg Ala Arg Ala Gly Ala Ala Asn Ile Val
        195                 200                 205

Pro Asn Ser Thr Gly Ala Ala Lys Ala Ile Gly Leu Val Ile Pro Glu
    210                 215                 220

Leu Asn Gly Lys Leu Asp Gly Ala Ala Gln Arg Val Pro Val Pro Thr
225                 230                 235                 240

Gly Ser Val Thr Glu Leu Val Val Thr Leu Asp Lys Asn Val Ser Val
                245                 250                 255

Asp Glu Ile Asn Ala Ala Met Lys Ala Ala Ser Asn Asp Ser Phe Gly
            260                 265                 270

Tyr Thr Glu Asp Pro Ile Val Ser Ser Asp Ile Val Gly Val Ser Tyr
        275                 280                 285

Gly Ser Leu Phe Asp Ala Thr Gln Thr Lys Val Met Glu Val Asp Gly
    290                 295                 300
```

```
Ser Gln Leu Val Lys Val Ser Trp Tyr Asp Asn Glu Met Ser Tyr
305                 310                 315                 320

Thr Ala Gln Leu Val Arg Thr Leu Glu Tyr Phe Ala Lys Ile Ala Lys
                325                 330                 335

<210> SEQ ID NO 32
<211> LENGTH: 256
<212> TYPE: PRT
<213> ORGANISM: Streptococcus agalactiae

<400> SEQUENCE: 32

Met Ala Val Ile Ser Met Lys Gln Leu Leu Glu Ala Gly Val His Phe
1               5                   10                  15

Gly His Gln Thr Arg Arg Trp Asn Pro Lys Met Ala Lys Tyr Ile Phe
                20                  25                  30

Thr Glu Arg Asn Gly Ile His Val Ile Asp Leu Gln Gln Thr Val Lys
            35                  40                  45

Leu Ala Asp Gln Ala Tyr Glu Phe Val Arg Asp Ala Ala Asn Asp
50                  55                  60

Ala Val Ile Leu Phe Val Gly Thr Lys Lys Gln Ala Glu Ala Val
65                  70                  75                  80

Ala Glu Glu Ala Lys Arg Ala Gly Gln Tyr Phe Ile Asn His Arg Trp
                85                  90                  95

Leu Gly Gly Thr Leu Thr Asn Trp Gly Thr Ile Gln Lys Arg Ile Ala
            100                 105                 110

Arg Leu Lys Glu Ile Lys Arg Met Glu Glu Glu Gly Thr Phe Glu Leu
        115                 120                 125

Leu Pro Lys Lys Glu Val Ala Leu Leu Asn Lys Gln Arg Ala Arg Leu
130                 135                 140

Glu Lys Phe Leu Gly Gly Ile Glu Asp Met Pro Arg Ile Pro Asp Val
145                 150                 155                 160

Met Tyr Val Val Asp Pro His Lys Glu Gln Ile Ala Val Lys Glu Ala
                165                 170                 175

Lys Lys Leu Gly Ile Pro Val Val Ala Met Val Asp Thr Asn Ala Asp
            180                 185                 190

Pro Asp Asp Ile Asp Val Ile Ile Pro Ala Asn Asp Ala Ile Arg
        195                 200                 205

Ala Val Lys Leu Ile Thr Ser Lys Leu Ala Asp Ala Val Ile Glu Gly
210                 215                 220

Arg Gln Gly Glu Asp Ala Asp Val Asp Phe Ala Gln Glu Ala Gln Ala
225                 230                 235                 240

Asp Ser Ile Glu Glu Ile Val Glu Val Glu Gly Ser Asn Asn Asp
                245                 250                 255

<210> SEQ ID NO 33
<211> LENGTH: 303
<212> TYPE: PRT
<213> ORGANISM: Streptococcus pneumoniae

<400> SEQUENCE: 33

Met Tyr Asp Thr Ile Ile Ile Gly Ala Gly Pro Ala Gly Met Thr Ala
1               5                   10                  15

Ala Leu Tyr Ala Ala Arg Ser Asn Leu Lys Val Ala Leu Ile Glu Gly
                20                  25                  30

Gly Leu Pro Gly Gly Gln Met Asn Asn Thr Ser Asp Ile Glu Asn Tyr
            35                  40                  45
```

Pro Gly Tyr Ala Asn Ile Ser Gly Pro Glu Leu Ala Glu Lys Met Phe
            50                  55                  60

Glu Pro Leu Glu Asn Leu Gly Val Glu His Ile Tyr Gly Tyr Val Glu
 65                  70                  75                  80

Asn Val Glu Asp His Gly Asp Phe Lys Lys Val Met Thr Asp Asp Gln
                 85                  90                  95

Thr Tyr Glu Thr Arg Thr Val Ile Val Ala Thr Gly Ser Lys His Arg
            100                 105                 110

Pro Leu Gly Val Pro Gly Glu Glu Leu Asn Ser Arg Gly Val Ser
            115                 120                 125

Tyr Cys Ala Val Cys Asp Gly Ala Phe Phe Arg Asp Gln Asp Leu Leu
    130                 135                 140

Val Val Gly Gly Gly Asp Ser Ala Val Glu Glu Ala Leu Phe Leu Thr
145                 150                 155                 160

Arg Phe Ala Lys Thr Val Thr Ile Val His Arg Arg Asp Gln Leu Arg
                165                 170                 175

Ala Gln Lys Val Leu Gln Asp Arg Ala Phe Ala Asn Glu Lys Ile Ser
            180                 185                 190

Phe Ile Trp Asp Ser Val Val Lys Glu Ile Lys Gly Glu Asn Arg Val
    195                 200                 205

Glu Ser Val Val Phe Glu Asn Val Lys Thr Gly Gln Val Thr Glu Gln
210                 215                 220

Ala Phe Gly Gly Val Phe Ile Tyr Val Gly Leu Asp Pro Leu Ser Asp
225                 230                 235                 240

Phe Val Lys Glu Leu Asn Ile Gln Asp Gln Ala Gly Trp Ile Val Thr
                245                 250                 255

Asp Ser His Met Lys Thr Ala Val Asp Gly Ile Phe Ala Val Gly Asp
            260                 265                 270

Val Arg Leu Lys Asp Leu Arg Gln Val Thr Thr Ala Val Gly Asp Gly
    275                 280                 285

Ala Ile Ala Gly Gln Glu Ala Tyr Lys Phe Ile Thr Glu His Ser
290                 295                 300

<210> SEQ ID NO 34
<211> LENGTH: 311
<212> TYPE: PRT
<213> ORGANISM: Streptococcus pneumoniae

<400> SEQUENCE: 34

Met Thr Lys Leu Ile Phe Met Gly Thr Pro Asp Phe Ser Ala Thr Val
 1               5                  10                  15

Leu Lys Gly Leu Leu Thr Asp Asp Arg Tyr Glu Ile Leu Ala Val Val
                 20                  25                  30

Thr Gln Pro Asp Arg Ala Val Gly Arg Lys Lys Val Ile Gln Glu Thr
             35                  40                  45

Pro Val Lys Gln Ala Ala Lys Glu Ala Gly Leu Ser Ile Tyr Gln Pro
    50                  55                  60

Glu Lys Leu Ser Gly Ser Pro Glu Met Glu Asp Leu Met Lys Leu Gly
 65                  70                  75                  80

Ala Asp Gly Ile Val Thr Ala Ala Phe Gly Gln Phe Leu Pro Ser Lys
                 85                  90                  95

Leu Leu Asp Ser Met Asp Phe Ala Val Asn Val His Ala Ser Leu Leu
            100                 105                 110

Pro Arg His Arg Gly Gly Ala Pro Ile His Tyr Ala Leu Ile Gln Gly
    115                 120                 125

```
Asp Glu Glu Ala Gly Val Thr Ile Met Glu Met Val Lys Glu Met Asp
            130                 135                 140

Ala Gly Asp Met Ile Ser Arg Arg Ser Ile Pro Ile Thr Asp Glu Asp
145                 150                 155                 160

Asn Val Gly Thr Leu Phe Glu Lys Leu Ala Leu Val Gly Arg Asp Leu
                165                 170                 175

Leu Leu Asp Thr Leu Pro Ala Tyr Ile Ala Gly Asp Ile Lys Pro Glu
            180                 185                 190

Pro Gln Asp Thr Ser Gln Val Thr Phe Ser Pro Asn Ile Lys Ser Glu
        195                 200                 205

Glu Glu Lys Leu Asn Trp Asn Lys Thr Asn Arg Gln Leu Phe Asn Gln
210                 215                 220

Ile Arg Gly Met Asn Pro Trp Pro Val Ala His Thr Phe Leu Lys Gly
225                 230                 235                 240

Asp Arg Phe Lys Ile Tyr Glu Ala Leu Pro Val Glu Gly Gln Gly Asn
                245                 250                 255

Pro Gly Glu Ile Leu Ser Ile Gly Lys Lys Glu Leu Ile Val Ala Thr
            260                 265                 270

Ala Glu Gly Ala Leu Ser Leu Lys Gln Val Gln Pro Ala Gly Lys Pro
        275                 280                 285

Lys Met Asp Ile Ala Ser Phe Leu Asn Gly Val Gly Arg Thr Leu Thr
290                 295                 300

Val Gly Glu Arg Phe Gly Asp
305                 310

<210> SEQ ID NO 35
<211> LENGTH: 284
<212> TYPE: PRT
<213> ORGANISM: Streptococcus pneumoniae

<400> SEQUENCE: 35

Met Asn Thr Asn Leu Ala Ser Phe Ile Val Gly Leu Ile Ile Asp Glu
1               5                   10                  15

Asn Asp Arg Phe Tyr Phe Val Gln Lys Asp Gly Gln Thr Tyr Ala Leu
                20                  25                  30

Ala Lys Glu Glu Gly Gln His Thr Val Gly Asp Thr Val Lys Gly Phe
            35                  40                  45

Ala Tyr Thr Asp Met Lys Gln Lys Leu Arg Leu Thr Thr Leu Glu Val
        50                  55                  60

Thr Ala Thr Gln Asp Gln Phe Gly Trp Gly Arg Val Thr Glu Val Arg
65                  70                  75                  80

Lys Asp Leu Gly Val Phe Val Asp Thr Gly Leu Pro Asp Lys Glu Ile
                85                  90                  95

Val Val Ser Leu Asp Ile Leu Pro Glu Leu Lys Glu Leu Trp Pro Lys
            100                 105                 110

Lys Gly Asp Gln Leu Tyr Ile Arg Leu Glu Val Asp Lys Lys Asp Arg
        115                 120                 125

Ile Trp Gly Leu Leu Ala Tyr Gln Glu Asp Phe Gln Arg Leu Ala Arg
130                 135                 140

Pro Ala Tyr Asn Asn Met Gln Asn Gln Asn Trp Pro Ala Ile Val Tyr
145                 150                 155                 160

Arg Leu Lys Leu Ser Gly Thr Phe Val Tyr Leu Pro Glu Asn Asn Met
                165                 170                 175

Leu Gly Phe Ile His Pro Ser Glu Arg Tyr Ala Glu Pro Arg Leu Gly
```

```
                180                 185                 190
    Gln Val Leu Asp Ala Arg Val Ile Gly Phe Arg Glu Val Asp Arg Thr
            195                 200                 205

Leu Asn Leu Ser Leu Lys Pro Arg Ser Phe Glu Met Leu Glu Asn Asp
        210                 215                 220

Ala Gln Met Ile Leu Thr Tyr Leu Glu Ser Asn Gly Gly Phe Met Thr
    225                 230                 235                 240

Leu Asn Asp Lys Ser Ser Pro Asp Asp Ile Lys Ala Thr Phe Gly Ile
                    245                 250                 255

Ser Lys Gly Gln Phe Lys Lys Ala Leu Gly Gly Leu Met Lys Ala Gly
                260                 265                 270

Lys Ile Lys Gln Asp Gln Phe Gly Thr Glu Leu Ile
                275                 280

<210> SEQ ID NO 36
<211> LENGTH: 327
<212> TYPE: PRT
<213> ORGANISM: Streptococcus pyogenes

<400> SEQUENCE: 36

Met Thr Ala Thr Lys Gln His Lys Lys Val Ile Leu Val Gly Asp Gly
    1               5                   10                  15

Ala Val Gly Ser Ser Tyr Ala Phe Ala Leu Val Thr Gln Asn Ile Ala
                20                  25                  30

Gln Glu Leu Gly Ile Ile Asp Ile Phe Lys Glu Lys Thr Gln Gly Asp
            35                  40                  45

Ala Glu Asp Leu Ser His Ala Leu Ala Phe Thr Ser Pro Lys Lys Ile
    50                  55                  60

Tyr Ala Ala Asp Tyr Ser Asp Cys His Asp Ala Asp Leu Val Val Leu
    65                  70                  75                  80

Thr Ala Gly Ala Pro Gln Lys Pro Gly Glu Thr Arg Leu Asp Leu Val
                    85                  90                  95

Glu Lys Asn Leu Arg Ile Asn Lys Glu Val Val Thr Gln Ile Val Ala
                100                 105                 110

Ser Gly Phe Lys Gly Ile Phe Leu Val Ala Ala Asn Pro Val Asp Val
            115                 120                 125

Leu Thr Tyr Ser Thr Trp Lys Phe Ser Gly Phe Pro Lys Glu Arg Val
        130                 135                 140

Ile Gly Ser Gly Thr Ser Leu Asp Ser Ala Arg Phe Arg Gln Ala Leu
    145                 150                 155                 160

Ala Ala Lys Ile Gly Val Asp Ala Arg Ser Val His Ala Tyr Ile Met
                    165                 170                 175

Gly Glu His Gly Asp Ser Glu Phe Ala Val Trp Ser His Ala Asn Val
                180                 185                 190

Ala Gly Val Gly Leu Tyr Asp Trp Leu Gln Ala Asn Arg Asp Ile Asp
            195                 200                 205

Glu Gln Gly Leu Val Asp Leu Phe Ile Ser Val Arg Asp Ala Ala Tyr
        210                 215                 220

Ser Ile Ile Asn Lys Lys Gly Ala Thr Phe Tyr Gly Ile Ala Val Ala
    225                 230                 235                 240

Leu Ala Arg Ile Thr Lys Ala Ile Leu Asp Asp Glu Asn Ala Val Leu
                    245                 250                 255

Pro Leu Ser Val Phe Gln Glu Gly Gln Tyr Glu Gly Val Glu Asp Cys
                260                 265                 270
```

Tyr Ile Gly Gln Pro Ala Ile Gly Ala Tyr Gly Ile Val Arg Pro
            275                 280                 285

Val Asn Ile Pro Leu Asn Asp Ala Glu Leu Gln Lys Met Gln Ala Ser
        290                 295                 300

Ala Asn Gln Leu Lys Ala Ile Ile Asp Glu Ala Phe Ala Lys Glu Glu
305                 310                 315                 320

Phe Ala Ser Ala Ala Lys Asn
                325

<210> SEQ ID NO 37
<211> LENGTH: 304
<212> TYPE: PRT
<213> ORGANISM: Streptococcus pyogenes

<400> SEQUENCE: 37

Met Thr Lys Val Arg Lys Ala Ile Ile Pro Ala Ala Gly Leu Gly Thr
1               5                   10                  15

Arg Phe Leu Pro Ala Thr Lys Ala Leu Ala Lys Glu Met Leu Pro Ile
            20                  25                  30

Val Asp Lys Pro Thr Ile Gln Phe Ile Val Glu Glu Ala Leu Lys Ser
        35                  40                  45

Gly Ile Glu Glu Ile Leu Val Val Thr Gly Lys Ala Lys Arg Ser Ile
    50                  55                  60

Glu Asp His Phe Asp Ser Asn Phe Glu Leu Glu Tyr Asn Leu Gln Ala
65                  70                  75                  80

Lys Gly Lys Asn Glu Leu Leu Lys Leu Val Asp Glu Thr Thr Ala Ile
                85                  90                  95

Asn Leu His Phe Ile Arg Gln Ser His Pro Arg Gly Leu Gly Asp Ala
            100                 105                 110

Val Leu Gln Ala Lys Ala Phe Val Gly Asn Glu Pro Phe Val Val Met
        115                 120                 125

Leu Gly Asp Asp Leu Met Asp Ile Thr Asn Ala Ser Ala Lys Pro Leu
    130                 135                 140

Thr Lys Gln Leu Met Glu Asp Tyr Asp Lys Thr His Ala Ser Thr Ile
145                 150                 155                 160

Ala Val Met Lys Val Pro His Glu Asp Val Ser Ser Tyr Gly Val Ile
                165                 170                 175

Ala Pro Gln Gly Lys Ala Val Lys Gly Leu Tyr Ser Val Asp Thr Phe
            180                 185                 190

Val Glu Lys Pro Gln Pro Glu Asp Ala Pro Ser Asp Leu Ala Ile Ile
        195                 200                 205

Gly Arg Tyr Leu Leu Thr Pro Glu Ile Phe Gly Ile Leu Glu Arg Gln
    210                 215                 220

Thr Pro Gly Ala Gly Asn Glu Val Gln Leu Thr Asp Ala Ile Asp Thr
225                 230                 235                 240

Leu Asn Lys Thr Gln Arg Val Phe Ala Arg Glu Phe Lys Gly Asn Arg
                245                 250                 255

Tyr Asp Val Gly Asp Lys Phe Gly Phe Met Lys Thr Ser Ile Asp Tyr
            260                 265                 270

Ala Leu Glu His Pro Gln Val Lys Glu Asp Leu Lys Asn Tyr Ile Ile
        275                 280                 285

Lys Leu Gly Lys Ala Leu Glu Lys Ser Lys Val Pro Thr His Ser Lys
    290                 295                 300

<210> SEQ ID NO 38

```
<211> LENGTH: 306
<212> TYPE: PRT
<213> ORGANISM: Streptococcus pneumoniae

<400> SEQUENCE: 38

Met Ser Ile Tyr Asn Asn Ile Thr Glu Leu Ile Gly Gln Thr Pro Ile
1               5                   10                  15

Val Lys Leu Asn Asn Ile Val Pro Glu Gly Ala Ala Asp Val Tyr Ile
            20                  25                  30

Lys Leu Glu Ala Phe Asn Pro Gly Ser Ser Val Lys Asp Arg Ile Ala
        35                  40                  45

Leu Ser Met Ile Glu Lys Ala Glu Gln Asp Gly Ile Leu Lys Leu Gly
    50                  55                  60

Ser Thr Ile Val Glu Ala Thr Ser Gly Asn Thr Gly Ile Gly Leu Ser
65                  70                  75                  80

Trp Val Gly Ala Ala Lys Gly Tyr Lys Val Ile Val Met Pro Glu
                85                  90                  95

Thr Met Ser Val Glu Arg Arg Lys Ile Ile Gln Ala Tyr Gly Ala Glu
            100                 105                 110

Leu Val Leu Thr Pro Gly Ser Glu Gly Met Lys Gly Ala Ile Ala Lys
        115                 120                 125

Ala Gln Glu Ile Ala Ala Glu Arg Asp Gly Phe Leu Pro Leu Gln Phe
    130                 135                 140

Asp Asn Pro Ala Asn Pro Glu Val His Glu Arg Thr Thr Gly Ala Glu
145                 150                 155                 160

Ile Leu Ala Ala Phe Gly Lys Asp Gly Leu Asp Ala Phe Val Ala Gly
                165                 170                 175

Val Gly Thr Gly Gly Thr Ile Ser Gly Val Ser His Ala Leu Lys Ser
            180                 185                 190

Glu Asn Ser Asn Ile Gln Val Phe Ala Val Glu Ala Asp Glu Ser Ala
        195                 200                 205

Ile Leu Ser Gly Glu Lys Pro Gly Pro His Lys Ile Gln Gly Ile Ser
    210                 215                 220

Ala Gly Phe Ile Pro Asp Thr Leu Asp Thr Lys Ala Tyr Asp Gly Ile
225                 230                 235                 240

Val Arg Val Thr Ser Asp Asp Ala Leu Ala Leu Gly Arg Glu Ile Gly
                245                 250                 255

Gly Lys Glu Gly Phe Leu Val Gly Ile Ser Ser Ala Ala Ile Tyr
            260                 265                 270

Gly Ala Ile Glu Val Ala Lys Lys Leu Gly Thr Gly Lys Lys Val Leu
        275                 280                 285

Ala Leu Ala Pro Asp Asn Gly Glu Arg Tyr Leu Ser Thr Ala Leu Tyr
    290                 295                 300

Glu Leu
305

<210> SEQ ID NO 39
<211> LENGTH: 233
<212> TYPE: PRT
<213> ORGANISM: Streptococcus pneumoniae

<400> SEQUENCE: 39

Met Lys Val Ile Lys Val Glu Asn Gln Val Gln Gly Gly Lys Val Ala
1               5                   10                  15

Phe Glu Ile Leu Lys Glu Lys Leu Ala Asn Gly Ala Gln Thr Leu Gly
            20                  25                  30
```

```
Leu Ala Thr Gly Ser Ser Pro Leu Glu Phe Tyr Lys Glu Ile Val Glu
            35                  40                  45

Ser Asp Leu Asp Phe Ser Asn Leu Thr Ser Val Asn Leu Asp Glu Tyr
 50                  55                  60

Val Gly Leu Asp Gly Asp Asn Pro Gln Ser Tyr Arg Tyr Phe Met Gln
 65                  70                  75                  80

Glu Asn Leu Phe Asn Gln Lys Pro Phe Lys Glu Ser Phe Leu Pro Arg
                85                  90                  95

Gly Val Lys Asp Asn Ala Glu Ala Val Glu Arg Tyr Asn Gln Ile
                    100                 105                 110

Leu Ala Asp His Pro Val Asp Leu Gln Ile Leu Gly Ile Gly Arg Asn
                115                 120                 125

Gly His Ile Gly Phe Asn Glu Pro Gly Thr Pro Phe Asp Ser Gln Thr
130                 135                 140

His Leu Val Glu Leu Asp Gln Ser Thr Ile Glu Ala Asn Ala Arg Phe
145                 150                 155                 160

Phe Ala Lys Ile Glu Asp Val Pro Thr Gln Ala Ile Ser Met Gly Ile
                    165                 170                 175

Lys Asn Ile Leu Asp Ala Lys Ser Ile Ile Leu Phe Ala Tyr Gly Glu
                180                 185                 190

Ser Lys Ala Glu Ala Ile Ala Gly Thr Val Ser Gly Pro Val Thr Glu
            195                 200                 205

Asn Leu Pro Ala Ser Ser Leu Gln Asn His Pro Asp Val Thr Ile Ile
        210                 215                 220

Ala Asp Ala Glu Ala Leu Ser Leu Leu
225                 230

<210> SEQ ID NO 40
<211> LENGTH: 252
<212> TYPE: PRT
<213> ORGANISM: Streptococcus pneumoniae

<400> SEQUENCE: 40

Met Ser Arg Lys Pro Phe Ile Ala Gly Asn Trp Lys Met Asn Lys Asn
 1               5                  10                  15

Pro Glu Glu Ala Lys Ala Phe Val Glu Ala Val Ala Ser Lys Leu Pro
                20                  25                  30

Ser Ser Asp Leu Val Glu Ala Gly Ile Ala Ala Pro Ala Leu Asp Leu
            35                  40                  45

Thr Thr Val Leu Ala Val Ala Lys Gly Ser Asn Leu Lys Val Ala Ala
 50                  55                  60

Gln Asn Cys Tyr Phe Glu Asn Ala Gly Ala Phe Thr Gly Glu Thr Ser
 65                  70                  75                  80

Pro Gln Val Leu Lys Glu Ile Gly Thr Asp Tyr Val Val Ile Gly His
                85                  90                  95

Ser Glu Arg Arg Asp Tyr Phe His Glu Thr Asp Glu Asp Ile Asn Lys
                100                 105                 110

Lys Ala Lys Ala Ile Phe Ala Asn Gly Met Leu Pro Ile Ile Cys Cys
            115                 120                 125

Gly Glu Ser Leu Glu Thr Tyr Glu Ala Gly Lys Ala Ala Glu Phe Val
130                 135                 140

Gly Ala Gln Val Ser Ala Ala Leu Ala Gly Leu Thr Ala Glu Gln Val
145                 150                 155                 160

Ala Ala Ser Val Ile Ala Tyr Glu Pro Ile Trp Ala Ile Gly Thr Gly
```

```
            165                 170                 175
Lys Ser Ala Ser Gln Asp Asp Ala Gln Lys Met Cys Lys Val Val Arg
            180                 185                 190

Asp Val Ala Ala Asp Phe Gly Gln Glu Val Ala Asp Lys Val Arg
            195                 200                 205

Val Gln Tyr Gly Gly Ser Val Lys Pro Glu Asn Val Ala Ser Tyr Met
        210                 215                 220

Ala Cys Pro Asp Val Asp Gly Ala Leu Val Gly Gly Ala Ser Leu Glu
225                 230                 235                 240

Ala Glu Ser Phe Leu Ala Leu Leu Asp Phe Val Lys
                245                 250

<210> SEQ ID NO 41
<211> LENGTH: 243
<212> TYPE: PRT
<213> ORGANISM: Streptococcus pneumoniae

<400> SEQUENCE: 41

Met Lys Leu Glu His Lys Asn Ile Phe Ile Thr Gly Ser Ser Arg Gly
1               5                   10                  15

Ile Gly Leu Ala Ile Ala His Lys Phe Ala Gln Ala Gly Ala Asn Ile
            20                  25                  30

Val Leu Asn Ser Arg Gly Ala Ile Ser Glu Glu Leu Leu Ala Glu Phe
        35                  40                  45

Ser Asn Tyr Gly Ile Lys Val Val Pro Ile Ser Gly Asp Val Ser Asp
    50                  55                  60

Phe Ala Asp Ala Lys Arg Met Ile Asp Gln Ile Ala Glu Leu Gly
65                  70                  75                  80

Ser Val Asp Val Leu Val Asn Asn Ala Gly Ile Thr Gln Asp Thr Leu
                85                  90                  95

Met Leu Lys Met Thr Glu Ala Asp Phe Glu Lys Val Leu Lys Val Asn
            100                 105                 110

Leu Thr Gly Ala Phe Asn Met Thr Gln Ser Val Leu Lys Pro Met Met
        115                 120                 125

Lys Ala Arg Glu Gly Ala Ile Ile Asn Met Ser Ser Val Val Gly Leu
    130                 135                 140

Met Gly Asn Ile Gly Gln Ala Asn Tyr Ala Ala Ser Lys Ala Gly Leu
145                 150                 155                 160

Ile Gly Phe Thr Lys Ser Val Ala Arg Glu Val Ala Ser Arg Asn Ile
                165                 170                 175

Arg Val Asn Val Ile Ala Pro Gly Met Ile Glu Ser Asp Met Thr Ala
            180                 185                 190

Ile Leu Ser Asp Lys Ile Lys Glu Ala Thr Leu Ala Gln Ile Pro Met
        195                 200                 205

Lys Glu Phe Gly Gln Ala Glu Gln Val Ala Asp Leu Thr Val Phe Leu
    210                 215                 220

Ala Gly Gln Asp Tyr Leu Thr Gly Gln Val Val Ala Ile Asp Gly Gly
225                 230                 235                 240

Leu Ser Met

<210> SEQ ID NO 42
<211> LENGTH: 230
<212> TYPE: PRT
<213> ORGANISM: Streptococcus pneumoniae

<400> SEQUENCE: 42
```

```
Met Val Lys Leu Val Phe Ala Arg His Gly Glu Ser Glu Trp Asn Lys
1               5                   10                  15

Ala Asn Leu Phe Thr Gly Trp Ala Asp Val Asp Leu Ser Glu Lys Gly
                20                  25                  30

Thr Gln Gln Ala Ile Asp Ala Gly Lys Leu Ile Lys Glu Ala Gly Ile
            35                  40                  45

Glu Phe Asp Gln Ala Tyr Thr Ser Val Leu Lys Arg Ala Ile Lys Thr
50                  55                  60

Thr Asn Leu Ala Leu Glu Ala Ser Asp Gln Leu Trp Val Pro Val Glu
65                  70                  75                  80

Lys Ser Trp Arg Leu Asn Glu Arg His Tyr Gly Gly Leu Thr Gly Lys
                85                  90                  95

Asn Lys Ala Glu Ala Ala Glu Gln Phe Gly Asp Glu Gln Val His Ile
            100                 105                 110

Trp Arg Arg Ser Tyr Asp Val Leu Pro Pro Asn Met Asp Arg Asp Asp
            115                 120                 125

Glu His Ser Ala His Thr Asp Arg Arg Tyr Ala Ser Leu Asp Asp Ser
        130                 135                 140

Val Ile Pro Asp Ala Glu Asn Leu Lys Val Thr Leu Glu Arg Ala Leu
145                 150                 155                 160

Pro Phe Trp Glu Asp Lys Ile Ala Pro Ala Leu Lys Asp Gly Lys Asn
        165                 170                 175

Val Phe Val Gly Ala His Gly Asn Ser Ile Arg Ala Leu Val Lys His
            180                 185                 190

Ile Lys Gly Leu Ser Asp Asp Glu Ile Met Asp Val Glu Ile Pro Asn
            195                 200                 205

Phe Pro Pro Leu Val Phe Glu Phe Asp Glu Lys Leu Asn Val Val Ser
210                 215                 220

Glu Tyr Tyr Leu Gly Lys
225             230

<210> SEQ ID NO 43
<211> LENGTH: 174
<212> TYPE: PRT
<213> ORGANISM: Streptococcus pneumoniae

<400> SEQUENCE: 43

Met Ala Gln Asp Ile Lys Asn Glu Glu Val Glu Val Gln Glu Glu
1               5                   10                  15

Glu Val Val Lys Thr Ala Glu Gly Thr Thr Pro Glu Lys Ser Glu Leu
                20                  25                  30

Asp Leu Ala Asn Glu Arg Ala Asp Glu Phe Glu Asn Lys Tyr Leu Arg
            35                  40                  45

Ala His Ala Glu Met Gln Asn Ile Gln Arg Arg Ala Asn Glu Glu Arg
50                  55                  60

Gln Asn Leu Gln Arg Tyr Arg Ser Gln Asp Leu Ala Lys Ala Ile Leu
65                  70                  75                  80

Pro Ser Leu Asp Asn Leu Glu Arg Ala Leu Ala Val Glu Gly Leu Thr
                85                  90                  95

Asp Asp Val Lys Lys Gly Leu Gly Met Val Gln Glu Ser Leu Ile His
            100                 105                 110

Ala Leu Lys Glu Glu Gly Ile Glu Glu Ile Ala Ala Asp Gly Glu Phe
            115                 120                 125

Asp His Asn Tyr His Met Ala Ile Gln Thr Leu Pro Ala Asp Asp Glu
```

```
                130             135             140
His Pro Val Asp Thr Ile Ala Gln Val Phe Gln Lys Gly Tyr Lys Leu
145                 150                 155                 160

His Asp Arg Ile Leu Arg Pro Ala Met Val Val Tyr Asn
                165                 170

<210> SEQ ID NO 44
<211> LENGTH: 186
<212> TYPE: PRT
<213> ORGANISM: Streptococcus pneumoniae

<400> SEQUENCE: 44

Met Ile Glu Ala Ser Lys Leu Lys Ala Gly Met Thr Phe Glu Thr Ala
1               5                   10                  15

Asp Gly Lys Leu Ile Arg Val Leu Glu Ala Ser His His Lys Pro Gly
                20                  25                  30

Lys Gly Asn Thr Ile Met Arg Met Lys Leu Arg Asp Val Arg Thr Gly
            35                  40                  45

Ser Thr Phe Asp Thr Ser Tyr Arg Pro Glu Glu Lys Phe Glu Gln Ala
    50                  55                  60

Ile Ile Glu Thr Val Pro Ala Gln Tyr Leu Tyr Lys Met Asp Asp Thr
65                  70                  75                  80

Ala Tyr Phe Met Asn Thr Glu Thr Tyr Asp Gln Tyr Glu Ile Pro Val
                85                  90                  95

Val Asn Val Glu Asn Glu Leu Leu Tyr Ile Leu Glu Asn Ser Asp Val
            100                 105                 110

Lys Ile Gln Phe Tyr Gly Thr Glu Val Ile Gly Val Thr Val Pro Thr
        115                 120                 125

Thr Val Glu Leu Thr Val Ala Glu Thr Gln Pro Ser Ile Lys Gly Ala
    130                 135                 140

Thr Val Thr Gly Ser Gly Lys Pro Ala Thr Met Glu Thr Gly Leu Val
145                 150                 155                 160

Val Asn Val Pro Asp Phe Ile Glu Ala Gly Gln Lys Leu Val Ile Asn
                165                 170                 175

Thr Ala Glu Gly Thr Tyr Val Ser Arg Ala
            180                 185

<210> SEQ ID NO 45
<211> LENGTH: 246
<212> TYPE: PRT
<213> ORGANISM: Streptococcus pneumoniae

<400> SEQUENCE: 45

Met Glu Ile Ser Leu Leu Thr Asp Val Gly Gln Lys Arg Thr Asn Asn
1               5                   10                  15

Gln Asp Tyr Val Asn His Tyr Val Asn Arg Ala Gly Arg Thr Met Ile
                20                  25                  30

Ile Leu Ala Asp Gly Met Gly Gly His Arg Ala Gly Asn Ile Ala Ser
            35                  40                  45

Glu Met Ala Val Thr Asp Leu Gly Val Ala Trp Val Asp Thr Gln Ile
    50                  55                  60

Asp Thr Val Asn Glu Val Arg Glu Trp Phe His Tyr Leu Glu Ile
65                  70                  75                  80

Glu Asn Gln Lys Ile His Gln Leu Gly Gln Asp Glu Ala Tyr Arg Gly
                85                  90                  95

Met Gly Thr Thr Leu Glu Val Leu Ala Ile Ile Asp Asn Gln Ala Ile
```

```
              100                 105                 110
Tyr Ala His Ile Gly Asp Ser Arg Ile Gly Leu Ile Arg Gly Glu Glu
            115                 120                 125

Tyr His Gln Leu Thr Ser Asp His Ser Leu Val Asn Glu Leu Leu Lys
            130                 135                 140

Ala Gly Gln Leu Thr Pro Glu Glu Ala Glu Ala His Pro Gln Lys Asn
145                 150                 155                 160

Ile Ile Thr Gln Ser Ile Gly Gln Lys Asp Glu Ile Gln Pro Asp Phe
                165                 170                 175

Gly Thr Val Ile Leu Glu Ser Gly Asp Tyr Leu Leu Leu Asn Ser Asp
            180                 185                 190

Gly Leu Thr Asn Met Ile Ser Gly Ser Glu Ile Arg Asp Ile Val Thr
            195                 200                 205

Ser Asp Ile Pro Leu Ala Asp Lys Thr Glu Thr Leu Val Arg Phe Ala
            210                 215                 220

Asn Asn Ala Gly Gly Leu Asp Asn Ile Thr Val Ala Leu Val Ser Met
225                 230                 235                 240

Asn Glu Glu Asp Ala Glu
            245

<210> SEQ ID NO 46
<211> LENGTH: 178
<212> TYPE: PRT
<213> ORGANISM: Streptococcus pneumoniae

<400> SEQUENCE: 46

Met Asn Glu Val Lys Lys Met Val Glu Leu Lys Lys Glu Ala Val Lys
1               5                   10                  15

Asp Val Thr Ser Leu Thr Lys Ala Ala Pro Val Ala Leu Ala Lys Thr
            20                  25                  30

Lys Glu Val Leu Asn Gln Ala Val Ala Asp Leu Tyr Val Ala His Val
        35                  40                  45

Ala Leu His Gln Val His Trp Tyr Met His Gly Arg Gly Phe Leu Val
    50                  55                  60

Trp His Pro Lys Met Asp Glu Tyr Met Glu Ala Leu Asp Gly Gln Leu
65                  70                  75                  80

Asp Glu Ile Ser Glu Arg Leu Ile Thr Leu Gly Gly Ser Pro Phe Ser
                85                  90                  95

Thr Leu Thr Glu Phe Leu Gln Asn Ser Glu Ile Glu Glu Glu Ala Gly
            100                 105                 110

Glu Tyr Arg Asn Val Glu Glu Ser Leu Glu Arg Val Leu Val Ile Tyr
        115                 120                 125

Arg Tyr Leu Ser Glu Leu Phe Gln Lys Gly Leu Asp Val Thr Asp Glu
    130                 135                 140

Glu Gly Asp Asp Val Thr Asn Gly Ile Phe Ala Gly Ala Lys Thr Glu
145                 150                 155                 160

Thr Asp Lys Thr Ile Trp Met Leu Ala Ala Glu Leu Gly Gln Ala Pro
                165                 170                 175

Gly Leu

<210> SEQ ID NO 47
<211> LENGTH: 255
<212> TYPE: PRT
<213> ORGANISM: Streptococcus pneumoniae

<400> SEQUENCE: 47
```

```
Met Asn Ile Ala Lys Ile Val Arg Glu Ala Arg Glu Gln Ser Arg Leu
1               5                   10                  15

Thr Thr Leu Asp Phe Ala Thr Gly Ile Phe Asp Glu Phe Ile Gln Leu
            20                  25                  30

His Gly Asp Arg Ser Phe Arg Asp Asp Gly Ala Val Val Gly Gly Ile
            35                  40                  45

Gly Trp Leu Gly Asp Gln Ala Val Thr Val Val Gly Ile Gln Lys Gly
50                  55                  60

Lys Ser Leu Gln Asp Asn Leu Lys Arg Asn Phe Gly Gln Pro His Pro
65                  70                  75                  80

Glu Gly Tyr Arg Lys Ala Leu Arg Leu Met Lys Gln Ala Glu Lys Phe
                85                  90                  95

Gly Arg Pro Val Val Thr Phe Ile Asn Thr Ala Gly Ala Tyr Pro Gly
            100                 105                 110

Val Gly Ala Glu Glu Arg Gly Gln Gly Glu Ala Ile Ala Arg Asn Leu
            115                 120                 125

Met Glu Met Ser Asp Leu Lys Val Pro Ile Ile Ala Ile Ile Ile Gly
130                 135                 140

Glu Gly Gly Ser Gly Gly Ala Leu Ala Leu Ala Val Ala Asp Arg Val
145                 150                 155                 160

Trp Met Leu Glu Asn Ser Ile Tyr Ala Ile Leu Ser Pro Glu Gly Phe
                165                 170                 175

Ala Ser Ile Leu Trp Lys Asp Gly Thr Arg Ala Met Glu Ala Ala Glu
            180                 185                 190

Leu Met Lys Ile Thr Ser His Glu Leu Leu Glu Met Asp Val Val Asp
            195                 200                 205

Lys Val Ile Ser Glu Ile Gly Leu Ser Ser Lys Glu Leu Ile Lys Ser
210                 215                 220

Val Lys Lys Glu Leu Gln Thr Glu Leu Ala Arg Leu Ser Gln Lys Pro
225                 230                 235                 240

Leu Glu Glu Leu Leu Glu Glu Arg Tyr Gln Arg Phe Arg Lys Tyr
                245                 250                 255

<210> SEQ ID NO 48
<211> LENGTH: 185
<212> TYPE: PRT
<213> ORGANISM: Streptococcus pneumoniae

<400> SEQUENCE: 48

Met Ala Asn Ala Ile Ile Glu Lys Ala Lys Glu Arg Met Thr Gln Ser
1               5                   10                  15

His Gln Ser Leu Ala Arg Glu Phe Gly Gly Ile Arg Ala Gly Arg Ala
            20                  25                  30

Asn Ala Ser Leu Leu Asp Arg Val His Val Glu Tyr Tyr Gly Val Glu
            35                  40                  45

Thr Pro Leu Asn Gln Ile Ala Ser Ile Thr Ile Pro Glu Ala Arg Val
50                  55                  60

Leu Leu Val Thr Pro Phe Asp Lys Ser Ser Leu Lys Asp Ile Glu Arg
65                  70                  75                  80

Ala Leu Asn Ala Ser Asp Ile Gly Ile Thr Pro Ala Asn Asp Gly Ser
                85                  90                  95

Val Ile Arg Leu Val Ile Pro Ala Leu Thr Glu Glu Thr Arg Arg Asp
            100                 105                 110

Leu Ala Lys Glu Val Lys Lys Val Gly Glu Asn Ala Lys Val Ala Val
```

```
              115                 120                 125
Arg Asn Ile Arg Arg Asp Ala Met Asp Glu Ala Lys Lys Arg Glu Lys
        130                 135                 140

Ala Lys Glu Ile Thr Glu Asp Glu Leu Lys Thr Leu Glu Lys Asp Ile
145                 150                 155                 160

Gln Lys Val Thr Asp Ala Val Lys His Ile Asp Asp Met Thr Ala
                165                 170                 175

Asn Lys Glu Lys Glu Leu Leu Glu Val
        180                 185

<210> SEQ ID NO 49
<211> LENGTH: 217
<212> TYPE: PRT
<213> ORGANISM: Streptococcus pneumoniae

<400> SEQUENCE: 49

Met Gly Gln Lys Val His Pro Ile Gly Met Arg Val Gly Ile Ile Arg
1               5                   10                  15

Asp Trp Asp Ala Lys Trp Tyr Ala Glu Lys Glu Tyr Ala Asp Tyr Leu
                20                  25                  30

His Glu Asp Leu Ala Ile Arg Lys Phe Val Gln Lys Glu Leu Ala Asp
            35                  40                  45

Ala Ala Val Ser Thr Ile Glu Ile Glu Arg Ala Val Asn Lys Val Asn
        50                  55                  60

Val Ser Leu His Thr Ala Lys Pro Gly Met Val Ile Gly Lys Gly Gly
65                  70                  75                  80

Ala Asn Val Asp Ala Leu Arg Ala Lys Leu Asn Lys Leu Thr Gly Lys
                85                  90                  95

Gln Val His Ile Asn Ile Glu Ile Lys Gln Pro Asp Leu Asp Ala
            100                 105                 110

His Leu Val Gly Glu Gly Ile Ala Arg Gln Leu Glu Gln Arg Val Ala
        115                 120                 125

Phe Arg Arg Ala Gln Lys Gln Ala Ile Gln Arg Ala Met Arg Ala Gly
130                 135                 140

Ala Lys Gly Ile Lys Thr Gln Val Ser Gly Arg Leu Asn Gly Ala Asp
145                 150                 155                 160

Ile Ala Arg Ala Glu Gly Tyr Ser Glu Gly Thr Val Pro Leu His Thr
                165                 170                 175

Leu Arg Ala Asp Ile Asp Tyr Ala Trp Glu Glu Ala Asp Thr Thr Tyr
            180                 185                 190

Gly Lys Leu Gly Val Lys Val Trp Ile Tyr Arg Gly Glu Val Leu Pro
        195                 200                 205

Ala Arg Lys Asn Thr Lys Gly Gly Lys
    210                 215

<210> SEQ ID NO 50
<211> LENGTH: 104
<212> TYPE: PRT
<213> ORGANISM: Streptococcus pneumoniae

<400> SEQUENCE: 50

Met Ala Lys Ala Ile Thr Asp Ala Thr Phe Glu Gln Glu Thr Lys Asp
1               5                   10                  15

Gly Leu Val Leu Val Asp Phe Trp Ala Thr Trp Cys Gly Pro Cys Arg
                20                  25                  30

Met Gln Gly Pro Ile Leu Asp Lys Leu Ser Glu Glu Leu Ser Glu Asp
```

```
                      35                  40                  45
Val Leu Lys Ile Val Lys Met Asp Val Asp Glu Asn Pro Asn Thr Ala
        50                  55                  60

Arg Ala Phe Gly Ile Met Ser Ile Pro Thr Leu Leu Phe Lys Lys Asp
 65                  70                  75                  80

Gly Gln Val Val Lys Gln Val Ala Gly Val His Thr Ala Glu Gln Ile
                85                  90                  95

Lys Ala Ile Ile Ala Glu Leu Ser
            100

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 51

His His His His His His
 1               5
```

US 11,235,047 B2

IMMUNOGENS AND METHODS FOR DISCOVERY AND SCREENING THEREOF

GOVERNMENT SUPPORT

This invention was made with government support under grant number AI066013 awarded by the National Institutes of Health. The government has certain rights in the invention.

FIELD OF THE INVENTION

The present application is generally directed to methods for identifying immunogens from organisms and pathogens, and in particular for identifying immunogens which when administered as vaccines elicit a cellular and/or humoral immune response. The present application is also directed to pneumococcal T-cell immunogens, and methods and compositions thereof.

CROSS REFERENCE TO RELATED APPLICATIONS

This application is a continuation application of U.S. application Ser. No. 13/634,357, which is a 35 U.S.C. § 371 National Phase Entry Application of International Application No. PCT/US2011/028052 filed Mar. 11, 2011, which designates the U.S. and which claims benefit under 35 U.S.C. § 119(e) of U.S. Provisional Application No. 61/428,296 filed Dec. 30, 2010 and U.S. Provisional Application No. 61/428,305, also filed Dec. 30, 2010, and U.S. Provisional Application No. 61/313,450 filed Mar. 12, 2010 the contents of each of which are incorporated herein by reference in their entirities.

SEQUENCE LISTING

The instant application contains a Sequence Listing which has been submitted in ASCII format via EFS-Web and is hereby incorporated by reference in its entirety. Said ASCII copy was created on Jun. 27, 2016, and is named Seq-List-701039-065966.txt and is 13,376 bytes in size.

BACKGROUND OF THE INVENTION

Almost one million children in the developing world die of pneumococcal infections each year. Despite the effectiveness of the conjugate pneumococcal vaccines, problems with this approach remain including the expense of production and delivery, and resulting serotype replacement as demonstrated in several clinical trials and epidemiologic studies. One positive effect of the current capsular-based vaccines has been evident in the patient population that is not being vaccinated: herd immunity plays an impressive role in the current vaccine strategy. For each case of pneumococcal disease prevented in children, about three cases of pneumococcal disease are prevented in adults by herd immunity. In this context at least, prevention of pneumococcal colonization is a main goal of protein-based vaccine approaches, because blocking colonization will block disease.

Alternative pneumococcal vaccines that elicit serotype-independent immunity, and that maybe more readily available to economically emerging countries are needed urgently. New antigens that can address this need would be very attractive. Additionally, current methods to identify immunogens focus on techniques that do not fully optimize the extraction or identification of the full antigen repertoire. This is true in the case of pneumococcus as well as other pathogens. A method that can identify a new set of antigens has potential to be impactful for the development of vaccines for a wide set of pathogens, including pneumococcus.

SUMMARY OF THE INVENTION

An aspect of the present invention provides for methods for identifying novel immunogens that when administered as vaccines elicit a cellular or humoral immunogenic response. In a particular embodiment, a method identified pneumococcal T-cell immunogens that elicit systemic IL-17A responses, and reduce or protect against pneumococcal colonization.

In one embodiment, protective immunogens are identified by killing an organism with an organic solvent. The organic solvent is removed, and the remaining materials re-hydrated in aqueous solution. This process releases various antigens in the liquid phase, which can then be harvested by centrifugation and collection of supernatants.

In another embodiment, the liquid phase is further size-fractionated, or separated by preparative SDS gel or other methods, following which individual fractions are evaluated for immune stimulation. The most promising fractions are then evaluated further to identify components. Component proteins can then be evaluated in combination or singly to determine which are the most immunogenic and protective.

Accordingly, the present approach identified pneumococcal T-cell immunogens that both induce a Th17-cell response and protect mice from colonization. These proteins, including SP0862, SP1534 and SP2070, show promise as vaccine candidates against colonization and sepsis. In some embodiments, the novel pneumococcal immunogens as disclosed herein e.g., as disclosed in Table 1, are administered by mucosal immunization, and can be optionally administered with an adjuvant, to reduce subsequent pneumococcal nasal colonization.

One aspect of the present invention relates to a method for obtaining an immunogen or immunogens from a pathogen, e.g., a bacteria, comprising the steps of: (i) killing a pathogen culture with a solvent, e.g., an organic solvent; (ii) removing the solvent; (iii) resuspending the killed pathogen, e.g., a bacteria, in aqueous solution; (iv) removing particulates from the aqueous solution to retain immunogens in the aqueous solution. In some embodiments, the pathogen is a bacteria, virus, fungi, or parasite. In some embodiments, the immunogen is a protein, carbohydrate, lipid, nucleic acid, or small molecule derived from the pathogen In some embodiments, the method for obtaining an immunogen or immunogens from a pathogen further comprises the steps of: (v) isolating the proteins within the aqueous solution; and (vi) determining specific antibody or T-cell activity of the isolated antigens, in combination or each antigen individually (e.g., singly). In some embodiments, one can optionally determine specific antibody or T-cell activity of the isolated antigens (individually or in any combination) in the presence of an adjuvant and/or a vaccine scaffold.

Another aspect of the present invention relates to a method for obtaining bacterial T-cell-stimulating immunogens comprising the steps of: (i) killing a bacterial culture with a solvent, e.g., an organic solvent; (ii) removing the solvent; (iii) resuspending the killed bacteria in aqueous solution; (iv) removing particulates from the aqueous solution to retain the T-cell immunogens in the aqueous solution. In some embodiments, such a method can optionally further comprise the steps of: (v) isolating the proteins within the aqueous solution; (vi) determining the Th17-cell inducing activity of the isolated proteins, in combination or each antigen individually (e.g., singly). In some embodiments, one can optionally determine specific Th17-cell inducing activity of the isolated antigens (individually or in any combination) in the presence of an adjuvant and/or a vaccine scaffold.

In all aspects of the methods of present invention, a pathogen or bacterial culture can be a culture of *Streptococcus pneumoniae*.

In all aspects of the methods of present invention, a solvent can be an organic solvent, for example, choloroform. In some embodiments the solvent is not alcohol, and in some embodiments, the alcohol is not ethanol.

In some embodiments, an immunogen is further prepared as a vaccine that reduces or protects a mammal against pneumococcal colonization. In some embodiments, such a vaccine can further comprise at least one adjuvant, e.g., selected from the group comprising, but not limited to cholera toxin, CFA, IFA, alum and others commonly known in the art and disclosed herein.

In some embodiments, a vaccine as disclosed herein can be administered to a subject mucosally. In all aspects of all embodiments as described herein, a subject is a mammalian subject, e.g., a human, however other subjects are contemplated such as domestic and agricultural animals and the like.

Other aspects of the present invention relate to a vaccine comprising at least one or a combination of immunogens of the pneumococcal proteins SP0862, SP1534, and SP2070, or functional fragments or proteins thereof having substantial identity.

Another aspect of the present invention relates to a pharmaceutical composition for eliciting an immune response in a mammal comprising pneumococcal proteins SP0862, SP1534, and SP2070, or functional fragments or proteins thereof having substantial identity. In some embodiments, a pharmaceutical composition can further comprise an adjuvant.

Another aspect of the present invention relates to pharmaceutical composition for eliciting an immune response in a mammal comprising the T-cell stimulating immunogens prepared according to the methods as disclosed herein. In such embodiments, a pharmaceutical composition can further comprise an adjuvant and/or a vaccine scaffold.

BRIEF DESCRIPTION OF THE DRAWINGS

FIG. 4A shows IL-17A production in vitro was determined in the blood samples incubated 6 days with pneumococcal whole-cell antigen. FIG. 4B shows that mice were challenged intranasally with serotype 6B strain 0603 four weeks post-immunization, and the density of pneumococcal colonization was determined 7 days later by plating dilutions of nasal washes.

DETAILED DESCRIPTION OF THE INVENTION

Figure 1:
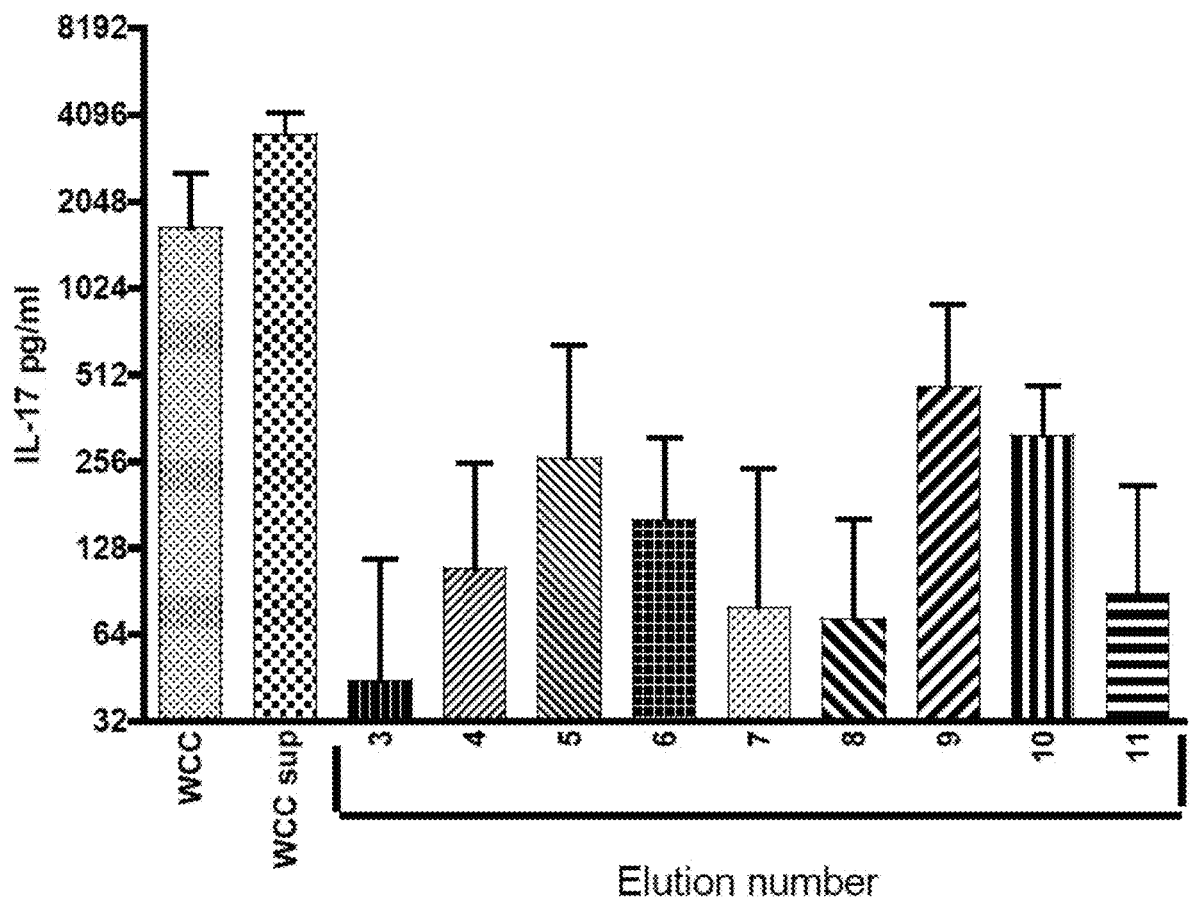
FIG. 1 shows data from a stimulation of splenocytes with elutions from preparative SDS gel separation. The supernatant fraction (WCC sup) contains about 15% of total protein of whole cell vaccine killed by chloroform (WCC). Proteins in WCC sup were separated in a 4%-12% SDS gel and then eluted into fractions according to their mobility in the gel by a preparative SDS gel elution apparatus. Splenocytes from WCC immunized mice were stimulated with the same amount of protein from fraction 3 to 11 and their IL-17A production was measured by ELISA 3 days after stimulation.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Definitions

The term "adjuvant" as used herein refers to any agent or entity which increases the antigenic response by a cell or a subject to a target antigen.

As used herein, the term "pathogen" refers to an organism or molecule that causes a disease or disorder in a subject. For example, pathogens include but are not limited to viruses, fungi, bacteria, parasites and other infectious organisms or molecules therefrom, as well as taxonomically related macroscopic organisms within the categories algae, fungi, yeast and protozoa or the like.

As used herein, the term "prokaryotic pathogen" refers to a bacterial pathogen.

As used herein, the term "viral pathogen" refers to a virus that causes illness or disease, such as HIV.

As used herein, the term "parasitic pathogen" refers to a microorganism that is parasitic, residing for an extended period inside a host cell or host organism, that gains benefits from the host and at the same time causes illness or disease. A parasitic pathogen can be bacteria, viruses, fungi, and parasites, and protists.

The term "functional fragment" as used in the context of a functional fragment of an immunogen of protein "x" (e.g., an immunogen listed Table 1) refers to a fragment of such a protein or peptide that mediates, effects or elicits a cellular and/or humoral immune response as similar to the protein or peptide from which it was derived.

A "fragment" of an antigen or immunogen of Table 1 as that term is used herein will be at least 15 amino acids in length, and can be, for example, at least 16, at least 17, at least 18, at least 19, at least 20 or at least 25 amino acids or greater.

The term "Cytotoxic T Lymphocyte" or "CTL" refers to lymphocytes which induce apoptosis in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells.

The term "cell mediated immunity" or "CMI" as used herein refers to an immune response that does not involve antibodies or complement but rather involves the activation of macrophages, natural killer cells (NK), antigen-specific cytotoxic T-lymphocytes (T-cells), and the release of various cytokines in response to a target antigen. Stated another way, CMI refers to immune cells (such as T cells and lymphocytes) which bind to the surface of other cells that display the antigen (such as antigen presenting cells (APS)) and trigger a response. The response can involve either other lymphocytes and/or any of the other white blood cells (leukocytes) and the release of cytokines. Accordingly, cell-mediated immunity (CMI) is an immune response that does not involve antibodies but rather involves the activation of macrophages and NK-cells, the production of antigen-specific cytotoxic T-lymphocytes, and the release of various cytokines in response to an antigen. Cellular immunity protects the body by: (i) activating antigen-specific cytotoxic T-lymphocytes (CTLs) that are able to destroy body cells displaying epitopes of foreign antigen on their surface, such as virus-infected cells, cells with intracellular bacteria, and cancer cells displaying tumor antigens; (2) activating macrophages and NK cells, enabling them to destroy intracellular pathogens; and (3) stimulating cells to secrete a variety of cytokines that influence the function of other cells involved in adaptive immune responses and innate immune responses. Without wishing to be bound by theory and by way of background, the immune system was separated into two branches: humoral immunity, for which the protective function of immunization could be found in the humor (cell-free bodily fluid or serum) and cellular immunity, for which the protective function of immunization was associated with cells.

The term "immune cell" as used herein refers to any cell which can release a cytokine in response to a direct or indirect antigenic stimulation. Included in the term "immune cells" herein are lympocytes, including natural killer (NK) cells, T-cells (CD4+ and/or CD8+ cells), B-cells, macrophages and monocytes, Th cells; Th1 cells; Th2 cells; Tc cells; stromal cells; endothelial cells; leukocytes; dendritic cells; macrophages; mast cells and monocytes and any other cell which is capable of producing a cytokine molecule in response to direct or indirect antigen stimulation. Typically, an immune cell is a lymphocyte, for example a T-cell lymphocyte.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Antigen Discovery Method

Two approaches proposed thus far to expand pneumococcal vaccination are based on protein subunit vaccines composed of purified pneumococcal antigens and/or on killed whole cell vaccines such as a whole cell vaccine (WCV) candidate.

Work on the pneumococcal whole cell vaccine candidate (WCV) has included transition towards GMP grade production. During this process, organic solvents were explored as an alternative to ethanol killing. It was discovered, surprisingly, that WCV killed with chloroform (WCC) was 100

1000× more potent than the ethanol-killed WCV. Additionally, when lyophilized WCC was reconstituted and spun down, the supernatant alone was highly protective in an animal colonization model. This lead to the hypothesis that the use of chloroform, which simply sublimates away during freezing and lyophilization, maintained soluble protective proteins of the WCV that were otherwise washed away after ethanol killing. The proteins in the WCC supernatant that contributed to its immunogenicity and protective capacities were then further characterized.

Thus, the present invention provides for methods for identifying antigenic candidates for vaccines. First, possible protective antigens are identified by killing a pathogen (e.g., an infectious bacteria such as pneumococcus or an infectious virus such as influenza) with one or more solvents, or organic solvents.

In some embodiments, suitable solvents include, among others, common solvents used in biological purification procedures, such as chloroform or trichloroethylene, TCE. Accordingly, in some embodiments, solvent is an organic solvent. The term "organic solvent" is an art recognized term and generally refers to a solvent which belongs to the group of organic compounds and is generally used for the dissolution of organic materials. Organic solvents include, but are not limited to, hydrocarbons, aromatic hydrocarbon, esters, ethers, halohydrocarbons, amines, amides, alkanolamides, ureas, alcholols, glycols, polyhydric alcohols, glycol ethers, glycol ether esters, and mixed solvents of two or more thereof.

Exemplary organic solvents include, but are not limited to, without limitation, 1-butanol, 2-butanol, 2-butanone, Acetamide MEA (Witco Corporation, Greenwich, Conn.), acetone, acetonitrile, and n-methyl pyrrolidone, benzene, carbon tetrachloride, chlorobenzene, chloroform, cycloheptane, cyclohexane, cyclopentane, decane, dibutyl ether, dichlorobenzenes, dichloroethanes, 1,2-dichloroethane, dichloromethane (DCM), diethanolamine, diethylene glycol, diethylene glycol monomethyl ether, diglyme (diethylene glycol dimethyl ether), diglycerol, 1,2-dimethoxy-ethane (glyme, DME), dimethylether, dimethylsulfoxide (DMSO), dioxane, dipropylene glycol monomethyl ether, dodecane, ethanolamine, ethyl acetate, ethyl propionate, ethylene glycol, ethylene glycol monophenyl ether, formic acid, glycerin, glycerol, heptane, Hexamethylphosphoramide (HMPA), hexamethylphosphorotriamide (HMPT), hexane, isopropanol, methanol, methyl acetate, methul t-butyl ether (MTBE), methyl ethyl ketone (MEK), methyl propionate, N-methyl-2-pyrrolidinone (NMP), N,N,N',N'-tetramethylurea, N,N-dimethylformamide (DMF), nitromethane, n-butanol, octane, pentane, petroleum ether (ligorine), polyethylene glycol, polypropylene glycol, 1-propanol, 2-propanol, pyridine, propylene glycol, propylene glycol monomethyl ether, propylene glycol monomethyl ether acetate, Schercomid AME-70 (Scher Chemicals, Inc., Clifton, N.J.), sorbitol, squalane, diethyl ether, t-butyl alcohol, tetrachloroethanes, tetrahydrofuran, tetrahydrofuran (THF), thiourea, toluene, trichloroethanes, triethanolamine, triethylene glycol, triglycerol, urea, xylene (o-, m- or p-), γ-butyrolactam, and mixture of two or more thereof. Other examples of organic solvents can be found, for example, in McCutcheon's Volume 2: Functional Materials, North American Edition (The Manufacturing Confectioner Publishing Co., 2006) and Vogel's Practical Organic Chemistry (Prentice Hall, $5^{th}$ ed., 1996), content of both which is incorporated herein by reference in their entirety.

Other solvents which can be used include, but are not limited, to ester solvents such as methyl laurate, isopropyl laurate, isopropyl palmitate, isostearyl palmitate, methyl oleate, isopropyl oleate, butyl oleate, methyl linoleate, isobutyl linoleate, ethyl linoleate, isopropyl isostearate, methyl soybean oil, isobutyl soybean oil, methyl tallate, isobutyl tallate, di-isopropyl adipate, di-isopropyl sebacate, diethyl sebacate, propylene glycol monocaprate, trimethylolpropane tri-2-ethylhexanoate and glyceryl tri-2-ethylhexanoate; alcohol solvents such as isomyristyl alcohol, isopalmityl alcohol, isostearyl alcohol and oleyl alcohol; higher fatty acid solvents such as isononanoic acid, isomyristic acid, hexadecanoic acid, isopalmitic acid, oleic acid and isostearic acid; and ether solvents such as diethylene glycol monobutyl ether, ethylene glycol monobutyl ether, propylene glycol monobutyl ether, and propylene glycol dibutyl ether can be employed.

In some embodiments, the solvent is not an alcohol. Preferably, the solvent is not ethanol.

The organic solvent or solvents can be removed by methods known in the art to evaporate or sublime organic fractions in mixtures, e.g., by lyophilyzation. The remaining materials are re-hydrated by adding water or other suitable aqueous solution. This process releases various antigens in the liquid phase, which can then be harvested by any methods common in the art, for example, by centrifugation or other phase separation techniques, and collection of supernatants. Additionally, various antigens that are not released in the liquid phase may be extracted by treatment of the remaining centrifuged portion with extraction techniques such as application of organic solvents, acids or bases, re-precipitation techniques, physical homogenization and/or separation, further fraction dispersion techniques, or other methods known in the art to fractionate and isolate components of solid centrifuged masses.

This method has led to surprising and important results. In the case of pneumococci, the soluble fraction of the chloroform killed bacterial preparation was one-hundred-times more protective than preparation in which the soluble fraction was washed away. Without being bound by theory, killing with chloroform or a similar solvent may uncover protective antigens that have not been identified when more traditional killing techniques (e.g., heat, ethanol, formalin), are used. Importantly, this process may be superior to more traditional techniques due to the preservation of antigens in the working mixtures. For example, it is likely that some antigens are washed away during processes that require an early supernatant washing step such as ethanol killing. It is also probable that techniques based on temperature, such as heat killing, may induce denaturation or aggregation of some antigens. Further, chemicals such as formalin have undesirable properties such as crosslinking and aggregating biological macromolecules. The present method herein maintains fractions in common solvents, e.g., organic solvents, and thus may avoid some of these potential issues.

Importantly, this method is not based on the mode of immunogenicity of the molecules identified. Therefore, the method allows for the isolation and identification of any type of microbial biological molecule that might elicit an immune response, including proteins, carbohydrates, lipids, nucleic acids, or small molecules. Any of these types of macromolecules that are not removed with the original organic solvent have the potential to serve as novel antigens. This method is also agnostic to the normal organismal location of the molecule, and therefore allows for identification of antigens that are external (e.g. surface expressed, secreted, etc.), internal (e.g. cytoplasmic, organelle-associated, etc.), membrane bound, or capsular (associated with pathogen encapsulation layer).

Additionally, this method is not based on specific pathogen characteristics, and therefore has broad applicability to various pathogens. For example, the present method may be used to identify novel antigens from bacteria, viruses, fungi, and parasites. Non-limiting examples of the antigen discovery method of the present invention includes identifying antigens from pathogenic bacteria and viruses including Staphylococci (including MRSA), Streptococci species (including Group A and B), *Brucella*, Enterococci species; *Listeria*, *Bacillus* (including anthrax), *Corynebacteria*, *Neisseria meningitidis*, *Neisseria gonorrheae*, *Moraxella*, typeable or nontypeable *Haemophilus*, *Haemophilus* nontypeable, *Pseudomonas aeruginosa* and others, *Salmonella typhi*, non-typhi *Salmonella*, *Shigella*, *Enterobacter, Citrobacter, Klebsiella, E. coli, Clostridia, Bacteroides, Chlamydiaceae, Mycoplasma, Legionella, Treponemes, Borrelia, Candida* or other yeast or other fungi, *Plasmodium, Amoeba*, herpes viruses, cytomegalovirus, Epstein-barr virus, varicella-zoster virus, influenza, adenoviruses, enteroviruses, or hemorrhagic viruses.

In some embodiments, the methods as disclosed herein can be used to identify novel immunogens and antigens from viral, bacterial, parasitic, and tumor associated antigens. In some embodiments, preferred viral antigens include proteins from any virus where a cell-mediated immune response is desired. In some embodiments, the methods as disclosed herein can be used to identify immunogens and antigens from viruses such as HIV-1, HIV-2, hepatitis viruses (including hepatitis B and C), Ebola virus, West Nile virus, and herpes virus such as HSV-2, or bacterial antigens, e.g., from *S. typhi* and Mycobacteria (including *M. tuberculosis*). In some embodiments, the methods as disclosed herein can be used to identify novel parasitic immunogens and antigens, including those from *Plasmodium* (including *P. falciparum*). An antigen can also include, for example, pathogenic peptides, toxins, toxoids, subunits thereof, or combinations thereof (e.g., tetanus, diphtheria toxoid, cholera subunit B, etc.).

In some embodiments, the methods as disclosed herein can be used to identify novel immunogens and antigens associated with a pathology, for example an infectious disease or pathogen, or cancer or an immune disease such as an autoimmune disease.

In some embodiments, the methods as disclosed herein can be used to identify novel immunogens and antigens from a whole virus or an attenuated virus, where an attenuated virus is a non-live or inactive virus.

Plotkin and Mortimer (1994) provide antigens which can be used to vaccinate animals or humans to induce an immune response specific for particular pathogens, as well as methods of preparing antigen, determining a suitable dose of antigen, assaying for induction of an immune response, and treating infection by a pathogen (e.g., bacterium, virus, fungus, or parasite).

Target bacteria for use in the methods as disclosed herein include, but are not limited to: anthrax, *campylobacter*, cholera, diphtheria, enterotoxigenic *E. coli*, giardia, gonococcus, *Helicobacter pylori* (Lee and Chen, 1994), *Hemophilus influenza* B, *Hemophilus influenzanon*-typable, meningococcus, pertussis, *pneumococcus, salmonella, shigella, Streptococcus* B, group A *Streptococcus*, tetanus, *Vibrio cholerae, yersinia, Staphylococcus, Pseudomonas* species and Clostridia species.

Target viruses for use in the methods as disclosed herein include, but are not limited to: adenovirus, dengue serotypes 1 to 4 (Delenda et al., 1994; Fonseca et al., 1994; Smucny et al., 1995), ebola (Jahrling et al., 1996), enterovirus, hepatitis serotypes A to E (Blum, 1995; Katkov, 1996; Lieberman and Greenberg, 1996; Mast, 1996; Shafara et al., 1995; Smedila et al., 1994; U.S. Pat. Nos. 5,314,808 and 5,436,126), herpes simplex virus 1 or 2, human immunodeficiency virus (Deprez et al., 1996), influenza, Japanese equine encephalitis, measles, Norwalk, papilloma virus, parvovirus B19, polio, rabies, rotavirus, rubella, rubeola, vaccinia, vaccinia constructs containing genes coding for other antigens such as malaria antigens, varicella, and yellow fever.

Target parasites for use in the methods as disclosed herein include, but are not limited to: *Entamoeba histolytica* (Zhang et al., 1995); *Plasmodium* (Bathurst et al., 1993; Chang et al., 1989, 1992, 1994; Fries et al., 1992a, 1992b; Herrington et al., 1991; Khusmith et al., 1991; Malik et al., 1991; Migliorini et al., 1993; Pessi et al., 1991; Tam, 1988; Vreden et al., 1991; White et al., 1993; Wiesmueller et al., 1991), *Leishmania* (Frankenburg et al., 1996), Toxoplasmosis, and the Helminths.

In some embodiments, the methods as disclosed herein can be used to identify antigens and immunogens used in biological warfare, e.g., ricin and anthrax, for which protection can be achieved via antibodies.

In one embodiment, the methods as disclosed herein can be used to identify antigens and immunogens which are an intracellular pathogen. A pathogen is a microorganism capable of causing damage to the host. An intracellular pathogen is a microorganism that can gain entry into the interior of a cell, live inside host cells and cause damage to the host and/or host cells. For example, the pathogen can be phagocytosed and/or endocytosed by a host cell, followed by the pathogen's escape from the phagosome or endosome. The pathogen then resides intracellularly to evade other/subsequent host defense, such as antibodies, and to multiply. Phagocytosis by macrophages is a primary frontline host defense mechanism against pathogens. When a pathogen fails to escape from the phagosome or endosome, the phagocytosed or engulfed pathogen is digested by the enzymes coming from the lysosomes. The digested, smaller peptides derived from pathogen proteins are complexed with host cell MHC molecules and displayed extracellularly to other immune cells in the host so as to stimulate the immune system of the host to respond to that particular pathogen. Intracellular pathogens include but are not limited to viruses, certain bacteria and certain protozoa. They cause a range of human diseases and ailments: tuberculosis, leprosy, typhoid fever, bacillary dysentery, plague, brucellosis, pneumonia, typhus; Rocky Mountain spotted fever, *chlamydia*, trachoma, gonorrhea, Listeriosis, scarlet/rheumatic fever, "strep" throat, hepatitis, AIDS, congenital viral infections, mononucleosis, Burkitts lymphoma and other lymphoproliferative diseases, cold sores, genital herpes, genital warts, cervical cancer, leishmaniasis, malaria, and trypanosomiasis to name but a few.

In one embodiment, the methods as disclosed herein can be used to identify antigens and immunogens from a prokaryotic pathogen, e.g., a prokaryotic pathogen is a bacterium. In one embodiment, the intracellular prokaryotic pathogen includes but not limited to *Mycobacterium tuberculosis, Mycobacterium leprae, Listeria monocytogenes, Salmonella typhi, Shigella dysenteriae, Yersinia pestis, Brucella* species, *Legionella pneumophila, Rickettsiae, Chlamydia, Clostridium perfringens, Clostridium botulinum, Staphylococcus aureus, Treponema pallidum, Haemophilus influenzae, Treponema pallidum, Klebsiella pneumoniae, Pseudomonas aeruginosa, Cryptosporidium parvum, Streptococcus pneumoniae, Bordetella pertussis*, and *Neisseria*

*meningitides Leishmania donovanii, Plasmodium species, Pneumocystis carinii, Trypanosoma species, P. falciparum, Plasmodimn sporozoites*, which leads to malaria.

In one embodiment, the methods as disclosed herein can be used to identify antigens and immunogens from a viral pathogen, e.g., which includes but is not limited to Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, poliovirus, Rhinovirus, Coronavirus, Influenza virus A, Influenza virus B. Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Rabies virus, Human T-cell Leukemia virus type-1, Hantavirus, Rubella virus and Simian Immunodeficiency virus.

In one embodiment, the methods as disclosed herein can be used to identify antigens and immunogens from tumor cells, as many tumors are associated with the expression of a particular protein and/or the over-expression of certain proteins. In such an embodiment where the antigen is a tumor antigen, a tissue sample, e.g., cancer biopsy sample can be added to the solvent. For example, prostate cancer is associated with elevated levels of protein such as Prostate Specific Antigen (PSA). Breast cancers can be associated with the expression and/or over-expression of protein such as Her-2, Muc-1, CEA, etc. Thus, considerable attention has been aimed at trying to generate immune responses to such antigens in the treatment of such malignancies. Tumors with tumor antigens include those epitopes which are recognized in eliciting T cell responses, including but not limited to the following: prostate cancer antigens (such as PSA, PSMA, etc.), breast cancer antigens (such as HER2/neu, mini-MUC, MUC-1, HER2 receptor, mammoglobulin, labyrinthine, SCP-1, NY-ESO-1, SSX-2, N-terminal blocked soluble cytokeratin, 43 kD human cancer antigens, PRAT, TUAN, Lb antigen, carcinoembryonic antigen, polyadenylate polymerase, p53, mdm-2, p21, CA15-3, oncoprotein 18/stathmin, and human glandular kallikrein), melanoma antigens, and the like.

As disclosed herein, the present unique method has identified novel T-cell antigens to pneumococci. Accordingly, the methods as disclosed herein can be particularly useful for antigen discovery in pathogens that require T-cell in addition to B-cell response. Therefore, pathogen targets of the present invention include those known or discovered to require T-cell or more specifically Th17 cell activity, including *S. aureus, C. trichomatis, M tuberculosis*, viruses such as Herpes simplex virus, and others.

In order to confirm immunogenicity of the novel fractions, the liquid fraction can then be size-fractionated or separated by preparative SDS gel or other methods, following which individual fractions are evaluated for immune stimulation in a variety of assays. Example assays include those to directly measure antibody or T-cell responses, such as ELISA assays, cell sorting procedures, neutralization assays, or others known in the art. Additionally, it is potentially useful to monitor production of markers or secretions of cell-types, such as cytokines. Example assays include T cell assays, such as elicitation of IL-17A from immune animals, or the monitoring of other cytokines such as IFN-gamma, IL-4, etc., that can identify those fractions to which antibodies from immune animals bind strongly. The most-promising fractions may then be evaluated further to identify components, e.g., by mass spectroscopy or other techniques. Proteins can then be evaluated singly to determine which are immunogenic and protective. Since the separation isolation method of invention can be flexibly coupled to the immune system endpoints above, the method of the invention is useful to identify antigens that can be immunogenic in a variety of ways, including T-cell effector subtypes, antibody responses, or other adaptive or innate immune mechanisms.

The unique method has identified novel pneumococcal antigens, and demonstrates the utility of the approach to uncover novel immunogens from well-studied pathogens.

Novel Pneumococcal Antigens

One mechanism of protection against pneumococcal colonization has been elucidated with a WCV candidate that confers protection against both colonization and invasive disease in mice. (Malley et al., 69 Infect. Immun. 4870-73 (2001); Malley et al., 74 Infect. Immun. 4290-92 (2004).). Protection against colonization following immunization with WCV is antibody-independent and dependent on CD4+ T cells (Malley et al., 102 P.N.A.S. USA 102, 4848-53 (2005); Trzcinski et al., 73 Infect. Immun. 7043-46 (2005)). The effector T cell is the CD4+ TH17 cell: neutralization of IL-17A with anti IL-17A antibodies diminishes protection by the WCV and Il-17A receptor knockout mice are not protected by the WCV. In contrast, IFN-gamma or IL-4 deficient mice (which are skewed away from THI or TH2 responses, respectively) are fully protected (Lu et al., 4 PLoS Pathogens. e1000159 (2008)). Rats and mice immunized with the WCV are also significantly protected against pneumococcal sepsis in two pneumonia models (Malley et al., 2001).

This unique, sequential method described above has herein identified novel pneumococcal T-cell antigens. These antigens, administered as mucosal vaccines with a cholera toxin adjuvant, elicit systemic IL17A and reduce or protect against intranasal pneumococcal colonization. More specifically, SPN2070 was completely protective. Both SPN0862 and SPN1534, although not fully protective, significantly reduced colonization.

It is feasible that a pneumococcal protein subunit vaccine would contain several antigens and/or be formulated with different or novel adjuvants, or incorporated in vaccine scaffolds, such as a fusion-conjugate (e.g., a fusion with a pneumolysoid and conjugation to a polysaccharide as proposed in Lu et al, Infection and Immunity, 2009) to improve immunogenicity and facilitate different routes of administration. Accordingly, a composition comprising at least 2, or at least about 3, or at least about 4, or at least about 5, or at least about 6, or at least about 7, or at least about 8, or at least about 9, or at least about 10, or at least about 12, or at least about 14, or at least about 16, or at least about 18, or at least about 20, or at least about 25, or any integer between about 2 and about 26 different antigens or more that 25 different antigens can be used, alone or in combination with an adjuvant and/or vaccine scaffold, such as a polysaccharide can be used.

Several eluates with robust stimulatory potential were identified from the method applied to pneumococcus, yielding WCC. Of the fourteen eluates collected representing separation of the WCC supernatant, the nine eluates containing clear protein bands were used as stimuli. Several eluates clearly emerged as having higher potential to elicit Th17 cell activation. Data from these stimulations are depicted in FIG. 1. The predominant band(s) of the most stimulatory eluates (such as 9 and 10) were submitted for mass spectroscopy analysis.

Figure 2:
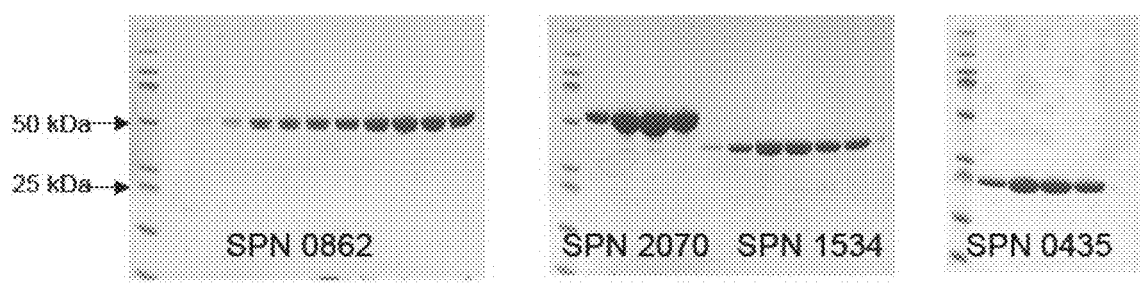
FIG. 2 shows gels from the purification of individual proteins from *E. coli*. Proteins were cloned into competent *E. coli* cells using the pQE-30 plasmid; transformants were verified by sequencing. Proteins were expressed in successful transformants and pelleted. After lysing by sonication, his-tagged proteins in the cell lysis supernatant were purified over an agarose-Ni column. Eluted proteins were then desalted over a PD10 column and again purified by size exclusion gel filtration. Representative proteins are depicted on Coomassie stained SDS-PAGE gels.

Mass spectroscopy identified multiple proteins within each band (range 13-23), but with some overlap in adjacent eluates. A compilation of data from mass spectroscopy analysis was used to generate a table of over forty proteins that were contained within the stimulatory WCC supernatant eluates which are listed in Table 1). Based on clinical safety criteria such as lack of human homology and conservation across all twenty-two sequenced pneumococcal strains, this panel was narrowed to twelve proteins. These proteins were then expressed and purified in an *E. coli* expression system. Protein gels of the purified proteins yielded single bands (FIG. 2) demonstrating successful purification.

TABLE 1

Proteins identified by mass spectroscopy within protein bands of stimulatory eluates. Pneumococcal T-cell antigens with multiple GI numbers were identified in multiple adjacent bands. Number of peptide matches refers to the number of unique peptide matches for a given protein within a sample. (Identifying >2 peptide matches confers a confident protein match).

| TIGR4 Antigen | GI number | Proposed function | Number peptide matches | Publications | Homology w/ human peptides | *E. coli* Homology | Location |
|---|---|---|---|---|---|---|---|
| Stimulatory eluate 6 (3/11 and 3/18 eluates submitted) | | | | | | | |
| SP0499 | 57014092 46576835 | Phosphoglycerate kinase | 14 and 3 2 | | 45% hum hom | | Cytosolic |
| SP1128 | 122278628 29839238 | Phosphopyruvate hydratase (enolase) | 13 and 9 1 and 1 | Ling et al. | ++ (hum hom) | | |
| SP1489 | 57015312 | Translation elongation factor Tu | 11 and 10 | | 30-40% hum hom | | Cytosolic |
| | 54040967 | | 4 and 4 | | | | |
| | 26006962 | | 2 and 2 | | | | |
| SP0862 | 149021729 157149853 | 30S ribosomal protein S1 | 4 and 4 2 and 1 | Touanemen (microarray expression analysis) | None | 33% | Cytosolic |
| SP2070 | 31076701 157149825 116248080 | glucose-6-phosphate isomerase | 3 and 2 1 and 1 1 and 1 | Ling et al. | None | 25% | Cytosolic |
| SP1666 | 149021240 157150730 | cell division protein FtsZ | 3 and 1 2 and 2 | | None | | Cytosolic |
| SP1508 | 118573765 157151073 | ATP synthase subunit B | 1 and 1 1 and 1 | | 53% hum hom | | |
| SP0375 | 157150360 | 6-phospho-gluconate dehydrogenase | 1 and 3 | | 40% hum hom | | Surface |
| SP0281 | | Amino-peptidase | 1 | Ling et al. | None | | Cytosolic |
| Stimulatory eluate 10 | | | | | | | |
| SP1572 | 149022042 | non-heme iron-containing ferritin | 3 | See Zhu (PppA) | None | 26% | Cytosolic |
| SP1297 | 149019295 | flavodoxin | 2 | None | None | 28% | Cytosolic |
| SP0225 | 81775698 | 50s ribosomal protein | 1 | | None | 46% | Cytosolic |
| SP0221 | 50401285 | 50s ribosomal protein | 1 | | None | 58% | Cytosolic |
| SP2007 | 157150102 149020768 | Transcription anti-termination factor NusG | 1 1 | | None | 36% | Cytosolic |
| SP1540 | 73919454 | single-strand DNA-binding protein | 1 | | None | 30% | Cytosolic |
| SP1583 | 149022052 | isochorismatase family protein | 1 | | None | 36% | Cytosolic |
| Stimulatory eluate 8 (4/23 eluate submitted) | | | | | | | |
| SP 0605 | 61218411 | Fructose-bisphosphate aldolase | 8 | | None | | Cytosolic |
| SP1534 | 54041722 73921762 | putative manganese-dependent inorganic pyrophosphatase | 5 1 | U.S. Pat. No. 10/567,570 antibiotic | None | 0% | Cytosolic |
| SP2012 | 157151535 81175319 | glyceraldehyde-3-phosphate dehydrogenase | 4 3 | | >40% hum hom | | Cytosolic |
| SP2215 | 61215772 | 30S ribosomal protein S2 | 3 | | | 50% | Cytosolic |
| SP1458 | 149019403 | thioredoxin reductase | 2 | U.S. Pat. No. 10/567,570; Hermans: gene expression | None | 36% | Surface |
| SP1735 | 33516864 | methionyl-tRNA formyltransferase | 2 | | None | 41% | Cytosolic |
| SP0946 | 149019536 | hypothetical protein | 1 | None | None | 0 | Cytosolic |
| SP1220 | 118601094 | L-lactate dehydrogenase | 1 | | 38% hum hom | | Surface |

TABLE 1-continued

Proteins identified by mass spectroscopy within protein bands of stimulatory eluates. Pneumococcal T-cell antigens with multiple GI numbers were identified in multiple adjacent bands. Number of peptide matches refers to the number of unique peptide matches for a given protein within a sample. (Identifying >2 peptide matches confers a confident protein match).

| TIGR4 Antigen | GI number | Proposed function | Number peptide matches | Publications | Homology w/ human peptides | E. coli Homology | Location |
|---|---|---|---|---|---|---|---|
| SP2092 | 81170781 | UTP-glucose-1-phosphate uridylyl transferase | 1 | US Pat. Serial No. 10/552,156; US Pat. Serial No. 10/567,570 | None | 44% | Surface |
| SP2210 | 149020129 | cysteine synthase | 1 | | <10% hum hom | 44% | Cytosolic |
| Stimulatory eluate 9 (combined 3/18-24 eluate) | | | | | | | |
| SP1415 | 15901269 | N-acetylgluco-samine-6-phosphate isomerase | 7 | See Hendriksen et al., CodY paper | <10% hum hom | 32% | Cytosolic |
| SP1574 | 15901416 | triosephosphate isomerase | 5 | | +++ (hum hom) | | |
| SP0421 | 15900340 | 3-ketoacyl-(acyl-carrier-protein) reductase | 5 | | >40% hum hom | | |
| SP1655 | 15901490 | Phosphoglyceromutase | 4 | | +++ (hum hom) | | |
| SP0516 | 15900430 | heat shock protein GrpE | 4 | See Hendriksen et al. | None | 28% | Cytosolic |
| SP0435 | 15900353 | elongation factor P | 3 | US Pat. Appl No. US2007/0184443 A1 | None | 33% | Cytosolic |
| SP1733 | 15901565 | phosphatase, putative | 3 | None | None | 0 | Cytosolic |
| SP1572 | 15901415 | non-heme iron-containing ferritin | 3 | | See eluate 10 | | |
| SP0427 | 15900346 | acetyl-CoA carboxylase alpha subunit | 3 | | None | 46% | Cytosolic |
| SP0945 | 15900824 | ribosome releasing factor | 2 | | None | 45% | Cytosolic |
| SP0215 | 15900151 | 30S ribosomal protein S3 | | | | | |
| SP1776 | 15901605 | thioredoxin | | | 34% hum hom | | Cytosolic |

Figure 3:
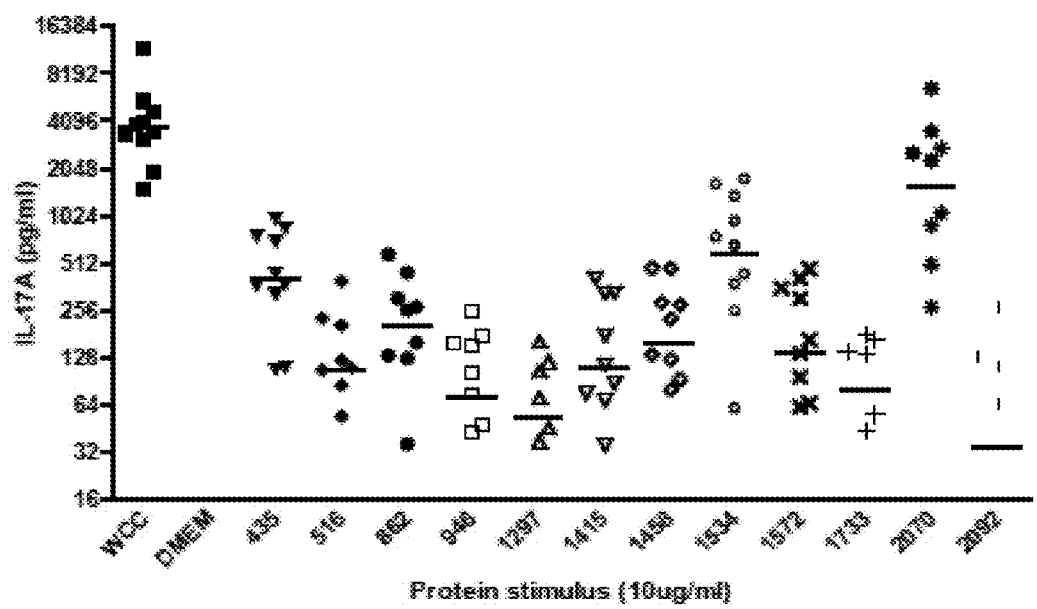
FIG. 3 shows data from the stimulation of IL-17A production by purified proteins. Twelve proteins (SP435, SP516, SP862, SP946, SP1297, SP1415, SP1458, SP1538, SP1572, SP1733, SP2070 and SP2092 were selected from all of the proteins identified by Mass spectroscopy (see table 1) and cloned into and purified from *E. coli*. Splenocytes from WCC immunized mice (n=10) were stimulated with 10 µg/ml of each protein and IL-17A production was measured 6 days after stimulation. Bars represent median values for each stimulus. Each animal's IL-17A response to stimulation with DMEM media was considered background, and was therefore subtracted from the IL-17A values from protein stimuli.

Immunogenic purified proteins were next identified by determining which purified proteins elicited the highest IL-17A response from splenocytes of WCC immunized mice, thus prioritizing the antigens that would move into animal immunization models. As shown in FIG. 3, several proteins met this criterion (SPN2070 (SEQ ID NO: 10; SEQ ID NO: 11), SPN1534 (SEQ ID NO: 28; SEQ ID NO: 29), SPN0435 (SEQ ID NO: 44) and SPN0862 (SEQ ID NO: 8; SEQ ID NO: 9)). Though not meeting the self-imposed criterion, and thus not tested for protection, SPN516 (SEQ ID NO: 43), SPN862 (SEQ ID NO: 8 and 9), SPN946 (SEQ ID NO: 35), SPN1297 (SEQ ID NO: 20), SPN1415 (SEQ ID NO: 38), SPN1458 (SEQ ID NO: 33), SPN1572 (SEQ ID NO: 19), and SPN1733 (SEQ ID NO: 35) were also identified as novel pneumococcal antigens able to elicit immunogenic responses. Additionally, the protein SPN2092 showed minimal stimulatory potential; as a protein expressed and purified by the same process, this protein would become a representative negative control in an immunization model.

This animal model of identifying pneumococcal antigens which elicited the highest IL-17A response from splenocytes of WCC immunized mice also demonstrated that a combination of at least 2 proteins protects against colonization.

Figure 4A:
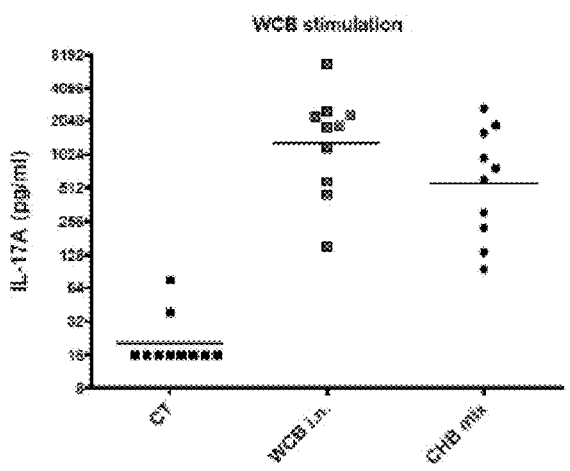
FIG. 4A-4B shows data on protection against colonization by intranasal immunization with a mixture of proteins. A mixture of 4 µg/ml of each SPN0435, SPN1534 and SPN2070 (CHB mix) was used to immunize mice twice one week apart with 1 µg of cholera toxin (CT) as adjuvant. Mice immunized with CT alone or a whole cell pneumococcal preparation with CT (WCB) constituted negative and positive controls, respectively. Blood was taken 3 weeks after second immunization.

For example, candidate proteins were first evaluated using a combination vaccine comprising at least three antigens that were most stimulatory in the splenocyte stimulations (FIG. 3). When the whole blood of immunized animals was stimulated with the whole cell antigen the immunogenicity of this combination vaccine comprising antigens SPN0435 (SEQ ID NO: 44), SPN1534 (SEQ ID NO: 28 and 29), and SPN 2070 (SEQ ID NO: 10 and 11), where the combination of such antigens is referred to as "CHB" was robust (see FIG. 4A). Extensive experience with WCV studies have indicated that post-immunization IL-17A values of 250 μg/ml in whole blood stimulated with whole cell antigen correlate well with protection from colonization (Lu et al., 2008). Animals immunized with the combination vaccine indeed were completely protected from colonization, and the combination vaccine was as protective as the WCV (see FIG. 4B).

Figure 5:
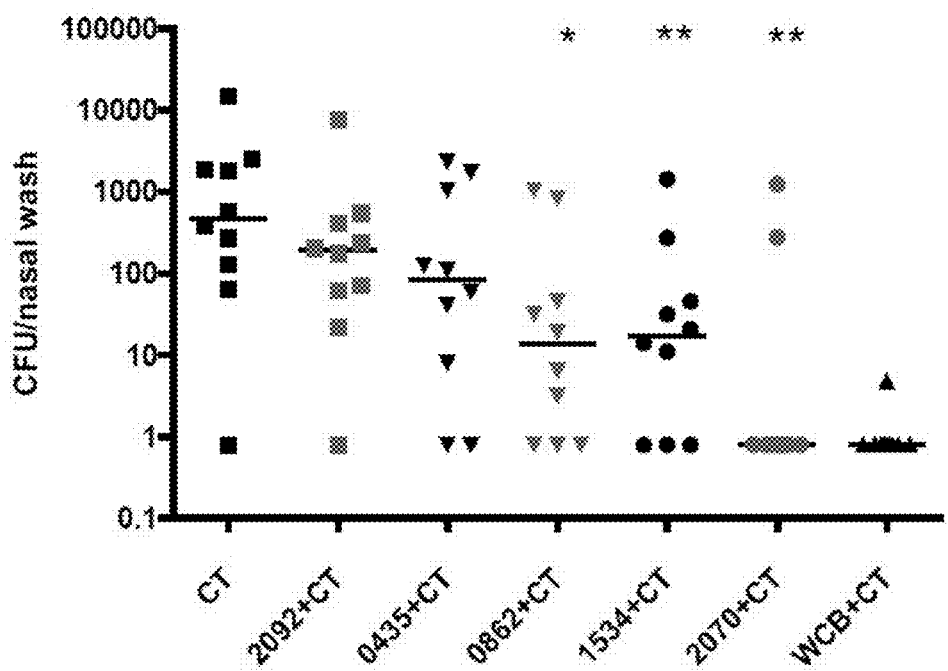
FIG. 5 shows protection against colonization by individual proteins in C57Bl/6 mice. Immunization and challenge schedule was the same as in FIG. 4. NP colonization density was compared by the Mann-Whitney U test or by the Kruskal-Wallis test with Dunn's correction for multiple comparisons using PRISM. *, $p<0.05$; **, $p<0.01$.

Additionally, individual purified protein pneumococcal antigens as disclosed in Table 1 also provided protection in a colonization model. Having shown that a combination of at least three of these pneumococcal antigen proteins protected animals from colonization, identifying the individual proteins which contributed most to this protective capacity was explored. Using each of the proteins contained within the combination, plus an additional protein that was stimulatory in the splenocyte assay (SPN0862), animals were immunized with vaccines comprised of single proteins with cholera toxin (CT). As shown in FIG. 5, SPN2070 (SEQ ID NO: 10; SEQ ID NO: 11) was highly protective, essentially as protective as WCV. Additionally, SPN1534 (SEQ ID NO: 28 and 29) and SPN0862 (SEQ ID NO: 8; SEQ ID NO: 9) conferred statistically significant reduction in colonization as compared with cholera toxin-immunized controls. Animals immunized with SPN2092 (SEQ ID NO: 37) were not protected, validating the methods used to identify and predict those proteins, chosen from a larger pool of proteins that would be immunogenic and protective.

The novel antigens described here, namely SPN2070 (SEQ ID NO: 10; SEQ ID NO: 11), SPN1534 (SEQ ID NO: 28 and 29), and SPN0862 (SEQ ID NO: 8; SEQ ID NO: 9), and SPN0435 (SEQ ID NO: 44) demonstrate the utility of the method and provide new vaccine candidates. It has been previously reported that SPN2070 might be used as a vaccine antigen, however it was previously unknown that this protein could elicit a T-cell specific response. Additionally, the remaining proteins such as SPN1534, and SPN0862 and SPN0435 as well as other listed in Table 1 which have never before been described as possible antigens for a pneumococcal vaccine. Thus, the method presented here has approached a well-studied pathogenic bacteria and been able to identify proteins previously unknown to elicit immune-cell-specific antigenic response.

Figure 4B:
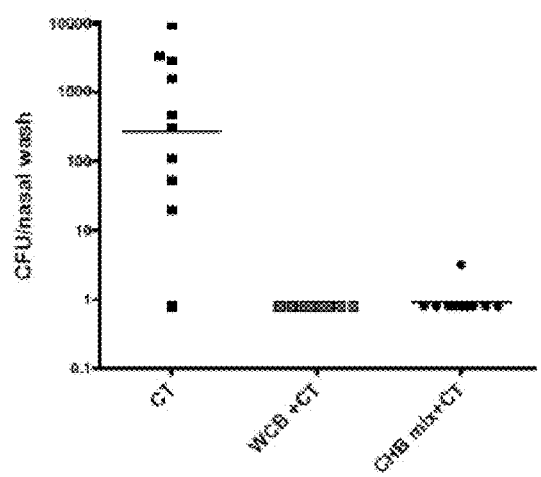
Figure 7:
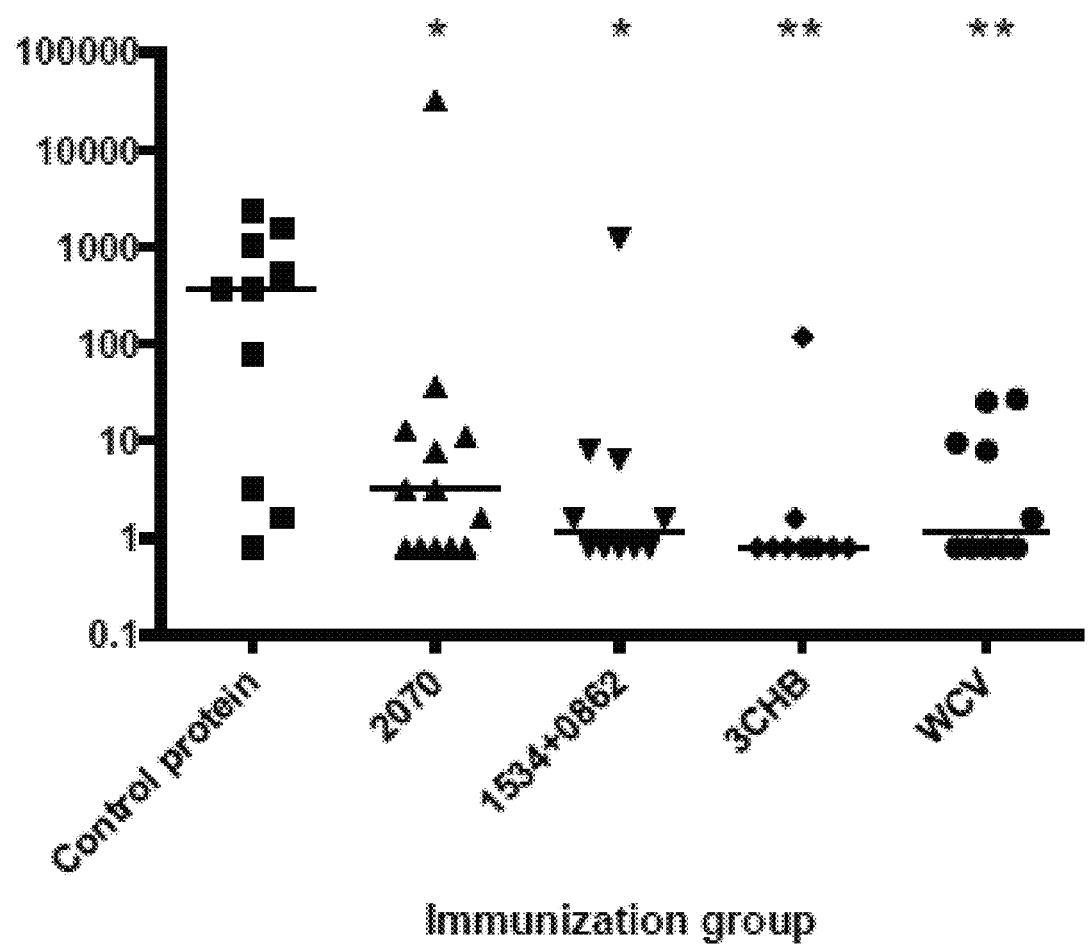
FIG. 7 shows data from stimulation of exposed mice with individual SP proteins and protection against colonization by individual proteins in CD1 mice. Immunization and challenge schedule was the same as prior. NP colonization density was compared by the Mann-Whitney U test or by the Kruskal-Wallis test with Dunn's correction for multiple comparisons using PRISM. *, $p<0.05$; , $p<0.01$, *, $p<0.001$. 2070, 1534, 0862 are all SP gene numbers. 3CHB refers to the combination of SP 2070, SP 1534, SP 0862. WCV is the whole cell vaccine which serves as a positive control.

In some embodiments, a vaccine can comprise SPN2070 antigen of SEQ ID NO: 10; SEQ ID NO: 11 or a portion or fragment thereof. In some embodiments, a vaccine can comprise a combination of at least two immunogens, such as SPN1534 and SPN0862, or a functional fragment or portion or protein with substantial identity thereof. In some embodiments, a vaccine can comprise any combination or one or more of SPN2070, SPN1534 and SPN0862 immunogens, or all three immunogens together, as disclosed in FIG. 7. In some embodiments, a vaccine comprises a combination of at least two immunogens, such as SPN1534 and SPN0862, or functional fragments or proteins with substantial identity to SPN1534 and SPN0862 alone, or in combination with one or more adjuvants and/or vaccine scaffolds, such as a polypeptide scaffold. In some embodiments, a vaccine can comprise any combination or one or more of SPN2070, SPN1534 and SPN0862, or all three immunogens SPN2070, SPN1534 and SPN0862 together, or functional fragments or proteins with substantial identity to SPN2070, SPN1534 and SPN086 alone, or in combination with one or more adjuvants (e.g., as shown in FIG. 4B) and/or in combination with a vaccine scaffold for a multivarient vaccine approach.

In some embodiments, the vaccine can comprise one or any combination of immunogens of the proteins listed in Table 2, or their functional fragments, alone, or in combination with an adjuvant and/or a vaccine scaffold to produce a multivalent vaccine.

Table2 lists the amino acid sequence identification numbers of the pneumococcal immunogens.

| TIGR4 Antigen | GI number | SEQ ID NO: | Proposed function |
|---|---|---|---|
| Stimulatory eluate 6 (3/11 and 3/18 eluates submitted) | | | |
| SP0499 | 57014092 | 1 | Phosphoglycerate kinase |
| | 46576835 | 2 | |
| SP1128 | 122278628 | 3 | Phosphopyruvate hydratase (enolase) |
| | 29839238 | 4 | |
| SP1489 | 57015312 | 5 | Translation elongation factor Tu |
| | 54040967 | 6 | |
| | 26006962 | 7 | |
| SP0862 | 149021729 | 8 | 30S ribosomal protein S1 |
| | 157149853 | 9 | |
| SP2070 | 31076701 | 10 | glucose-6-phosphate isomerase |
| | 157149825 | 11 | |
| | 116248080 | 12 | |
| SP1666 | 149021240 | 13 | cell division protein FtsZ |
| | 157150730 | 14 | |
| SP1508 | 118573765 | 15 | ATP synthase subunit B |
| | 157151073 | 16 | |
| SP0375 | 157150360 | 17 | 6-phospho-gluconate dehydrogenase |
| SP0281 | 116516913 | 18 | Amino-peptidase |
| Stimulatory elutate 10 | | | |
| SP1572 | 149022042 | 19 | non-heme iron-containing ferritin |
| SP1297 | 149019295 | 20 | flavodoxin |
| SP0225 | 81775698 | 21 | 50s ribosomal protein |
| SP0221 | 50401285 | 22 | 50s ribosomal protein |
| SP2007 | 157150102 | 23 | Transcription anti-termination factor NusG |
| | 149020768 | 24 | |
| SP1540 | 73919454 | 25 | single-strand DNA-binding protein |
| SP1583 | 149022052 | 26 | isochorismatase family protein |
| Stumulatory elute 8 | | | |
| SP 0605 | 61218411 | 27 | Fructose-bisphosphate aldolase |
| SP1534 | 54041722 | 28 | putative manganese-dependent inorganic pyrophosphatase |
| | 73921762 | 29 | |
| SP2012 | 157151535 | 30 | glyceraldehyde-3-phosphate dehydrogenase |
| | 81175319 | 31 | |
| SP2215 | 61215772 | 32 | 30S ribosomal protein S2 |
| SP1458 | 149019403 | 33 | thioredoxin reductase |
| SP1735 | 33516864 | 34 | methionyl-tRNA formyltransferase |
| SP0946 | 149019536 | 35 | hypothetical protein |
| SP1220 | 118601094 | 36 | L-lactate dehydrogenase |
| SP2092 | 81170781 | 37 | UTP-glucose-1-phosphate uridylyl transferase |
| SP2210 | 149020129 | 38 | cysteine synthase |
| Stimulatory elutate 9 | | | |
| SP1415 | 15901269 | 39 | N-acetylgluco-samine-6-phosphate isomerase |
| SP1574 | 15901416 | 40 | triosephosphate isomerase |
| SP0421 | 15900340 | 41 | 3-ketoacyl-(acyl-carrier-protein) reductase |
| SP1655 | 15901490 | 42 | Phosphoglyceromutase |
| SP0516 | 15900430 | 43 | heat shock protein GrpE |
| SP0435 | 15900353 | 44 | elongation factor P |
| SP1733 | 15901565 | 45 | phosphatase, putative |
| SP1572 | 15901415 | 46 | non-heme iron-containing ferritin |
| SP0427 | 15900346 | 47 | acetyl-CoA carboxylase alpha subunit |
| SP0945 | 15900824 | 48 | ribosome releasing factor |
| SP0215 | 15900151 | 49 | 30S ribosomal protein S3 |
| SP1776 | 15901605 | 50 | thioredoxin |

In some embodiments, the vaccine can comprise at least one immunogen of the sequences listed in Table 2, or an immunogen which is a functional fragment or has substantial identity to an immunogen listed in Table 1 or 2.

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectively. A sequence which is "unrelated" or "non-homologous" shares less than 40% identity, though preferably less than 25% identity with the sequences as disclosed herein.

The term "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 60% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 60 at least 70%, at least 80%, at least 90%, at least 95% identical, at least 97% identical, or at least 99% identical. Determination of homologs of the genes or peptides of the present invention can be easily ascertained by the skilled artisan.

In some cases, it there may be advantages to designing vaccines based on antigens that are "surface-expressed" rather than cytoplasmic. Annotated genomes often describes protein location based on homology with other identified proteins, but this may be an imperfect or often incorrect approach, as homologous proteins form two different organisms may not necessarily be located at the same site (nor have the same function) in both. Thus, an additional tool for determination of the location of the protein (surface versus other) may be very helpful and may also be used in the chloroform method described herein.

An embodiment of the present method comprises identifying a protein, "X" of interest, then removing the gene encoding for X from the organism, then replacing that gene with a gene encoding for a tagged version of the X protein (e.g., tagged with His, HA, OVA peptide, among others), which can be detected readily with monoclonal or polyclonal antibodies. After confirmation of the genetic construct, the organism is then grown, stained with an antibody that recognizes the tag (and is also fused to a fluorophore). Flow cytometry is then used to evaluate whether the antibodies are attached to the surface of the organism, in which case, the antigen can be deduced to be surface-expressed. Similar strategies using antibodies attached to magnetic beads can be used as well. For pneumococcus, for example, the organism can be evaluated in its encapsulated or unencapsulated form. An antigen can be surface expressed, but hidden under the capsule, for selection of antigen purposes, it may be advantageous to select an antigen that is both surface expressed and accessible despite capsulation.

The identified immunogenic proteins or mixtures thereof may be used in a multivalent or individual vaccine, which can be administered in many forms (intramuscularly, subcutaneously, mucosally, transdermally). For example, combinations or permutations of the twelve pneumococcal immunogens may be more efficacious against colonization versus disease. A combination of several immunogens with both characteristics may provide a superior vaccine.

Immunogenic compositions may contain adjuvants. As shown herein, cholera toxin (CT) was used as an adjuvant for intranasal administration, resulting in protection from pneumococcal colonization. Alum is an affective adjuvant for subcutaneous injection. Adjuvants are typically a heterogeneous group of substances that enhance the immunological response against an antigen that is administered simultaneously. In some instances, adjuvants are added to a vaccine to improve the immune response so that less vaccine is needed. Adjuvants serve to bring the antigen—the substance that stimulates the specific protective immune response—into contact with the immune system and influence the type of immunity produced, as well as the quality of the immune response (magnitude or duration). Adjuvants can also decrease the toxicity of certain antigens and provide solubility to some vaccine components. Almost all adjuvants used today for enhancement of the immune response against antigens are particles or form particles together with the antigen. In the book "Vaccine Design—the subunit and adjuvant approach" (Ed: Powell & Newman, Plenum Press, 1995) almost all known adjuvants are described both regarding their immunological activity and regarding their chemical characteristics. The type of adjuvants that do not form particles are a group of substances that act as immunological signal substances and that under normal conditions consist of the substances that are formed by the immune system as a consequence of the immunological activation after administration of particulate adjuvant systems.

Adjuvants for vaccines are well known in the art. Suitable additional adjuvants include, but are not limited to: complete Freund's adjuvant (CFA), incomplete Freund's adjuvant (IFA), saponin, mineral gels such as aluminum hydroxide, surface active substances such as lysolecithin, pluronic polyols, polyaninons, peptides, oil or hydrocarbon emulsions, keyhole limpet hemocyanins, dinitrophenol, and potentially useful human adjuvants such as BCG (bacille Calmette-Guerin) and *Corynebacterium parvum*. Selection of an adjuvant depends on the animal subject to be vaccinated. Additional examples include, but are not limited to, monoglycerides and fatty acids (e. g. a mixture of monoolein, oleic acid, and soybean oil); mineral salts, e.g., aluminium hydroxide and aluminium or calcium phosphate gels; oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilised water-in-oil emulsion); particulate adjuvants, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array) and inert vehicles, such as gold particles. Newer adjuvants are described in U.S. Pat. No. 6,890,540, United States Patent Application No. 20050244420, and PCT/SE97/01003, the contents of which are incorporated herein by reference in their entirety. The adjuvant can also be selected from the group consisting of QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

In some embodiments, alternative adjuvants can be used, such as a pharmaceutically acceptable adjuvant. For example, oils or hydrocarbon emulsion adjuvants should not be used for human vaccination. One example of an adjuvant suitable for use with humans is alum (alumina gel). Details of common adjuvants which are contemplated to be added to the vaccine comprising immunogens as disclosed in Table 1 include those discussed below:

Complete Freund's Adjuvant (CFA): A mineral oil adjuvant; uses a water-in-oil emulsion which is primarily oil. For many years the adjuvant of choice was complete Freund's adjuvant. This adjuvant, while potent immunogenically, also has had a significant history of frequently producing abscesses, granulomas and tissue sloughs. It contains paraffin oil, killed mycobacteria and mannide monoosleate. The paraffin oil is not metabolized; it is either expressed through the skin (via a granuloma or abscess) or phagocytized by macrophages. Multiple exposures to CFA will cause severe hypersensitivity reactions. Accidental exposure of personnel to CFA can result in sensitization to tuberculin.

Incomplete Freund's Adjuvant (IFA): Also a mineral oil adjuvant. Composition similar to CFA but does not contain the killed mycobacteria so does not produce as severe reactions. Used for the booster immunizations following the initial injection with antigen-CFA. IFA can be used for initial injection if the antigen is strongly immunogenic.

Montanide ISA (Incomplete Seppic Adjuvant): A mineral oil adjuvant. Uses mannide oleate as the major surfactant component. The antibody response is generally similar to that with IFA. Montanide ISA may have a lessened inflammatory response.

Ribi Adjuvant System (RAS): An oil-in-water emulsion that contains detoxified endotoxin and mycobacterial cell wall components in 2% squalene. Multiple formulations are commercially available, dependent on use. Is an alternative to CFA. Lower viscosity than CFA. Results (titers) often comparable to those with CFA. The squalene oil is metabolizable. RAS has a lower incidence of toxic reactions.

TiterMax: Another water-in-oil emulsion, this preparation combines a synthetic adjuvant and microparticulate silica with the metabolizable oil squalene. The copolymer is the immunomodulator component. Antigen is bound to the copolymer and presented to the immune cells in a highly concentrated form. Less toxicity than CFA. TiterMax usually produces the same results as CFA.

Syntex Adjuvant Formulation (SAF): A preformed oil-in-water emulsion. Uses a block copolymer for a surfactant. A muramyl dipeptide derivative is the immunostimulatory component. All in squalene, a metabolizable oil. SAF can bias the humoral response to IgG2a in the mouse, but is less toxic than CFA.

Aluminum Salt Adjuvants: Most frequently used as adjuvants for vaccine antigen delivery. Generally weaker adjuvants than emulsion adjuvants. Aluminum Salt Adjuvants are best used with strongly immunogenic antigens, but result generally in mild inflammatory reactions.

Nitrocellulose-adsorbed antigen: The nitrocellulose is basically inert, leading to almost no inflammatory response. Slow degradation of nitrocellulose paper allows prolonged release of antigen. Does not produce as dramatic an antibody response as CFA. Nitrocellulose-adsorbed antigen is good for use if only a small amount of antigen can be recovered from a gel band, e.g., for animal immunization.

Encapsulated or entrapped antigens: Permits prolonged release of antigen over time; can also have immunostimulators in preparation for prolonged release. Preparation of encapsulated or entrapped antigens is complex.

Immune-stimulating complexes (ISCOMs): Antigen modified saponin/cholesterol micelles. Stable structures are formed which rapidly migrate to draining lymph nodes. Both cell-mediated and humoral immune responses are achieved. Low toxicity; ISCOMs can elicit significant antibody response. Quil A is one example, QS-21 is another.

GerbuR adjuvant: An aqueous phase adjuvant which uses immunostimulators in combination with zinc proline. GerbuR does not have a depot effect and has minimal inflammatory effect. GerbuR requires frequent boosting to maintain high titers.

Another group of adjuvants include immune stimulators such as cytokines IL-12, IL-4 and costimulatory molecules such as B7. A wide range of molecules having immune stimulating effects are known including accessory molecules such as ICAM and LFA. In some embodiments, GM-CSF is administered to the patient before the initial immune administration. GM-CSF can be administered using a viral vector or an isolated protein in a pharmaceutical formulation. Combinations of adjuvants can be used such as CM-CSF, ICAM and LFA. While a strong immune response is typically generated to infectious disease antigens, tumor associated antigens typically generate a weaker immune response. Thus, immune stimulators such as described above are preferably used with them.

Ongoing studies assess immunogenicity in outbred animal strains, and characterize the efficacy of these proteins in protecting against invasive disease in aspiration/sepsis models. In some embodiments, one can test the ability of an immunogen or vaccine composition to elicit an immune response in vivo, by measuring a CMI response to the target antigen. CMI assays are known in the art and described, for example, in United States Patent Application 2005/0014205, WO/1987/005400, U.S. Pat. No. 5,674,698 and commercially available kits such as IMMUNKNOW® CYLEX Immune cell function assay Product No. 4400, which are incorporated in their entirety by reference herein for use in the present invention.

In one embodiment, a vaccine compositions described herein comprise a pharmaceutically acceptable carrier. In another embodiment, the vaccine composition described herein is formulated for administering to a mammal. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

In one embodiment, a vaccine compositions as described herein comprise pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. Nos. 3,773,919, 3,887,699, EP 58,481A, EP 158, 277A, Canadian Patent No. 1176565; U. Sidman et al., Biopolymers 22:547 (1983) and R. Langer et al., Chem. Tech. 12:98 (1982). The proteins will usually be formulated at a concentration of about 0.1 mg/ml to 100 mg/ml per application per patient.

In one embodiment, other ingredients can be added to vaccine formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, a vaccine composition as described herein for administration must be sterile. Sterility is readily accomplished by filtration through sterile filtration membranes (e.g., 0.2 micron membranes).

In some embodiments, a vaccine composition as described herein further comprises pharmaceutical excipients including, but not limited to biocompatible oils, physiological saline solutions, preservatives, carbohydrate, protein, amino acids, osmotic pressure controlling agents, carrier gases, pH-controlling agents, organic solvents, hydrophobic agents, enzyme inhibitors, water absorbing polymers, surfactants, absorption promoters and anti-oxidative agents. Representative examples of carbohydrates include soluble sugars such as hydropropyl cellulose, carboxymethyl cellulose, sodium carboxyl cellulose, hyaluronic acid, chitosan, alginate, glucose, xylose, galactose, fructose, maltose, saccharose, dextran, chondroitin sulfate, etc. Representative examples of proteins include albumin, gelatin, etc. Representative examples of amino acids include glycine, alanine, glutamic acid, arginine, lysine, and their salts.

In some embodiments, the immunogens as described herein can be solubilized in water, a solvent such as methanol, or a buffer. Suitable buffers include, but are not limited to, phosphate buffered saline $Ca^{2+}/Mg^{2+}$ free (PBS), normal saline (150 mM NaCl in water), and Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH may be used as a diluent after solubilization in dilute acetic acid. Glycerol can be a suitable non-aqueous buffer for use in the present invention.

If the immunogen as disclosed herein is not soluble per se, the immunogen can be present in the formulation in a suspension or even as an aggregate. In some embodiments, hydrophobic antigen can be solubilized in a detergent, for example a polypeptide containing a membrane-spanning domain. Furthermore, for formulations containing liposomes, an antigen in a detergent solution (e.g., a cell membrane extract) may be mixed with lipids, and liposomes then may be formed by removal of the detergent by dilution, dialysis, or column chromatography.

In some embodiments, a vaccine composition is administered in combination with other therapeutic ingredients including, e.g., γ-interferon, cytokines, chemotherapeutic agents, or anti-inflammatory or anti-viral agents.

In some embodiments, a vaccine composition is administered in a pure or substantially pure form, but it is preferable to present it as a pharmaceutical composition, formulation or preparation. Such formulation comprises polypeptides described herein together with one or more pharmaceutically acceptable carriers and optionally other therapeutic ingredients. Other therapeutic ingredients include compounds that enhance antigen presentation, e.g., gamma interferon, cytokines, chemotherapeutic agents, or anti-inflammatory agents. The formulations can conveniently be presented in unit dosage form and may be prepared by methods well known in the pharmaceutical art. For example, Plotkin and Mortimer (In 'Vaccines', 1994, W.B. Saunders Company; 2nd edition) describes vaccination of animals or humans to induce an immune response specific for particular pathogens, as well as methods of preparing antigen, determining a suitable dose of antigen, and assaying for induction of an immune response.

In some embodiments, a vaccine composition as described herein further comprises an adjuvant, as described herein.

Formulations of vaccine compositions suitable for intravenous, intramuscular, intranasal, oral, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g., 0.1-2.0 M), glycine, and the like, and having a buffered pH compatible with physiological conditions to produce an aqueous solution, and rendering the solution sterile. These may be present in unit or multi-dose containers, for example, sealed ampoules or vials.

Liposomal suspensions can also be used as pharmaceutically acceptable carriers. These can be prepared according to methods known to those skilled in the art, for example, as described in U.S. Pat. No. 4,522,811.

Formulations for an intranasal delivery are described in U.S. Pat. Nos. 5,427,782, 5,843,451 and 6,398,774, which are incorporated herein in their entirety by reference. Other means of mucosal administration are also encompassed herein.

The formulations of a vaccine composition as disclosed herein can also incorporate a stabilizer. Illustrative stabilizers are polyethylene glycol, proteins, saccharide, amino acids, inorganic acids, and organic acids which may be used either on their own or as admixtures. Two or more stabilizers may be used in aqueous solutions at the appropriate concentration and/or pH. The specific osmotic pressure in such aqueous solution is generally in the range of 0.1-3.0 osmoses, preferably in the range of 0.80-1.2. The pH of the aqueous solution is adjusted to be within the range of 5.0-9.0, preferably within the range of 6-8.

When oral preparations are desired, a vaccine composition can be combined with typical carriers, such as lactose, sucrose, starch, talc magnesium stearate, crystalline cellulose, methyl cellulose, carboxymethyl cellulose, glycerin, sodium alginate or gum arabic among others.

A method of immunization or vaccinating a mammal against pneumococcal infections comprises administering a vaccine composition described herein.

In some embodiments, the vaccine compositions described herein can be administered intravenously, intranasally, intramuscularly, subcutaneously, infraperitoneally or orally. A preferred route of administration is intranasal or by other mucosal route.

Vaccination can be conducted by conventional methods. For example, an immunogen as polypeptide as disclosed in Table 1 can be used in a suitable diluent such as saline or water, and optionally with complete or incomplete adjuvants. The vaccine can be administered by any route appropriate for eliciting an immune response. The vaccine can be administered once or at periodic intervals until an immune response is elicited. Immune responses can be detected by a variety of methods known to those skilled in the art, including but not limited to, antibody production, cytotoxicity assay, proliferation assay and cytokine release assays. For example, samples of blood can be drawn from the immunized mammal, and analyzed for the presence of antibodies against the immungen protein used in the vaccination by ELISA and the titer of these antibodies can be determined by methods known in the art.

The precise dose to be employed in the formulation will also depend on the route of administration and should be decided according to the judgment of the practitioner and each patient's circumstances. For example, a range of 25 µg-900 µg total immunogen protein can be administered intradermally, monthly for 3 months.

Ultimately, the attending physician will decide the amount of protein or vaccine composition to administer to particular individuals.

Alternatively, such proteins or immunogen mixtures may be useful in diagnostics.

Examples

Example 1

Pneumococcal Immunogens

Protein Isolation

Initial efforts to isolate these proteins via gel filtration of the WCC supernatant did not yield discrete enough separation of proteins. Ultimately, preparative SDS gel transverse elution of the WCC supernatant improved separation of the proteins. WCC supernatant with SDS buffer was loaded into 10 wells of a precast 4%-12% Bis/Tris SDS gel with ~100 µg protein/lane and run at 200V over 30 min in MES-SDS buffer. This gel was equilibrated in 2 mM phosphate buffer for 20 mm in fresh buffer three times to minimize SDS. The equilibrated gel was cut to size to fit the BioRad Mini Gel Eluter apparatus. Proteins were transversely eluted through the thickness of the gel with 90 mA of current for 20 min. Eluates were collected into the elution chambers beneath the gel and harvested by vacuum apparatus. This method yielded fourteen eluates with one or two protein bands per eluate. The proteins within each eluate were visualized on silver stained SDS gel; bands within each eluate were reproducible from elution to elution; eluates were combined for further use.

Protein Identification

Eluates were used as stimuli on splenocytes from C57Bl/6 mice immunized with WCC to determine which eluates contained proteins capable of eliciting IL-17A production. Mice (n=10) were immunized intranasally with WCC one week apart. Three weeks following their second immunization, spleens were harvested and processed into a cell suspension in DMEM with L-glutamine/10% FCS/2ME/cipro. The protein concentration within each eluate was determined by quantitative BCA assay; eluates were used as stimuli with each stimulus normalized to the lowest concentration among the eluates. Supernatants were harvested after six days and assayed for IL-17A by ELISA (R&D Biosciences). We then submitted the predominant band or bands from the most stimulatory eluates for mass spectroscopic analysis.

Protein Expression and Purification

Antigens were selected from the compiled mass spectroscopy data based on clinical safety criteria such as lack of human homology and conservation across sequenced pneumococcal strains.

Selected antigens (n=12) were cloned into competent *E. coli* cells for expression using the pQE-30 plasmid vector incorporating a 6×-histidine (his) tag. Transformed *E. coli* colonies were sequenced for the protein of interest; transformants containing successfully cloned proteins were grown and induced for protein expression using IPTG. After overnight incubation allowing expression, transformants were spun down and pellets were lysed by sonication. The proteins of interest were purified from the lysed cell supernatant over a column using agarose-Ni beads to bind the His-tag; proteins were eluted in imidazole buffer after careful washing of the column. Protein-containing elutions were further purified over a desalting column prior to use in cellular stimulation assays.

Assessing Immunogenicity of Purified Proteins

In an effort to prioritize which of the twelve purified proteins for test vaccines in animal models, each protein's immunogenicity was assessed in the splenocyte stimulation assay performed similarly to the assay described above used to identify which eluates contained stimulatory proteins.

Splenocytes from a separate cohort of ten WCC-immunized C57Bl/6 animals were stimulated with 10 µg/ml of each of the twelve proteins.

Assessing the Protective Capacity of Purified Proteins Against Colonization

In the first immunization experiment, C57Bl/6 mice (n=10 per group) were immunized intranasally twice one week apart with a combination of the three most stimulatory proteins (SPN0435, SPN1534, and SPN2070). The combination vaccine contained 4 µg of each protein per vaccine dose. Vaccines were prepared with cholera toxin (CT) adjuvant. Control cohorts were immunized with WCV and CT or CT alone. Three weeks following their 2nd immunization, animals were bled; whole blood was stimulated with the whole cell antigen and IL-17A was measured from the supernatant to assess immunogenicity. One week after being bled, animals were challenged intranasally with a live type 6B pneumococcal strain. One week after challenge, animals were sacrificed and nasal washes were obtained and cultured to assess density of colonization.

Figure 6:
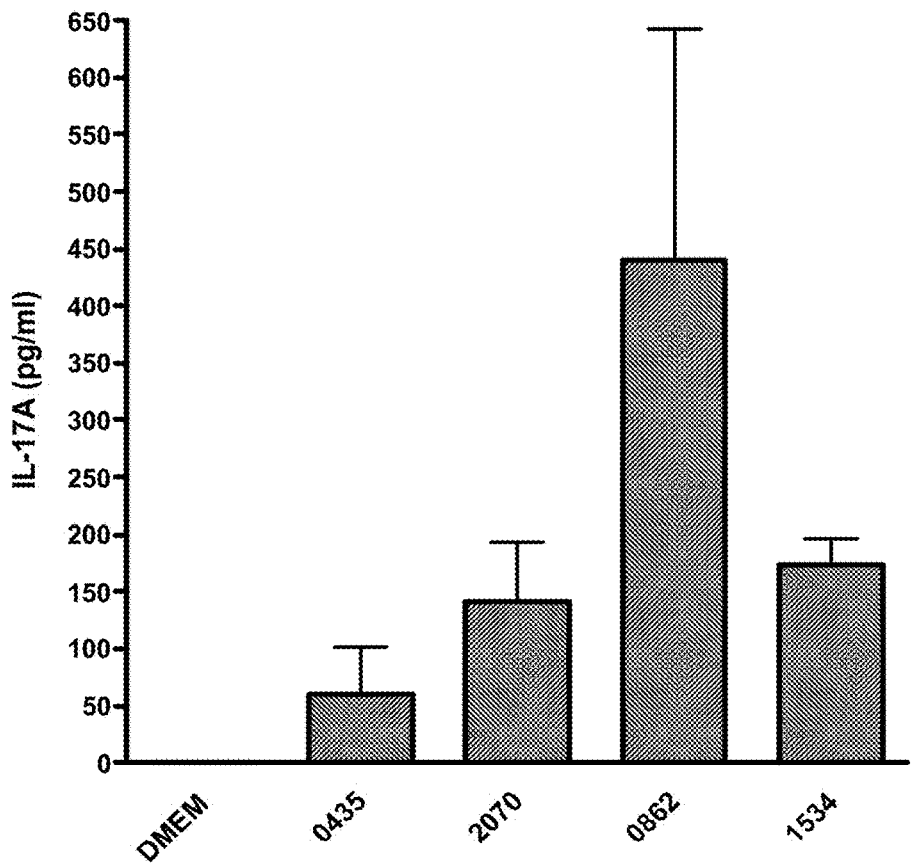
FIG. 6 shows protection against colonization by individual proteins in outbred CD1 mice. Immunization and challenge schedule was the same as in FIG. 4. NP colonization density was compared by the Mann-Whitney U test or by the Kruskal-Wallis test with Dunn's correction for multiple comparisons using PRISM. *, $p<0.05$; **, $p<0.01$.

In the next immunization study, the three proteins contained within the combination were used individually as vaccines (FIG. 6). Another protein (SPN 0862), which elicited IL-17A in the splenocyte stimulation assay, was also tested. A group of animals immunized with a protein that had not been stimulatory in any of the cellular assays (SPN 2092) were included as a negative control. All proteins were further purified by gel filtration to remove any contaminants prior to use as individual vaccines.

REFERENCES

All references described herein are incorporated herein in their entirety by reference.

The invention claimed is:

1. An immunogenic composition comprising:
   (i) an antigenic polypeptide comprising the amino acid sequence of SEQ ID NO:44;
   (ii) an antigenic polypeptide comprising the amino acid sequence of SEQ ID NO:28 or 29; or an antigenic polypeptide comprising the amino acid sequence of SEQ ID NO:10 or 11; and
   (iii) an adjuvant,
   wherein the composition comprises suitable doses of the antigenic polypeptides such that upon administration to a mammal, the immunogenic composition elicits an immune response to the antigenic polypeptides in the mammal.

2. The immunogenic composition of claim 1, wherein the immune response is a T cell response, a B cell response, or a combination thereof.

3. The immunogenic composition of claim 2, wherein the T cell response is a Th17 cell response, CD4+ T cell response, CD8+ T cell response, or a combination thereof.

4. A pneumococcal vaccine comprising the immunogenic composition of claim 1.

5. The vaccine of claim 4, further comprising a pharmaceutically acceptable carrier.

6. The vaccine of claim 4, wherein the vaccine is suitable for intravenous, intramuscular, intranasal, oral, subcutaneous, or intraperitoneal administration.

7. The vaccine of claim 4, wherein administration of the vaccine to a mammal results in immunization of the mammal against pneumococcal infection.

8. The immunogenic composition of claim 1, wherein the adjuvant is selected from the group consisting of cholera toxin, CFA, IFA, and alum.

9. The immunogenic composition of claim 1, comprising an antigenic polypeptide comprising the amino acid sequence of SEQ ID NO:44; an antigenic polypeptide comprising the amino acid sequence of SEQ ID NO:28 or 29; and an antigenic polypeptide comprising the amino acid sequence of SEQ ID NO:10 or 11.

* * * * *